United States Patent
Andersen

(10) Patent No.: US 10,538,751 B2
(45) Date of Patent: Jan. 21, 2020

(54) ALPHA-AMYLASE VARIANTS AND POLYNUCLEOTIDES ENCODING SAME

(71) Applicant: NOVOZYMES A/S, Bagsvaerd (DK)

(72) Inventor: Carsten Andersen, Bagsvaerd (DK)

(73) Assignee: NOVOZYMES A/S, Bagsvaerd (DK)

(*) Notice: Subject to any disclaimer, the term of this patent is extended or adjusted under 35 U.S.C. 154(b) by 0 days.

(21) Appl. No.: 14/896,300

(22) PCT Filed: Jun. 4, 2014

(86) PCT No.: PCT/EP2014/061572
§ 371 (c)(1),
(2) Date: Dec. 4, 2015

(87) PCT Pub. No.: WO2014/195356
PCT Pub. Date: Dec. 11, 2014

(65) Prior Publication Data
US 2016/0201042 A1 Jul. 14, 2016

(30) Foreign Application Priority Data
Jun. 6, 2013 (EP) .................................... 13170894

(51) Int. Cl.
| | | |
|---|---|---|
| *C12N 9/28* | (2006.01) | |
| *C12N 15/00* | (2006.01) | |
| *C12N 1/20* | (2006.01) | |
| *C12P 21/06* | (2006.01) | |
| *C12P 21/04* | (2006.01) | |
| *C07H 21/04* | (2006.01) | |
| *C11D 3/386* | (2006.01) | |
| *C12N 15/09* | (2006.01) | |

(52) U.S. Cl.
CPC ............ *C12N 9/2417* (2013.01); *C11D 3/386* (2013.01); *C12N 15/00* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 7,432,099 B2* | 10/2008 | Andersen | C11D 3/386 435/201 |
| 8,153,412 B2* | 4/2012 | Chang | C11D 3/386 426/42 |
| 8,852,912 B2* | 10/2014 | Estell | C11D 3/38681 435/183 |
| 2006/0147581 A1 | 7/2006 | Svendsen | |
| 2011/0195481 A1 | 8/2011 | Svendsen | |
| 2012/0045822 A1 | 2/2012 | Concar | |
| 2012/0258497 A1 | 10/2012 | Andersen | |
| 2016/0017305 A1* | 1/2016 | Cascao-Pereira | C11D 3/386 435/99 |

FOREIGN PATENT DOCUMENTS

| | | |
|---|---|---|
| WO | 2004/113551 A1 | 12/2004 |
| WO | 2007/079938 A2 | 7/2007 |
| WO | 2008/153805 A2 | 12/2008 |
| WO | 2009/061380 A2 | 5/2009 |
| WO | 2009/134670 A2 | 11/2009 |

OTHER PUBLICATIONS

Chang et al, 2013, Appl Biochem Biotechnol 169(6), 1870-1883.
Shiau, 2003, Appl Environ Micro 69, 2383-2385.
Suzuki et al, 1989, J Biol Chem 264(32), 18933-18938.
Igarashi et al, 1998, Biochem Biophys Res Com 248(2), 372-377.

* cited by examiner

*Primary Examiner* — Yong D Pak
(74) *Attorney, Agent, or Firm* — David Fazzolare

(57) ABSTRACT

The present invention relates to alpha-amylase variants. The present invention also relates to polynucleotides encoding the variants; nucleic acid constructs, vectors, and host cells comprising the polynucleotides; and methods of using the variants.

23 Claims, No Drawings
Specification includes a Sequence Listing.

ALPHA-AMYLASE VARIANTS AND POLYNUCLEOTIDES ENCODING SAME

CROSS-REFERENCE TO RELATED APPLICATIONS

This application is a 35 U.S.C. 371 national application of PCT/EP2014/061572 filed Jun. 4, 2014, which claims priority or the benefit under 35 U.S.C. 119 of European application no. 13170894.3 filed Jun. 6, 2013, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to alpha-amylase variants, polynucleotides encoding the variants, methods of producing the variants, and methods of using the variants.

Description of the Related Art

Alpha-amylases (alpha-1,4-glucan-4-glucanohydrolases, E.C. 3.2.1.1) constitute a group of enzymes, which catalyses hydrolysis of starch and other linear and branched 1,4-gluosidic oligo- and polysaccharides.

There is a long history of industrial use of alpha-amylases in several known applications such as detergent, baking, brewing, starch liquefaction and saccharification e.g. in preparation of high fructose syrups or as part of ethanol production from starch. These and other applications of alpha-amylases are known and utilize alpha-amylases derived from microorganisms, in particular bacterial alpha-amylases.

Among the first bacterial alpha-amylases to be used were an alpha-amylase from *B. licheniformis*, also known as Termamyl which have been extensively characterized and the crystal structure has been determined for this enzyme. *Bacillus* amylases, such as Termamyl and SP707, form a particular group of alpha-amylases that have found use in detergents. Many of these known bacterial amylases have been modified in order to improve their functionality in a particular application.

Methods of increasing the thermostability of alpha-amylases have been well studied. Suzuki et al. (1989) disclose chimeric alpha-amylases, in which specified regions of a *B. amyloliquefaciens* alpha-amylase have been substituted for the corresponding regions of a *B. licheniformis* alpha-amylase. The chimeric alpha-amylases were constructed with the purpose of identifying regions responsible for thermostability. Such regions were found to include amino acid residues 177-186 and amino acid residues 255-270 of the *B. amyloliquefaciens* alpha-amylase. Igarashi et al. 1998 show that the thermostability of AmyS-type amylases can be increased by the deletion of two amino acid residues, R179-G180, (AmyS numbering) from a loop (F178 to A184). However, Shiau et al. (2003) showed that an AmyS enzyme with deletion in the same loop has a lower specific activity for corn starch hydrolysis at high-temperature than the parent enzyme, negating one of the principal advantages of AmyS amylases.

For environmental reasons it has been increasingly important to lower the temperature in washing, dishwashing and/or cleaning processes. However, most enzymes including amylases have a temperature optimum which is above the temperature usually used in low temperature washing. Alpha-amylase is a key enzyme for use in detergent compositions and its use has become increasingly important for removal of starchy stains during laundry washing or dishwashing. Therefore, it is important to find alpha-amylase variants, which retain their wash performance, stain removal effect and/or activity when the temperature is lowered. However, despite the efficiency of current detergents enzyme compositions, there are many stains that are difficult to completely remove. These problems are compounded by the increased use of low (e.g., cold water) wash temperatures and shorter washing cycles. Thus, it is desirable to have amylolytic enzymes that can function under low temperature and at the same time preserve or increase other desirable properties such as specific activity (amylolytic activity), stability and/or wash performance.

Thus, it is an object of the present invention to provide alpha-amylases variants which have high performance, in particular high wash performance, at low temperatures and/or which have high stability in detergent compositions and/or which have high amylase activity after storage in detergents.

It is another object of the present invention to provide alpha-amylase variants that exhibit a high level of stability when incorporated into detergent compositions such as liquid detergents, in particular in the presence of chelating agents, surfactants, proteases and/or alkaline conditions.

The present invention provides alpha-amylase variants with improved stability compared to its parent.

SUMMARY OF THE INVENTION

The present invention relates to an isolated alpha-amylase variant comprising a) a deletion at two or more positions corresponding to positions R180, S181, T182 and G183 of the mature polypeptide of SEQ ID NO: 1 or 2, and b) an alteration at one or more positions corresponding to positions Y48, E169, S170, R171, K172, L173, N174, L205, R309, M317, I390, of the mature polypeptide of SEQ ID NO: 1 or 2, wherein each alteration is independently a substitution or an insertion and wherein the variant has at least 80%, such as at least 90%, but less than 100% sequence identity with the mature polypeptide of SEQ ID NO: 1 or 2 and wherein the variant has alpha-amylase activity.

The present invention also relates to detergent compositions comprising the variants, isolated polynucleotides encoding the variants; nucleic acid constructs, vectors, and host cells comprising the polynucleotides; and methods of producing the variants.

The present invention also relates to the use of the variants in a cleaning process. The present invention also relates to a method of improving the detergent stability of an alpha-amylase by introducing into a parent alpha-amylase a) a deletion at two or more positions corresponding to positions R180, S181, T182 and G183 of the mature polypeptide of SEQ ID NO: 1 or 2 and b)
an alteration at one or more positions corresponding to positions Y48, E169, S170, R171, K172, L173, N174, L205, R309, M317, I390, of the mature polypeptide of SEQ ID NO: 1 or 2,
wherein each alteration is independently a substitution or an insertion, wherein the resulting variant has at least 80%, such as at least 90%, but less than 100% sequence identity with the mature polypeptide of SEQ ID NO: 1 or 2, wherein the resulting variant has alpha-amylase activity and an improved detergent stability compared to the parent alpha-amylase.

Definitions

Alpha-amylase: The term "alpha-amylase activity" means the activity of alpha-1,4-glucan-4-glucanohydrolases, E.C. 3.2.1.1, which constitute a group of enzymes, which catalyze hydrolysis of starch and other linear and branched 1,4-glucosidic oligo- and polysaccharides. For purposes of the present invention, alpha-amylase activity is determined according to the procedure described in the Methods. In one aspect, the variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1 or 2.

```
SEQ ID NO: 1:
NTAPINETMM QYFEWDLPND GTLWTKVKNE AANLSSLGIT

ALWLPPAYKG TSQSDVGYGV YDLYDLGEFN QKGTIRTKYG

TKTQYIQAIQ AAKAAGMQVY ADVVFNHKAG ADGTEFVDAV

EVDPSNRNQE TSGTYQIQAW TKFDFPGRGN TYSSFKWRWY

HFDGTDWDES RKLNRIYKFR STGKAWDWEV DTENGNYDYL

MFADLDMDHP EVVTELKNWG TWYVNTTNID GFRLDAVKHI

KYSFFPDWLT YVRNQTGKNL FAVGEFWSYD VNKLHNYITK

TNGSMSLFDA PLHNNFYTAS KSSGYFDMRY LLNNTLMKDQ

PSLAVTLVDN HDTQPGQSLQ SWVEPWFKPL AYAFILTRQE

GYPCVFYGDY YGIPKYNIPG LKSKIDPLLI ARRDYAYGTQ

RDYIDHQDII GWTREGIDTK PNSGLAALIT DGPGGSKWMY

VGKKHAGKVF YDLTGNRSDT VTINADGWGE FKVNGGSVSI

WVAKTSNVTF TVNNATTTSG QNVYVVANIP ELGNWNTANA

IKMNPSSYPT WKATIALPQG KAIEFKFIKK DQAGNVIWES

TSNRTYTVPF SSTGSYTASW NVP

SEQ ID NO: 2:
NTAPINETMM QYFEWDLPND GTLWTKVKNE AANLSSLGIT

ALWLPPAYKG TSQSDVGYGV YDLYDLGEFN QKGTIRTKYG

TKTQYIQAIQ AAKAAGMQVY ADVVFNHKAG ADGTEFVDAV

EVDPSNRNQE TSGTYQIQAW TKFDFPGRGN TYSSFKWRWY

HFDGTDWDES RKLNRIYKFR STGKAWDWEV DTENGNYDYL

MFADLDMDHP EVVTELKNWG TWYVNTTNID GFRLDAVKHI

KYSFFPDWLT YVRNQTGKNL FAVGEFWSYD VNKLHNYITK

TNGSMSLFDA PLHNNFYTAS KSSGYFDMRY LLNNTLMKDQ

PSLAVTLVDN HDTQPGQSLQ SWVEPWFKPL AYAFILTRQE

GYPCVFYGDY YGIPKYNIPG LKSKIDPLLI ARRDYAYGTQ

RDYIDHQDII GWTREGIDTK PNSGLAALIT DGPGGSKWMY

VGKKHAGKVF YDLTGNRSDT VTINADGWGE FKVNGGSVSI

WVAK
```

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has alpha-amylase activity. In one aspect, a fragment contains at least 480 amino acid residues, at least 481 amino acid residues, or at least 482 amino acid residues.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent or compared to the mature polypeptide of SEQ ID NO: 1 or 2. Such improved properties include, but are not limited to, catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity, and thermo stability, and improved wash performance, particularly improved wash performance at low temperatures, such as temperatures between 5° C. and 35° C., such as below 35° C., or below 30° C., or even below 20° C., or at temperatures below 15° C., or even at temperatures below 10° C. Another property that may be improved in the variants is the stability in detergent compositions, i.e. detergent stability. The detergent stability (or residual activity) of a given variant can be determined by incubating the variant in a detergent model solution preferably containing chelating agents such as EDTA, EGTA, DTPA, DTMPA, MGDA or HEDP. For example, 90 vol % of model detergent A (see below) containing DTMPA (final concentration 0.2%) are incubated with 10 vol % amylase solution (0.6 mg/ml) at 40° C. for 1 hour. As another example, 90 vol % of model detergent A (see below) further containing HEDP (final concentration 1.5%) are incubated with 10 vol % amylase solution (0.6 mg/ml) at 37° C. for 2 hours. The amylase activity after incubation for a given time period at a given temperature is determined, for example by using the EnzCheck assay as described below. This activity is then compared to the activity of a reference incubated at 4° C. for the same time period in the same detergent composition. As another example, 90% final concentration of detergent A further containing an additional 0.5% (w/v) final concentration of EDTA are incubated with 10 vol % amylase solution (0.6 mg/ml). The amylase activity after incubation for a given time period at a given temperature is determined, for example by using the Phadebas assay as described below. This activity is then compared to the activity of a reference incubated at 4° C. for the same time period in the same detergent composition. The lesser the difference between both treatments, the higher is the detergent stability. Similar tests can be done using model detergent J or other detergents containing chelators.

Wash performance: In the present context the term "wash performance" is used as an enzyme's ability to remove starch or starch-containing stains present on the object to be cleaned during e.g. laundry or hard surface cleaning, such as dish wash. The wash performance may be quantified by calculating the so-called delta remission value (ΔRem) as described in the definition herein.

Improved wash performance: The term "improved wash performance" is defined herein as a variant enzyme displaying an alteration of the wash performance of an amylase variant relative to the wash performance of the parent amylase or relative to the alpha-amylase having the amino acid sequence shown in SEQ ID NO 1 or 2, e.g. by increased stain removal. The term "wash performance" includes cleaning in general e.g. hard surface cleaning as in dish wash, but also wash performance on textiles such as laundry, and also industrial and institutional cleaning. Improved wash performance may be measured by comparing of the so-called delta remission value (ΔRem) as described in the definition herein.

Low temperature: "Low temperature" is a temperature of 5-35° C., preferably 5-30° C., more preferably 5-25° C., more preferably 5-20° C., most preferably 5-15° C., and in particular 5-10° C. In a preferred embodiment, "Low temperature" is a temperature of 10-35° C., preferably 10-30° C., more preferably 10-25° C., most preferably 10-20° C., and in particular 10-15° C.

Delta remission value (ΔRem): The terms "Delta remission" or "Delta remission value" are defined herein as the result of a reflectance or remission measurement at 460 nm of a test material, e.g. a swatch CS-28 (Center For Testmaterials BV, P.O. Box 120, 3133 KT Vlaardingen, the Netherlands) or a hard surface. The swatch is measured with at least one other swatch, washed under identical conditions, as background. The delta remission is the remission value of the test material washed with amylase subtracted the remission value of the test material washed without amylase.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 583 of SEQ ID NO: 1. In another aspect, the polypeptide has a truncation of the C-terminal CBM so that the mature polypeptide means amino acids 1-484 of SEQ ID NO: 1 corresponding to SEQ ID NO:2.

It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having alpha-amylase activity.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent alpha-amylase: The term "parent" or "parent alpha-amylase" means an alpha-amylase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the nobrief option) is used as the percent identity and is calculated as follows:

(Identical Residues×100)/(Length of Alignment Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the nobrief option) is used as the percent identity and is calculated as follows:

(Identical Deoxyribonucleotides×100)/(Length of Alignment Total Number of Gaps in Alignment)

Variant: The term "variant" means a polypeptide having alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1 or 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type alpha-amylase: The term "wild-type" alpha-amylase means an alpha-amylase expressed by a naturally occurring microorganism, such as a bacterium, archaea, yeast, or filamentous fungus found in nature.

Conventions for Designation of Variants

For purposes of the present invention, the mature polypeptide disclosed in SEQ ID NO: 1 is used to determine the corresponding amino acid residue in another alpha-amylase. The amino acid sequence of another alpha-amylase is aligned with the mature polypeptide disclosed in SEQ ID NO: 1, and based on the alignment, the amino acid position number corresponding to any amino acid residue in the mature polypeptide disclosed in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". In situations where the amino acid at a given position may be substituted for any other amino acid it is designated T226ACDEFGHIKLMNPQRSWVY. Accordingly, this means that threonine at position 226 may be substituted with one amino acid selected from the group of A, C, D, E, F, G, H, I, K, L, M, N, P, Q, R, S, W, V or Y. Likewise, in situations where the amino acid at a given position may be substituted for one amino acid selected from a specific group of amino acids, e.g. where the threonine at position 226 may be substituted with any of tyrosine, phenylalanine or histidine it is designated T226YFH. The different alterations at a given position may also be separated by a comma, e.g., "Arg170Tyr,Glu" or "R170Y,E" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+ Arg170Ala", "Tyr167Ala+Arg170Gly", and "Tyr167Ala+ Arg170Ala".

Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+ S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

DETAILED DESCRIPTION OF THE INVENTION

The present invention relates to an isolated alpha-amylase variant comprising a) a deletion at two or more positions corresponding to positions R180, S181, T182 and G183 of the mature polypeptide of SEQ ID NO: 1 or 2, and b) an alteration at one or more positions corresponding to positions Y48, E169, S170, R171, K172, L173, N174, L205, R309, M317, I390, D16, N19, Q53, V60, F105, F116, P124, S125, N128, T131, G133, K178, A185, E189, N194, A203, M208, H209, E211, V212, V213, K241, Y242, F245, F266, Y269, K280, G283, M285, N294, L323, K375, I404 and Q407 of the mature polypeptide of SEQ ID NO: 1 or 2, wherein each alteration is independently a substitution, deletion or insertion, wherein the variant has at least 80%, such as at least 90%, but less than 100% sequence identity with the mature polypeptide of SEQ ID NO: 1 or 2, wherein the variant has alpha-amylase activity. In another embodiment the variant has at least 80%, such as at least 90%, but less than 100% sequence identity with the mature polypeptide of SEQ ID NO: 3. In another embodiment the variant has at least 80%, such as at least 90%, but less than 100% sequence identity with the mature polypeptide of SEQ ID NO: 4. In another embodiment the variant has at least 80%, such as at least 90%, but less than 100% sequence identity with the mature polypeptide of SEQ ID NO: 5. In another embodiment the variant has at least 80%, such as at least 90%, but less than 100% sequence identity with the mature polypeptide of SEQ ID NO: 6. In another embodiment the variant has at least 80%, such as at least 90%, but less than 100% sequence identity with the mature polypeptide of SEQ ID NO: 7. In another embodiment the variant has at least 80%, such as at least 90%, but less than 100% sequence identity with the mature polypeptide of SEQ ID NO: 8.

In one embodiment the alteration b) is an insertion in the loop spanning from amino acid positions 170-174. The insertion may be selected from the list comprising: S170SA, S170SC, S170SD, S170SE, S170SF, S170SG, S170SH, S170SI, S170SK, S170SL, S170SM, S170SN, S170SP, S170SQ, S170SR, S170SS, S170ST, S170SV, S170SW, S170SY, R171RA, R171RC, R171RD, R171RE, R171RF, R171RG, R171RH, R171RI, R171RK, R171RL, R171RM, R171RN, R171RP, R171RQ, R171RR, R171RS, R171RT, R171RV, R171RW, R171RY, K172KA, K172KC, K172KD, K172KE, K172KF, K172KG, K172KH, K172KI, K172KK, K172KL, K172KM, K172KN, K172KP, K172KQ, K172KR, K172KS, K172KT, K172KV, K172KW, K172KY, L173LA, L173LC, L173LD, L173LE, L173LF, L173LG, L173LH, L173LI, L173LK, L173LL, L173LM, L173LN, L173LP, L173LQ, L173LR, L173LS, L173LT, L173LV, L173LW, L173LY, N174NA, N174NC, N174ND, N174NE, N174NF, N174NG, N174NH, N174NI, N174NK, N174NL, N174NM, N174NN, N174NP, N174NQ, N174NR, N174NS, N174NT, N174NV, N174NW, N174NY.

In one embodiment the alteration b) is selected from one or more of Y48W, Y48F, E169EQ, S170SL, R171RR, R171RQ, R171RL, R171RN, R171RF, K172KA, K172KF, K172KL, K172KN, K172KR, L173LR, L173LF, L173LL, L173LA, N174NQ, N174NF, N174NL, N174NA, N174NN, N174NS, L205F, L205Y, L205I, R309Q, M317F, M317I, M317L, M317V, M317Y, I390E, I390D, I390Q, I390N, N194F+L205Y, N194F+L205F, N194Y+L205Y, N194Y+L205F, Y48W+L205Y, V60A+L205Y, Y48W+V60A+L205F, Y48W+V60A+L205Y, D16Y, N19D, Q53R, V60A, F105M, F116W, P124*, P124D, P124S, P124T, S125N, S125P, N128F, N128H, N128I, N128K, N128R, T131D, T131E, T131L, G133D, K172Q, L173F, L173Y, N174NE, N174ND, K178L, A185F, A185H, A185L, A185I, A185P, E189P, N194F, N194Y, N194H, N194L, N194I, A203S, A203T, L205I, M208F, M208I, M208L, M208Y, H209D, H209M, H209T, E211D, E211L, V212G, V212A, V212S, V212T, V212P, V212N, V212I, V213I, V213S, V213T, V213Q, K241R, Y242F, F245I, F245L, F245M, F245S, F245T, F245V, F245Y, F266Y, Y269N, K280R, G283S, M285F, M285H, N294Y, M317F, L323H, K375Q, I404F, I404L, I404Y, Q407H, N194F+L205Y, N194F+L205F, N194Y+L205Y, N194Y+L205F, V212S+V213T, V212G+V213T, V212N+V213I, V212N+V213Q, V212P+V213T, D16Y+K375Q, N19D+Q53R, Y48W+V60A, Y48W+F105M, Y48W+L205Y, V60A+L205Y, Y48W+V60A+F105M, Y48W+V60A+L205F, V60A+F105M+L205F, Y48W+V60A+F105M+L205F, Y48W+V60A+L205Y, V60A+F105M+L205Y, Y48W+V60A+F105M+L205Y, P124D+S125P, P124D+S125N, S125N+N174NN, K172Q+N174NQ, K172Q+L173F, K172Q+L173F+N174NQ, Y242F+F266Y, Y269N+N294Y and G283S+L323H.

In a preferred embodiment, the alteration b) comprises or consists of a substitution selected from the list consisting of L205Y, L205F, Y48W, R309Q, M317L, I390E or an insertion selected from the list consisting of N174NQ, N174NL and N174NN In another embodiment, the alteration b) comprises or consists of a substitution selected from N194F or N194Y.

In a preferred embodiment, the deletion a) is selected from the list consisting of R180*+S181*, R180*+T182*, R180*+G183*, S181*+T182*, S181*+G183* and T182*+G183*, preferably R180*+S181*.

In a preferred embodiment, the deletion a) and alteration b) are selected from the list consisting of L205Y+R180*+S181*, L205Y+R180*+T182*, L205Y+R180*+G183*, L205Y+S181*+T182*, L205Y+T182*+G183*, L205F+R180*+S181*, L205F+R180*+T182*, L205F+R180*+G183*, L205F+S181*+T182*, L205F+T182*+G183*, Y48W+R180*+S181*, Y48W+R180*+T182*, Y48W+R180*+G183*, Y48W+S181*+T182*, Y48W+T182*+G183*, R309Q+R180*+S181*, R309Q+R180*+T182*, R309Q+R180*+G183*, R309Q+S181*+T182*, R309Q+T182*+G183*, M317L+R180*+S181*, M317L+R180*+T182*, M317L+R180*+G183*, M317L+S181*+T182*, M317L+T182*+G183*, N174NQ+R180*+S181*, N174NQ+R180*+T182*, N174NQ+R180*+G183*, N174NQ+S181*+T182*, N174NQ+T182*+G183*, N174NN+R180*+S181*, N174NN+R180*+T182*, N174NN+R180*+G183*, N174NN+S181*+T182*, N174NN+T182*+G183*, N174NL+R180*+S181*, N174NL+R180*+T182*, N174NL+R180*+G183*, N174NL+S181*+T182*, N174NL+T182*+G183*, N174NA+R180*+S181*, N174NA+R180*+T182*, N174NA+R180*+G183*, N174NA+S181*+T182*, N174NA+T182*+G183*, Y48W+L205Y+R180*+S181*, Y48W+L205Y+R180*+T182*, Y48W+L205Y+R180*+G183*, Y48W+L205Y+S181*+T182*, Y48W+L205Y+T182*+G183*, V60A+L205Y+R180*+S181*, V60A+L205Y+R180*+T182*, V60A+L205Y+R180*+G183*, V60A+L205Y+S181*+T182*, V60A+L205Y+T182*+G183*, Y48W+V60A+L205Y+R180*+S181*, Y48W+V60A+L205Y+R180*+T182*, Y48W+V60A+L205Y+S181*+T182*, Y48W+V60A+L205Y+T182*+G183*, I390E+R180*+S181*, I390E+R180*+T182*, I390E+R180*+G183*, I390E+S181*+T182*, I390E+T182*+G183*, E169EQ+R180*+S181*, E169EQ+R180*+T182*, E169EQ+R180*+G183*, E169EQ+S181*+T182*, and E169EQ+T182*+G183*, N194F+R180*+S181*, N194F+R180*+T182*, N194F+R180*+G183*, N194F+S181*+T182*, N194F+T182*+G183*, N194Y+R180*+S181*, N194Y+R180*+T182*, N194Y+R180*+G183*, N194Y+S181*+T182*, N194Y+T182*+G183*, V212G+R180*+S181*, V212G+R180*+T182*, V212G+R180*+G183*, V212G+S181*+T182*, V212G+T182*+G183*, V212S+R180*+S181*, V212S+R180*+T182*, V212S+R180*+G183*, V212S+S181*+T182*, V212S+T182*+G183*, V212P+R180*+S181*, V212P+R180*+T182*, V212P+R180*+G183*, V212P+S181*+T182*, V212P+T182*+G183*, V212T+R180*+S181*, V212T+R180*+T182*, V212T+R180*+G183*, V212T+S181*+T182*, V212T+T182*+G183*, V213I+R180*+S181*, V213I+R180*+T182*, V213I+R180*+G183*, V213I+S181*+T182*, V213I+T182*+G183*, V213T+R180*+S181*, V213T+R180*+T182*, V213T+R180*+G183*, V213T+S181*+T182*, V213T+T182*+G183*, K178L+R180*+S181*, K178L+R180*+T182*, K178L+R180*+G183*, K178L+S181*+T182*, K178L+T182*+G183*, E189P+R180*+S181*, E189P+R180*+T182*, E189P+R180*+G183*, E189P+S181*+T182*, and E189P+T182*+G183*.

In another embodiment, the alteration a) and variation b) are selected from the list consisting of N194F+R180*+S181*, N194F+R180*+T182*, N194F+R180*+G183*, N194F+S181*+T182*, N194F+T182*+G183*, N194Y+R180*+S181*, N194Y+R180*+T182*, N194Y+R180*+G183*, N194Y+S181*+T182* and N194Y+T182*+G183*.

In another embodiment, the alteration a) and variation b) are selected from the list consisting of N194F+L205Y+R180*+S181*, N194F+L205Y+R180*+T182*, N194F+L205Y+R180*+G183*, N194F+L205Y+S181*+T182* or N194F+L205Y+T182*+G183*.

In another embodiment, the variant further comprises a substitution at one or both positions corresponding to positions G475 and S243 of the mature polypeptide of SEQ ID NO: 1 or 2, preferably G475K and/or S243Q.

In another embodiment, the alteration b) is at two or more of said positions, such as three or more of said positions, four or more of said positions, five or more of said positions, six or more of said positions, seven or more of said positions, eight or more of said positions, or nine or more of said positions.

In another embodiment, the number of alterations is 2-20, e.g., 2-10 and 2-5, such as 2, 3, 4, 5, 6, 7, 8, 9 or 10 alterations.

In another embodiment, the variant has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, but less than 100%, sequence identity to the amino acid sequence of SEQ ID NO: 1.

In another embodiment, the variant has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, but less than 100%, sequence identity, to the amino acid sequence of SEQ ID NO: 2.

In another embodiment, the variant has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, but less than 100%, sequence identity, to the amino acid sequence of SEQ ID NO: 3.

In another embodiment, the variant has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, but less than 100%, sequence identity, to the amino acid sequence of SEQ ID NO: 4.

In another embodiment, the variant has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, but less than 100%, sequence identity, to the amino acid sequence of SEQ ID NO: 5.

In another embodiment, the variant has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, but less than 100%, sequence identity, to the amino acid sequence of SEQ ID NO: 6.

In another embodiment, the variant has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, but less than 100%, sequence identity, to the amino acid sequence of SEQ ID NO: 7.

In another embodiment, the variant has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, but less than 100%, sequence identity, to the amino acid sequence of SEQ ID NO: 8.

a. In a preferred embodiment the variant is a variant of a parent alpha-amylase selected from the group consisting of: a. a polypeptide having at least 80% sequence identity to the mature polypeptide of SEQ ID NO: 1; b. a polypeptide having at least 80% sequence identity to the mature polypeptide of SEQ ID NO: 2; c. a fragment of the mature polypeptide of SEQ ID NO: 1, which has alpha-amylase activity; d. a fragment of the mature polypeptide of SEQ ID NO: 2, which has alpha-amylase activity; e. a polypeptide having immunological cross reactivity with an antibody raised against the mature polypeptide of SEQ ID NO: 1; f.

a polypeptide having immunological cross reactivity with an antibody raised against the mature polypeptide of SEQ ID NO: 2; g. polypeptide encoded by a polynucleotide that hybridizes under medium-high stringency conditions with (i) the mature polypeptide coding sequence of SEQ ID NO: 11, or (ii) the full-length complement thereof; h. a polypeptide encoded by a polynucleotide having at least 80% sequence identity to the mature polypeptide coding sequence of SEQ ID NO: 11.

In one embodiment, the parent alpha-amylase has at least 85%, such as at least 86%, at least 87%, at least 88%, at least 89%, at least 90%, at least 91%, at least 92%, at least 93%, at least 94%, at least 95% identity, at least 96%, at least 97%, at least 98%, or at least 99% sequence identity to SEQ ID NO: 1.

In another embodiment, the parent alpha-amylase has at least 85%, such as at least 86%, at least 87%, at least 88%, at least 89%, at least 90%, at least 91%, at least 92%, at least 93%, at least 94%, at least 95% identity, at least 96%, at least 97%, at least 98%, or at least 99% sequence identity to SEQ ID NO: 2.

In one embodiment, the parent alpha-amylase comprises or consists of the mature polypeptide of SEQ ID NO: 1.

In another embodiment, the parent alpha-amylase comprises or consists of the mature polypeptide of SEQ ID NO: 2.

In a preferred embodiment, the variant has an improved property relative to the parent, wherein the improved property is selected from the group consisting of catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity, thermo stability, and preferably improved washing performance at low temperature.

In a particularly preferred embodiment, the variant has improved detergent stability compared to the parent alpha-amylase.

In another embodiment, the variant has improved storage stability in liquid detergents relative to the alpha-amylase of SEQ ID NO: 1 or 2. The improved storage stability may be determined as residual activity after a storage period of 1 to 8 weeks, such as from 2-6 weeks, preferably 2, 3, 4, 5 or 6 weeks.

In one embodiment, the variant comprises the substitution L205Y of the mature polypeptide of SEQ ID NO: 1.

In another embodiment, the variant comprises the substitution L205Y of the mature polypeptide of SEQ ID NO: 2.

In one embodiment, the variant comprises the substitution L205F of the mature polypeptide of SEQ ID NO: 1.

In another embodiment, the variant comprises the substitution L205F of the mature polypeptide of SEQ ID NO: 2.

In one embodiment, the variant comprises the substitution N194F of the mature polypeptide of SEQ ID NO: 1.

In another embodiment, the variant comprises the substitution N194F of the mature polypeptide of SEQ ID NO: 2.

In one embodiment, the variant comprises the substitution N194Y of the mature polypeptide of SEQ ID NO: 1.

In another embodiment, the variant comprises the substitution N194Y of the mature polypeptide of SEQ ID NO: 2.

In one embodiment, the variant comprises the substitution Y48W of the mature polypeptide of SEQ ID NO: 1.

In another embodiment, the variant comprises the substitution Y48W of the mature polypeptide of SEQ ID NO: 2.

In one embodiment, the variant comprises the substitution R309Q of the mature polypeptide of SEQ ID NO: 1.

In another embodiment, the variant comprises the substitution R309Q of the mature polypeptide of SEQ ID NO: 2.

In one embodiment, the variant comprises the substitution M317L of the mature polypeptide of SEQ ID NO: 1.

In another embodiment, the variant comprises the substitution M317L of the mature polypeptide of SEQ ID NO: 2.

In one embodiment, the variant comprises the substitution I390E of the mature polypeptide of SEQ ID NO: 1.

In another embodiment, the variant comprises the substitution I390E of the mature polypeptide of SEQ ID NO: 2.

In one embodiment, the variant comprises the insertion N174NN of the mature polypeptide of SEQ ID NO: 1.

In another embodiment, the variant comprises the insertion N174NN of the mature polypeptide of SEQ ID NO: 2.

In one embodiment, the variant comprises the insertion N174NQ of the mature polypeptide of SEQ ID NO: 1.

In another embodiment, the variant comprises the insertion N174NQ of the mature polypeptide of SEQ ID NO: 2.

In one embodiment, the variant comprises the insertion N174NL of the mature polypeptide of SEQ ID NO: 1.

In another embodiment, the variant comprises the insertion N174NL of the mature polypeptide of SEQ ID NO: 2.

In one embodiment, the variant comprises the insertion N174NA of the mature polypeptide of SEQ ID NO: 1.

In another embodiment, the variant comprises the insertion N174NA of the mature polypeptide of SEQ ID NO: 2.

In one embodiment, the variant comprises the insertion N174NS of the mature polypeptide of SEQ ID NO: 1.

In another embodiment, the variant comprises the insertion N174NS of the mature polypeptide of SEQ ID NO: 2.

In one embodiment, the variant comprises the insertion E169EQ of the mature polypeptide of SEQ ID NO: 1.

In another embodiment, the variant comprises the insertion E169EQ of the mature polypeptide of SEQ ID NO: 2.

In one embodiment, the variant comprises the insertion L173LA of the mature polypeptide of SEQ ID NO: 1.

In another embodiment, the variant comprises the insertion L173LA of the mature polypeptide of SEQ ID NO: 2.

In one embodiment, the variant comprises the substitution K178L of the mature polypeptide of SEQ ID NO: 1.

In another embodiment, the variant comprises the substitution K178L of the mature polypeptide of SEQ ID NO: 2.

In one embodiment, the variant comprises the substitution E189P of the mature polypeptide of SEQ ID NO: 1.

In another embodiment, the variant comprises the substitution E189P of the mature polypeptide of SEQ ID NO: 2.

In one embodiment, the variant comprises the deletion R180*+S181* of the mature polypeptide of SEQ ID NO: 1.

In another embodiment, the variant comprises the deletion R180*+S181* of the mature polypeptide of SEQ ID NO: 2.

In one embodiment, the variant comprises the deletion R180*+T182* of the mature polypeptide of SEQ ID NO: 1.

In another embodiment, the variant comprises the deletion R180*+T182* of the mature polypeptide of SEQ ID NO: 2.

In one embodiment, the variant comprises the deletion R180*+G183* of the mature polypeptide of SEQ ID NO: 1.

In another embodiment, the variant comprises the deletion R180*+G183* of the mature polypeptide of SEQ ID NO: 2.

In one embodiment, the variant comprises the deletion S181*+T182* of the mature polypeptide of SEQ ID NO: 1.

In another embodiment, the variant comprises the deletion S181*+T182* of the mature polypeptide of SEQ ID NO: 2.

In one embodiment, the variant comprises the deletion T182*+G183* of the mature polypeptide of SEQ ID NO: 1.

In another embodiment, the variant comprises the deletion T182*+G183* of the mature polypeptide of SEQ ID NO: 2.

In one embodiment, the variant comprises or consists of the substitution L205Y and the deletion R180*+S181* of the mature polypeptide of SEQ ID NO: 1.

In one embodiment, the variant comprises or consists of the substitution L205Y and the deletion R180*+T182* of the mature polypeptide of SEQ ID NO: 1.

In one embodiment, the variant comprises or consists of the substitution L205Y and the deletion R180*+G183* of the mature polypeptide of SEQ ID NO: 1.

In one embodiment, the variant comprises or consists of the substitution L205Y and the deletion S181*+T182* of the mature polypeptide of SEQ ID NO: 1.

In one embodiment, the variant comprises or consists of the substitution L205Y and the deletion T182*+G183* of the mature polypeptide of SEQ ID NO: 1.

In one embodiment, the variant comprises or consists of the substitution L205F and the deletion R180*+S181* of the mature polypeptide of SEQ ID NO: 1.

In one embodiment, the variant comprises or consists of the substitution L205F and the deletion R180*+T182* of the mature polypeptide of SEQ ID NO: 1.

In one embodiment, the variant comprises or consists of the substitution L205F and the deletion R180*+G183* of the mature polypeptide of SEQ ID NO: 1.

In one embodiment, the variant comprises or consists of the substitution L205F and the deletion S181*+T182* of the mature polypeptide of SEQ ID NO: 1.

In one embodiment, the variant comprises or consists of the substitution L205F and the deletion T182*+G183* of the mature polypeptide of SEQ ID NO: 1.

In one embodiment, the variant comprises or consists of the substitution N194F and the deletion R180*+S181* of the mature polypeptide of SEQ ID NO: 1.

In one embodiment, the variant comprises or consists of the substitution N194F and the deletion R180*+T182* of the mature polypeptide of SEQ ID NO: 1.

In one embodiment, the variant comprises or consists of the substitution N194F and the deletion R180*+G183* of the mature polypeptide of SEQ ID NO: 1.

In one embodiment, the variant comprises or consists of the substitution N194F and the deletion S181*+T182* of the mature polypeptide of SEQ ID NO: 1.

In one embodiment, the variant comprises or consists of the substitution N194F and the deletion T182*+G183* of the mature polypeptide of SEQ ID NO: 1.

In one embodiment, the variant comprises or consists of the substitution N194Y and the deletion R180*+S181* of the mature polypeptide of SEQ ID NO: 1.

In one embodiment, the variant comprises or consists of the substitution N194Y and the deletion R180*+T182* of the mature polypeptide of SEQ ID NO: 1.

In one embodiment, the variant comprises or consists of the substitution N194Y and the deletion R180*+G183* of the mature polypeptide of SEQ ID NO: 1.

In one embodiment, the variant comprises or consists of the substitution N194Y and the deletion S181*+T182* of the mature polypeptide of SEQ ID NO: 1.

In one embodiment, the variant comprises or consists of the substitution N194Y and the deletion T182*+G183* of the mature polypeptide of SEQ ID NO: 1.

In one embodiment, the variant comprises or consists of the substitution Y48W and the deletion R180*+S181* of the mature polypeptide of SEQ ID NO: 1.

In one embodiment, the variant comprises or consists of the substitution Y48W and the deletion R180*+T182* of the mature polypeptide of SEQ ID NO: 1.

In one embodiment, the variant comprises or consists of the substitution Y48W and the deletion R180*+G183* of the mature polypeptide of SEQ ID NO: 1.

In one embodiment, the variant comprises or consists of the substitution Y48W and the deletion S181*+T182* of the mature polypeptide of SEQ ID NO: 1.

In one embodiment, the variant comprises or consists of the substitution Y48W and the deletion T182*+G183* of the mature polypeptide of SEQ ID NO: 1.

In one embodiment, the variant comprises or consists of the substitution R309Q and the deletion R180*+S181* of the mature polypeptide of SEQ ID NO: 1.

In one embodiment, the variant comprises or consists of the substitution R309Q and the deletion R180*+T182* of the mature polypeptide of SEQ ID NO: 1.

In one embodiment, the variant comprises or consists of the substitution R309Q and the deletion R180*+G183* of the mature polypeptide of SEQ ID NO: 1.

In one embodiment, the variant comprises or consists of the substitution R309Q and the deletion S181*+T182* of the mature polypeptide of SEQ ID NO: 1.

In one embodiment, the variant comprises or consists of the substitution R309Q and the deletion T182*+G183* of the mature polypeptide of SEQ ID NO: 1.

In one embodiment, the variant comprises or consists of the substitution M317L and the deletion R180*+S181* of the mature polypeptide of SEQ ID NO: 1.

In one embodiment, the variant comprises or consists of the substitution M317L and the deletion R180*+T182* of the mature polypeptide of SEQ ID NO: 1.

In one embodiment, the variant comprises or consists of the substitution M317L and the deletion R180*+G183* of the mature polypeptide of SEQ ID NO: 1.

In one embodiment, the variant comprises or consists of the substitution M317L and the deletion S181*+T182* of the mature polypeptide of SEQ ID NO: 1.

In one embodiment, the variant comprises or consists of the substitution M317L and the deletion T182*+G183* of the mature polypeptide of SEQ ID NO: 1.

In one embodiment, the variant comprises or consists of the substitution I390E and the deletion R180*+S181* of the mature polypeptide of SEQ ID NO: 1.

In one embodiment, the variant comprises or consists of the substitution I390E and the deletion R180*+T182* of the mature polypeptide of SEQ ID NO: 1.

In one embodiment, the variant comprises or consists of the substitution I390E and the deletion R180*+G183* of the mature polypeptide of SEQ ID NO: 1.

In one embodiment, the variant comprises or consists of the substitution I390E and the deletion S181*+T182* of the mature polypeptide of SEQ ID NO: 1.

In one embodiment, the variant comprises or consists of the substitution I390E and the deletion T182*+G183* of the mature polypeptide of SEQ ID NO: 1.

In one embodiment, the variant comprises or consists of the insertion N174NN and the deletion R180*+S181* of the mature polypeptide of SEQ ID NO: 1.

In one embodiment, the variant comprises or consists of the insertion N174NN and the deletion R180*+T182* of the mature polypeptide of SEQ ID NO: 1.

In one embodiment, the variant comprises or consists of the insertion N174NN and the deletion R180*+G183* of the mature polypeptide of SEQ ID NO: 1.

In one embodiment, the variant comprises or consists of the insertion N174NN and the deletion S181*+T182* of the mature polypeptide of SEQ ID NO: 1.

In one embodiment, the variant comprises or consists of the insertion N174NN and the deletion T182*+G183* of the mature polypeptide of SEQ ID NO: 1.

In one embodiment, the variant comprises or consists of the insertion N174NQ and the deletion R180*+S181* of the mature polypeptide of SEQ ID NO: 1.

In one embodiment, the variant comprises or consists of the insertion N174NQ and the deletion R180*+T182* of the mature polypeptide of SEQ ID NO: 1.

In one embodiment, the variant comprises or consists of the insertion N174NQ and the deletion R180*+G183* of the mature polypeptide of SEQ ID NO: 1.

In one embodiment, the variant comprises or consists of the insertion N174NQ and the deletion S181*+T182* of the mature polypeptide of SEQ ID NO: 1.

In one embodiment, the variant comprises or consists of the insertion N174NQ and the deletion T182*+G183* of the mature polypeptide of SEQ ID NO: 1.

In one embodiment, the variant comprises or consists of the substitution K178L and the deletion R180*+S181* of the mature polypeptide of SEQ ID NO: 1.

In one embodiment, the variant comprises or consists of the substitution K178L and the deletion R180*+T182* of the mature polypeptide of SEQ ID NO: 1.

In one embodiment, the variant comprises or consists of the substitution K178L and the deletion R180*+G183* of the mature polypeptide of SEQ ID NO: 1.

In one embodiment, the variant comprises or consists of the substitution K178L and the deletion S181*+T182* of the mature polypeptide of SEQ ID NO: 1.

In one embodiment, the variant comprises or consists of the substitution K178L and the deletion T182*+G183* of the mature polypeptide of SEQ ID NO: 1.

In one embodiment, the variant comprises or consists of the substitution E189P and the deletion R180*+S181* of the mature polypeptide of SEQ ID NO: 1.

In one embodiment, the variant comprises or consists of the substitution E189P and the deletion R180*+T182* of the mature polypeptide of SEQ ID NO: 1.

In one embodiment, the variant comprises or consists of the substitution E189P and the deletion R180*+G183* of the mature polypeptide of SEQ ID NO: 1.

In one embodiment, the variant comprises or consists of the substitution E189P and the deletion S181*+T182* of the mature polypeptide of SEQ ID NO: 1.

In one embodiment, the variant comprises or consists of the substitution E189P and the deletion T182*+G183* of the mature polypeptide of SEQ ID NO: 1.

In one embodiment, the variant comprises or consists of the substitution L205Y and the deletion R180*+S181* of the mature polypeptide of SEQ ID NO: 2.

In one embodiment, the variant comprises or consists of the substitution L205Y and the deletion R180*+T182* of the mature polypeptide of SEQ ID NO: 2.

In one embodiment, the variant comprises or consists of the substitution L205Y and the deletion R180*+G183* of the mature polypeptide of SEQ ID NO: 2.

In one embodiment, the variant comprises or consists of the substitution L205Y and the deletion S181*+T182* of the mature polypeptide of SEQ ID NO: 2.

In one embodiment, the variant comprises or consists of the substitution L205Y and the deletion T182*+G183* of the mature polypeptide of SEQ ID NO: 2.

In one embodiment, the variant comprises or consists of the substitution L205F and the deletion R180*+S181* of the mature polypeptide of SEQ ID NO: 2.

In one embodiment, the variant comprises or consists of the substitution L205F and the deletion R180*+T182* of the mature polypeptide of SEQ ID NO: 2.

In one embodiment, the variant comprises or consists of the substitution L205F and the deletion R180*+G183* of the mature polypeptide of SEQ ID NO: 2.

In one embodiment, the variant comprises or consists of the substitution L205F and the deletion S181*+T182* of the mature polypeptide of SEQ ID NO: 2.

In one embodiment, the variant comprises or consists of the substitution L205F and the deletion T182*+G183* of the mature polypeptide of SEQ ID NO: 2.

In one embodiment, the variant comprises or consists of the substitution N194F and the deletion R180*+S181* of the mature polypeptide of SEQ ID NO: 2.

In one embodiment, the variant comprises or consists of the substitution N194F and the deletion R180*+T182* of the mature polypeptide of SEQ ID NO: 2.

In one embodiment, the variant comprises or consists of the substitution N194F and the deletion R180*+G183* of the mature polypeptide of SEQ ID NO: 2.

In one embodiment, the variant comprises or consists of the substitution N194F and the deletion S181*+T182* of the mature polypeptide of SEQ ID NO: 2.

In one embodiment, the variant comprises or consists of the substitution N194F and the deletion T182*+G183* of the mature polypeptide of SEQ ID NO: 2.

In one embodiment, the variant comprises or consists of the substitution N194Y and the deletion R180*+S181* of the mature polypeptide of SEQ ID NO: 2.

In one embodiment, the variant comprises or consists of the substitution N194Y and the deletion R180*+T182* of the mature polypeptide of SEQ ID NO: 2.

In one embodiment, the variant comprises or consists of the substitution N194Y and the deletion R180*+G183* of the mature polypeptide of SEQ ID NO: 2.

In one embodiment, the variant comprises or consists of the substitution N194Y and the deletion S181*+T182* of the mature polypeptide of SEQ ID NO: 2.

In one embodiment, the variant comprises or consists of the substitution N194Y and the deletion T182*+G183* of the mature polypeptide of SEQ ID NO: 2.

In one embodiment, the variant comprises or consists of the substitution Y48W and the deletion R180*+S181* of the mature polypeptide of SEQ ID NO: 2.

In one embodiment, the variant comprises or consists of the substitution Y48W and the deletion R180*+T182* of the mature polypeptide of SEQ ID NO: 2.

In one embodiment, the variant comprises or consists of the substitution Y48W and the deletion R180*+G183* of the mature polypeptide of SEQ ID NO: 2.

In one embodiment, the variant comprises or consists of the substitution Y48W and the deletion S181*+T182* of the mature polypeptide of SEQ ID NO: 2.

In one embodiment, the variant comprises or consists of the substitution Y48W and the deletion T182*+G183* of the mature polypeptide of SEQ ID NO: 2.

In one embodiment, the variant comprises or consists of the substitution R309Q and the deletion R180*+S181* of the mature polypeptide of SEQ ID NO: 2.

In one embodiment, the variant comprises or consists of the substitution R309Q and the deletion R180*+T182* of the mature polypeptide of SEQ ID NO: 2.

In one embodiment, the variant comprises or consists of the substitution R309Q and the deletion R180*+G183* of the mature polypeptide of SEQ ID NO: 2.

In one embodiment, the variant comprises or consists of the substitution R309Q and the deletion S181*+T182* of the mature polypeptide of SEQ ID NO: 2.

In one embodiment, the variant comprises or consists of the substitution R309Q and the deletion T182*+G183* of the mature polypeptide of SEQ ID NO: 2.

In one embodiment, the variant comprises or consists of the substitution M317L and the deletion R180*+S181* of the mature polypeptide of SEQ ID NO: 2.

In one embodiment, the variant comprises or consists of the substitution M317L and the deletion R180*+T182* of the mature polypeptide of SEQ ID NO: 2.

In one embodiment, the variant comprises or consists of the substitution M317L and the deletion R180*+G183* of the mature polypeptide of SEQ ID NO: 2.

In one embodiment, the variant comprises or consists of the substitution M317L and the deletion S181*+T182* of the mature polypeptide of SEQ ID NO: 2.

In one embodiment, the variant comprises or consists of the substitution M317L and the deletion T182*+G183* of the mature polypeptide of SEQ ID NO: 2.

In one embodiment, the variant comprises or consists of the substitution I390E and the deletion R180*+S181* of the mature polypeptide of SEQ ID NO: 2.

In one embodiment, the variant comprises or consists of the substitution I390E and the deletion R180*+T182* of the mature polypeptide of SEQ ID NO: 2.

In one embodiment, the variant comprises or consists of the substitution I390E and the deletion R180*+G183* of the mature polypeptide of SEQ ID NO: 2.

In one embodiment, the variant comprises or consists of the substitution I390E and the deletion S181*+T182* of the mature polypeptide of SEQ ID NO: 2.

In one embodiment, the variant comprises or consists of the substitution I390E and the deletion T182*+G183* of the mature polypeptide of SEQ ID NO: 2.

In one embodiment, the variant comprises or consists of the insertion N174NN and the deletion R180*+S181* of the mature polypeptide of SEQ ID NO: 2.

In one embodiment, the variant comprises or consists of the insertion N174NN and the deletion R180*+T182* of the mature polypeptide of SEQ ID NO: 2.

In one embodiment, the variant comprises or consists of the insertion N174NN and the deletion R180*+G183* of the mature polypeptide of SEQ ID NO: 2.

In one embodiment, the variant comprises or consists of the insertion N174NN and the deletion S181*+T182* of the mature polypeptide of SEQ ID NO: 2.

In one embodiment, the variant comprises or consists of the insertion N174NN and the deletion T182*+G183* of the mature polypeptide of SEQ ID NO: 2.

In one embodiment, the variant comprises or consists of the insertion N174NQ and the deletion R180*+S181* of the mature polypeptide of SEQ ID NO: 2.

In one embodiment, the variant comprises or consists of the insertion N174NQ and the deletion R180*+T182* of the mature polypeptide of SEQ ID NO: 2.

In one embodiment, the variant comprises or consists of the insertion N174NQ and the deletion R180*+G183* of the mature polypeptide of SEQ ID NO: 2.

In one embodiment, the variant comprises or consists of the insertion N174NQ and the deletion S181*+T182* of the mature polypeptide of SEQ ID NO: 2.

In one embodiment, the variant comprises or consists of the insertion N174NQ and the deletion T182*+G183* of the mature polypeptide of SEQ ID NO: 2.

In one embodiment, the variant comprises or consists of the substitution K178L and the deletion R180*+S181* of the mature polypeptide of SEQ ID NO: 2.

In one embodiment, the variant comprises or consists of the substitution K178L and the deletion R180*+T182* of the mature polypeptide of SEQ ID NO: 2.

In one embodiment, the variant comprises or consists of the substitution K178L and the deletion R180*+G183* of the mature polypeptide of SEQ ID NO: 2.

In one embodiment, the variant comprises or consists of the substitution K178L and the deletion S181*+T182* of the mature polypeptide of SEQ ID NO: 2.

In one embodiment, the variant comprises or consists of the substitution K178L and the deletion T182*+G183* of the mature polypeptide of SEQ ID NO: 2.

In one embodiment, the variant comprises or consists of the substitution E189P and the deletion R180*+S181* of the mature polypeptide of SEQ ID NO: 2.

In one embodiment, the variant comprises or consists of the substitution E189P and the deletion R180*+T182* of the mature polypeptide of SEQ ID NO: 2.

In one embodiment, the variant comprises or consists of the substitution E189P and the deletion R180*+G183* of the mature polypeptide of SEQ ID NO: 2.

In one embodiment, the variant comprises or consists of the substitution E189P and the deletion S181*+T182* of the mature polypeptide of SEQ ID NO: 2.

In one embodiment, the variant comprises or consists of the substitution E189P and the deletion T182*+G183* of the mature polypeptide of SEQ ID NO: 2.

In one embodiment, the variant comprises multiple alterations of the mature polypeptide of SEQ ID NO: 1 or 2 selected from the list consisting of D16Y+R180*+S181*, D16Y+R180*+T182*, D16Y+R180*+G183*, D16Y+S181*+T182*, D16Y+T182*+G183*, D16Y+N194F+R180*+S181*, D16Y+N194F+R180*+T182*, D16Y+N194F+R180*+G183*, D16Y+N194F+S181*+T182*, D16Y+N194F+T182*+G183*, D16Y+N194Y+R180*+S181*, D16Y+N194Y+R180*+T182*, D16Y+N194Y+R180*+G183*, D16Y+N194Y+S181*+T182*, D16Y+N194Y+T182*+G183* and D16Y+G475K+S243Q+R180*+S181*.

In one embodiment, the variant comprises multiple alterations of the mature polypeptide of SEQ ID NO: 1 or 2 selected from the list consisting of N19D+R180*+S181*, N19D+R180*+T182*, N19D+R180*+G183*, N19D+S181*+T182*, N19D+T182*+G183*, N19D+N194F+R180*+S181*, N19D+N194F+R180*+T182*, N19D+N194F+R180*+G183*, N19D+N194F+S181*+T182*, N19D+N194F+T182*+G183*, N19D+N194Y+R180*+S181*, N19D+N194Y+R180*+T182*, N19D+N194Y+R180*+G183*, N19D+N194Y+S181*+T182*, N19D+N194Y+T182*+G183* and N19D+G475K+S243Q+R180*+S181*.

In one embodiment, the variant comprises multiple alterations of the mature polypeptide of SEQ ID NO: 1 or 2 selected from the list consisting of Y48W+R180*+S181*, Y48W+R180*+T182*, Y48W+R180*+G183*, Y48W+S181*+T182*, Y48W+T182*+G183*, Y48W+N194F+R180*+S181*, Y48W+N194F+R180*+T182*, Y48W+N194F+R180*+G183*, Y48W+N194F+S181*+T182*, Y48W+N194F+T182*+G183*, Y48W+N194Y+R180*+S181*, Y48W+N194Y+R180*+T182*, Y48W+N194Y+R180*+G183*, Y48W+N194Y+S181*+T182*, Y48W+N194Y+T182*+G183* and Y48W+G475K+S243Q+R180*+S181*.

In one embodiment, the variant comprises multiple alterations of the mature polypeptide of SEQ ID NO: 1 or 2 selected from the list consisting of Y48F+R180*+S181*, Y48F+R180*+T182*, Y48F+R180*+G183*, Y48F+S181*+T182*, Y48F+T182*+G183*, Y48F+N194F+R180*+S181*, Y48F+N194F+R180*+T182*, Y48F+N194F+R180*+G183*, Y48F+N194F+S181*+T182*, Y48F+N194F+T182*+G183*, Y48F+N194Y+R180*+S181*, Y48F+N194Y+R180*+T182*, Y48F+N194Y+R180*+G183*, Y48F+N194Y+S181*+T182*, Y48F+N194Y+T182*+G183* and Y48F+G475K+S243Q+R180*+S181*.

In one embodiment, the variant comprises multiple alterations of the mature polypeptide of SEQ ID NO: 1 or 2 selected from the list consisting of Q53R+R180*+S181*, Q53R+R180*+T182*, Q53R+R180*+G183*, Q53R+S181*+T182*, Q53R+T182*+G183*, Q53R+N194F+R180*+S181*, Q53R+N194F+R180*+T182*, Q53R+N194F+R180*+G183*, Q53R+N194F+S181*+T182*, Q53R+N194F+T182*+G183*, Q53R+N194Y+R180*+S181*, Q53R+N194Y+R180*+T182*, Q53R+N194Y+R180*+G183*, Q53R+N194Y+S181*+T182*, Q53R+N194Y+T182*+G183* and Q53R+G475K+S243Q+R180*+S181*.

In one embodiment, the variant comprises multiple alterations of the mature polypeptide of SEQ ID NO: 1 or 2 selected from the list consisting of V60A+R180*+S181*, V60A+R180*+T182*, V60A+R180*+G183*, V60A+S181*+T182*, V60A+T182*+G183*, V60A+N194F+R180*+S181*, V60A+N194F+R180*+T182*, V60A+N194F+R180*+G183*, V60A+N194F+S181*+T182*, V60A+N194F+T182*+G183*, V60A+N194Y+R180*+S181*, V60A+N194Y+R180*+T182*, V60A+N194Y+R180*+G183*, V60A+N194Y+S181*+T182*, V60A+N194Y+T182*+G183* and V60A+G475K+S243Q+R180*+S181*.

In one embodiment, the variant comprises multiple alterations of the mature polypeptide of SEQ ID NO: 1 or 2 selected from the list consisting of F105M+R180*+S181*, F105M+R180*+T182*, F105M+R180*+G183*, F105M+S181*+T182*, F105M+T182*+G183*, F105M+N194F+R180*+S181*, F105M+N194F+R180*+T182*, F105M+N194F+R180*+G183*, F105M+N194F+S181*+T182*, F105M+N194F+T182*+G183*, F105M+N194Y+R180*+S181*, F105M+N194Y+R180*+T182*, F105M+N194Y+R180*+G183*, F105M+N194Y+S181*+T182*, F105M+N194Y+T182*+G183* and F105M+G475K+S243Q+R180*+S181*.

In one embodiment, the variant comprises multiple alterations of the mature polypeptide of SEQ ID NO: 1 or 2 selected from the list consisting of F116W+R180*+S181*, F116W+R180*+T182*, F116W+R180*+G183*, F116W+S181*+T182*, F116W+T182*+G183*, F116W+N194F+R180*+S181*, F116W+N194F+R180*+T182*, F116W+N194F+R180*+G183*, F116W+N194F+S181*+T182*, F116W+N194F+T182*+G183*, F116W+N194Y+R180*+S181*, F116W+N194Y+R180*+T182*, F116W+N194Y+R180*+G183*, F116W+N194Y+S181*+T182*, F116W+N194Y+T182*+G183* and F116W+G475K+S243Q+R180*+S181*.

In one embodiment, the variant comprises multiple alterations of the mature polypeptide of SEQ ID NO: 1 or 2 selected from the list consisting of P124*+R180*+S181*, P124*+R180*+T182*, P124*+R180*+G183*, P124*+

S181*+T182*, P124*+T182*+G183*, P124*+N194F+R180*+S181*, P124*+N194F+R180*+T182*, P124*+N194F+R180*+G183*, P124*+N194F+S181*+T182*, P124*+N194F+T182*+G183*, P124*+N194Y+R180*+S181*, P124*+N194Y+R180*+T182*, P124*+N194Y+R180*+G183*, P124*+N194Y+S181*+T182*, P124*+N194Y+T182*+G183* and P124*+G475K+S243Q+R180*+S181*.

In one embodiment, the variant comprises multiple alterations of the mature polypeptide of SEQ ID NO: 1 or 2 selected from the list consisting of P124D+R180*+S181*, P124D+R180*+T182*, P124D+R180*+G183*, P124D+S181*+T182*, P124D+T182*+G183*, P124D+N194F+R180*+S181*, P124D+N194F+R180*+T182*, P124D+N194F+R180*+G183*, P124D+N194F+S181*+T182*, P124D+N194F+T182*+G183*, P124D+N194Y+R180*+S181*, P124D+N194Y+R180*+T182*, P124D+N194Y+R180*+G183*, P124D+N194Y+S181*+T182*, P124D+N194Y+T182*+G183* and P124D+G475K+S243Q+R180*+S181*.

In one embodiment, the variant comprises multiple alterations of the mature polypeptide of SEQ ID NO: 1 or 2 selected from the list consisting of P124S+R180*+S181*, P124S+R180*+T182*, P124S+R180*+G183*, P124S+S181*+T182*, P124S+T182*+G183*, P124S+N194F+R180*+S181*, P124S+N194F+R180*+T182*, P124S+N194F+R180*+G183*, P124S+N194F+S181*+T182*, P124S+N194F+T182*+G183*, P124S+N194Y+R180*+S181*, P124S+N194Y+R180*+T182*, P124S+N194Y+R180*+G183*, P124S+N194Y+S181*+T182*, P124S+N194Y+T182*+G183* and P124S+G475K+S243Q+R180*+S181*.

In one embodiment, the variant comprises multiple alterations of the mature polypeptide of SEQ ID NO: 1 or 2 selected from the list consisting of P124T+R180*+S181*, P124T+R180*+T182*, P124T+R180*+G183*, P124T+S181*+T182*, P124T+T182*+G183*, P124T+N194F+R180*+S181*, P124T+N194F+R180*+T182*, P124T+N194F+R180*+G183*, P124T+N194F+S181*+T182*, P124T+N194F+T182*+G183*, P124T+N194Y+R180*+S181*, P124T+N194Y+R180*+T182*, P124T+N194Y+R180*+G183*, P124T+N194Y+S181*+T182*, P124T+N194Y+T182*+G183* and P124T+G475K+S243Q+R180*+S181*.

In one embodiment, the variant comprises multiple alterations of the mature polypeptide of SEQ ID NO: 1 or 2 selected from the list consisting of S125N+R180*+S181*, S125N+R180*+T182*, S125N+R180*+G183*, S125N+S181*+T182*, S125N+T182*+G183*, S125N+N194F+R180*+S181*, S125N+N194F+R180*+T182*, S125N+N194F+R180*+G183*, S125N+N194F+S181*+T182*, S125N+N194F+T182*+G183*, S125N+N194Y+R180*+S181*, S125N+N194Y+R180*+T182*, S125N+N194Y+R180*+G183*, S125N+N194Y+S181*+T182*, S125N+N194Y+T182*+G183* and S125N+G475K+S243Q+R180*+S181*.

In one embodiment, the variant comprises multiple alterations of the mature polypeptide of SEQ ID NO: 1 or 2 selected from the list consisting of S125P+R180*+S181*, S125P+R180*+T182*, S125P+R180*+G183*, S125P+S181*+T182*, S125P+T182*+G183*, S125P+N194F+R180*+S181*, S125P+N194F+R180*+T182*, S125P+N194F+R180*+G183*, S125P+N194F+S181*+T182*, S125P+N194F+T182*+G183*, S125P+N194Y+R180*+S181*, S125P+N194Y+R180*+T182*, S125P+N194Y+R180*+G183*, S125P+N194Y+S181*+T182*, S125P+N194Y+T182*+G183* and S125P+G475K+S243Q+R180*+S181*.

In one embodiment, the variant comprises multiple alterations of the mature polypeptide of SEQ ID NO: 1 or 2 selected from the list consisting of N128F+R180*+S181*, N128F+R180*+T182*, N128F+R180*+G183*, N128F+S181*+T182*, N128F+T182*+G183*, N128F+N194F+R180*+S181*, N128F+N194F+R180*+T182*, N128F+N194F+R180*+G183*, N128F+N194F+S181*+T182*, N128F+N194F+T182*+G183*, N128F+N194Y+R180*+S181*, N128F+N194Y+R180*+T182*, N128F+N194Y+R180*+G183*, N128F+N194Y+S181*+T182*, N128F+N194Y+T182*+G183* and N128F+G475K+S243Q+R180*+S181*.

In one embodiment, the variant comprises multiple alterations of the mature polypeptide of SEQ ID NO: 1 or 2 selected from the list consisting of N128H+R180*+S181*, N128H+R180*+T182*, N128H+R180*+G183*, N128H+S181*+T182*, N128H+T182*+G183*, N128H+N194F+R180*+S181*, N128H+N194F+R180*+T182*, N128H+N194F+R180*+G183*, N128H+N194F+S181*+T182*, N128H+N194F+T182*+G183*, N128H+N194Y+R180*+S181*, N128H+N194Y+R180*+T182*, N128H+N194Y+R180*+G183*, N128H+N194Y+S181*+T182*, N128H+N194Y+T182*+G183* and N128H+G475K+S243Q+R180*+S181*.

In one embodiment, the variant comprises multiple alterations of the mature polypeptide of SEQ ID NO: 1 or 2 selected from the list consisting of N128I+R180*+S181*, N128I+R180*+T182*, N128I+R180*+G183*, N128I+S181*+T182*, N128I+T182*+G183*, N128I+N194F+R180*+S181*, N128I+N194F+R180*+T182*, N128I+N194F+R180*+G183*, N128I+N194F+S181*+T182*, N128I+N194F+T182*+G183*, N128I+N194Y+R180*+S181*, N128I+N194Y+R180*+T182*, N128I+N194Y+R180*+G183*, N128I+N194Y+S181*+T182*, N128I+N194Y+T182*+G183* and N128I+G475K+S243Q+R180*+S181*.

In one embodiment, the variant comprises multiple alterations of the mature polypeptide of SEQ ID NO: 1 or 2 selected from the list consisting of N128K+R180*+S181*, N128K+R180*+T182*, N128K+R180*+G183*, N128K+S181*+T182*, N128K+T182*+G183*, N128K+N194F+R180*+S181*, N128K+N194F+R180*+T182*, N128K+N194F+R180*+G183*, N128K+N194F+S181*+T182*, N128K+N194F+T182*+G183*, N128K+N194Y+R180*+S181*, N128K+N194Y+R180*+T182*, N128K+N194Y+R180*+G183*, N128K+N194Y+S181*+T182*, N128K+N194Y+T182*+G183* and N128K+G475K+S243Q+R180*+S181*.

In one embodiment, the variant comprises multiple alterations of the mature polypeptide of SEQ ID NO: 1 or 2 selected from the list consisting of N128R+R180*+S181*, N128R+R180*+T182*, N128R+R180*+G183*, N128R+S181*+T182*, N128R+T182*+G183*, N128R+N194F+R180*+S181*, N128R+N194F+R180*+T182*, N128R+N194F+R180*+G183*, N128R+N194F+S181*+T182*, N128R+N194F+T182*+G183*, N128R+N194Y+R180*+S181*, N128R+N194Y+R180*+T182*, N128R+N194Y+R180*+G183*, N128R+N194Y+S181*+T182*, N128R+N194Y+T182*+G183* and N128R+G475K+S243Q+R180*+S181*.

In one embodiment, the variant comprises multiple alterations of the mature polypeptide of SEQ ID NO: 1 or 2 selected from the list consisting of T131D+R180*+S181*, T131D+R180*+T182*, T131D+R180*+G183*, T131D+

S181*+T182*, T131D+T182*+G183*, T131D+N194F+R180*+S181*, T131D+N194F+R180*+T182*, T131D+N194F+R180*+G183*, T131D+N194F+S181*+T182*, T131D+N194F+T182*+G183*, T131D+N194Y+R180*+S181*, T131D+N194Y+R180*+T182*, T131D+N194Y+R180*+G183*, T131D+N194Y+S181*+T182*, T131D+N194Y+T182*+G183* and T131D+G475K+S243Q+R180*+S181*.

In one embodiment, the variant comprises multiple alterations of the mature polypeptide of SEQ ID NO: 1 or 2 selected from the list consisting of T131E+R180*+S181*, T131E+R180*+T182*, T131E+R180*+G183*, T131E+S181*+T182*, T131E+T182*+G183*, T131E+N194F+R180*+S181*, T131E+N194F+R180*+T182*, T131E+N194F+R180*+G183*, T131E+N194F+S181*+T182*, T131E+N194F+T182*+G183*, T131E+N194Y+R180*+S181*, T131E+N194Y+R180*+T182*, T131E+N194Y+R180*+G183*, T131E+N194Y+S181*+T182*, T131E+N194Y+T182*+G183* and T131E+G475K+S243Q+R180*+S181*.

In one embodiment, the variant comprises multiple alterations of the mature polypeptide of SEQ ID NO: 1 or 2 selected from the list consisting of T131L+R180*+S181*, T131 L+R180*+T182*, T131 L+R180*+G183*, T131L+S181*+T182*, T131 L+T182*+G183*, T131L+N194F+R180*+S181*, T131L+N194F+R180*+T182*, T131L+N194F+R180*+G183*, T131L+N194F+S181*+T182*, T131L+N194F+T182*+G183*, T131L+N194Y+R180*+S181*, T131L+N194Y+R180*+T182*, T131L+N194Y+R180*+G183*, T131L+N194Y+S181*+T182*, T131L+N194Y+T182*+G183* and T131L+G475K+S243Q+R180*+S181*.

In one embodiment, the variant comprises multiple alterations of the mature polypeptide of SEQ ID NO: 1 or 2 selected from the list consisting of G133D+R180*+S181*, G133D+R180*+T182*, G133D+R180*+G183*, G133D+S181*+T182*, G133D+T182*+G183*, G133D+N194F+R180*+S181*, G133D+N194F+R180*+T182*, G133D+N194F+R180*+G183*, G133D+N194F+S181*+T182*, G133D+N194F+T182*+G183*, G133D+N194Y+R180*+S181*, G133D+N194Y+R180*+T182*, G133D+N194Y+R180*+G183*, G133D+N194Y+S181*+T182*, G133D+N194Y+T182*+G183* and G133D+G475K+S243Q+R180*+S181*.

In one embodiment, the variant comprises multiple alterations of the mature polypeptide of SEQ ID NO: 1 or 2 selected from the list consisting of K172Q+R180*+S181*, K172Q+R180*+T182*, K172Q+R180*+G183*, K172Q+S181*+T182*, K172Q+T182*+G183*, K172Q+N194F+R180*+S181*, K172Q+N194F+R180*+T182*, K172Q+N194F+R180*+G183*, K172Q+N194F+S181*+T182*, K172Q+N194F+T182*+G183*, K172Q+N194Y+R180*+S181*, K172Q+N194Y+R180*+T182*, K172Q+N194Y+R180*+G183*, K172Q+N194Y+S181*+T182*, K172Q+N194Y+T182*+G183* and K172Q+G475K+S243Q+R180*+S181*.

In one embodiment, the variant comprises multiple alterations of the mature polypeptide of SEQ ID NO: 1 or 2 selected from the list consisting of L173F+R180*+S181*, L173F+R180*+T182*, L173F+R180*+G183*, L173F+S181*+T182*, L173F+T182*+G183*, L173F+N194F+R180*+S181*, L173F+N194F+R180*+T182*, L173F+N194F+R180*+G183*, L173F+N194F+S181*+T182*, L173F+N194F+T182*+G183*, L173F+N194Y+R180*+S181*, L173F+N194Y+R180*+T182*, L173F+N194Y+R180*+G183*, L173F+N194Y+S181*+T182*, L173F+N194Y+T182*+G183* and L173F+G475K+S243Q+R180*+S181*.

In one embodiment, the variant comprises multiple alterations of the mature polypeptide of SEQ ID NO: 1 or 2 selected from the list consisting of L173Y+R180*+S181*, L173Y+R180*+T182*, L173Y+R180*+G183*, L173Y+S181*+T182*, L173Y+T182*+G183*, L173Y+N194F+R180*+S181*, L173Y+N194F+R180*+T182*, L173Y+N194F+R180*+G183*, L173Y+N194F+S181*+T182*, L173Y+N194F+T182*+G183*, L173Y+N194Y+R180*+S181*, L173Y+N194Y+R180*+T182*, L173Y+N194Y+R180*+G183*, L173Y+N194Y+S181*+T182*, L173Y+N194Y+T182*+G183* and L173Y+G475K+S243Q+R180*+S181*.

In one embodiment, the variant comprises multiple alterations of the mature polypeptide of SEQ ID NO: 1 or 2 selected from the list consisting of N174NQ+R180*+S181*, N174NQ+R180*+T182*, N174NQ+R180*+G183*, N174NQ+S181*+T182*, N174NQ+T182*+G183*, N174NQ+N194F+R180*+S181*, N174NQ+N194F+R180*+T182*, N174NQ+N194F+R180*+G183*, N174NQ+N194F+S181*+T182*, N174NQ+N194F+T182*+G183*, N174NQ+N194Y+R180*+S181*, N174NQ+N194Y+R180*+T182*, N174NQ+N194Y+R180*+G183*, N174NQ+N194Y+S181*+T182*, N174NQ+N194Y+T182*+G183* and N174NQ+G475K+S243Q+R180*+S181*.

In one embodiment, the variant comprises multiple alterations of the mature polypeptide of SEQ ID NO: 1 or 2 selected from the list consisting of N174NN+R180*+S181*, N174NN+R180*+T182*, N174NN+R180*+G183*, N174NN+S181*+T182*, N174NN+T182*+G183*, N174NN+N194F+R180*+S181*, N174NN+N194F+R180*+T182*, N174NN+N194F+R180*+G183*, N174NN+N194F+S181*+T182*, N174NN+N194F+T182*+G183*, N174NN+N194Y+R180*+S181*, N174NN+N194Y+R180*+T182*, N174NN+N194Y+R180*+G183*, N174NN+N194Y+S181*+T182*, N174NN+N194Y+T182*+G183* and N174NN+G475K+S243Q+R180*+S181*.

In one embodiment, the variant comprises multiple alterations of the mature polypeptide of SEQ ID NO: 1 or 2 selected from the list consisting of N174NE+R180*+S181*, N174NE+R180*+T182*, N174NE+R180*+G183*, N174NE+S181*+T182*, N174NE+T182*+G183*, N174NE+N194F+R180*+S181*, N174NE+N194F+R180*+T182*, N174NE+N194F+R180*+G183*, N174NE+N194F+S181*+T182*, N174NE+N194F+T182*+G183*, N174NE+N194Y+R180*+S181*, N174NE+N194Y+R180*+T182*, N174NE+N194Y+R180*+G183*, N174NE+N194Y+S181*+T182*, N174NE+N194Y+T182*+G183* and N174NE+G475K+S243Q+R180*+S181*.

In one embodiment, the variant comprises multiple alterations of the mature polypeptide of SEQ ID NO: 1 or 2 selected from the list consisting of N174ND+R180*+S181*, N174ND+R180*+T182*, N174ND+R180*+G183*, N174ND+S181*+T182*, N174ND+T182*+G183*, N174ND+N194F+R180*+S181*, N174ND+N194F+R180*+T182*, N174ND+N194F+R180*+G183*, N174ND+N194F+S181*+T182*, N174ND+N194F+T182*+G183*, N174ND+N194Y+R180*+S181*, N174ND+N194Y+R180*+T182*, N174ND+N194Y+R180*+G183*, N174ND+N194Y+S181*+T182*, N174ND+N194Y+T182*+G183* and N174ND+G475K+S243Q+R180*+S181*.

In one embodiment, the variant comprises multiple alterations of the mature polypeptide of SEQ ID NO: 1 or 2 selected from the list consisting of K178L+R180*+S181*, K178L+R180*+T182*, K178L+R180*+G183*, K178L+S181*+T182*, K178L+T182*+G183*, K178L+N194F+R180*+S181*, K178L+N194F+R180*+T182*, K178L+N194F+R180*+G183*, K178L+N194F+S181*+T182*, K178L+N194F+T182*+G183*, K178L+N194Y+R180*+S181*, K178L+N194Y+R180*+T182*, K178L+N194Y+R180*+G183*, K178L+N194Y+S181*+T182*, K178L+N194Y+T182*+G183* and K178L+G475K+S243Q+R180*+S181*.

In one embodiment, the variant comprises multiple alterations of the mature polypeptide of SEQ ID NO: 1 or 2 selected from the list consisting of A185F+R180*+S181*, A185F+R180*+T182*, A185F+R180*+G183*, A185F+S181*+T182*, A185F+T182*+G183*, A185F+N194F+R180*+S181*, A185F+N194F+R180*+T182*, A185F+N194F+R180*+G183*, A185F+N194F+S181*+T182*, A185F+N194F+T182*+G183*, A185F+N194Y+R180*+S181*, A185F+N194Y+R180*+T182*, A185F+N194Y+R180*+G183*, A185F+N194Y+S181*+T182*, A185F+N194Y+T182*+G183* and A185F+G475K+S243Q+R180*+S181*.

In one embodiment, the variant comprises multiple alterations of the mature polypeptide of SEQ ID NO: 1 or 2 selected from the list consisting of A185H+R180*+S181*, A185H+R180*+T182*, A185H+R180*+G183*, A185H+S181*+T182*, A185H+T182*+G183*, A185H+N194F+R180*+S181*, A185H+N194F+R180*+T182*, A185H+N194F+R180*+G183*, A185H+N194F+S181*+T182*, A185H+N194F+T182*+G183*, A185H+N194Y+R180*+S181*, A185H+N194Y+R180*+T182*, A185H+N194Y+R180*+G183*, A185H+N194Y+S181*+T182*, A185H+N194Y+T182*+G183* and A185H+G475K+S243Q+R180*+S181*.

In one embodiment, the variant comprises multiple alterations of the mature polypeptide of SEQ ID NO: 1 or 2 selected from the list consisting of A185L+R180*+S181*, A185L+R180*+T182*, A185L+R180*+G183*, A185L+S181*+T182*, A185L+T182*+G183*, A185L+N194F+R180*+S181*, A185L+N194F+R180*+T182*, A185L+N194F+R180*+G183*, A185L+N194F+S181*+T182*, A185L+N194F+T182*+G183*, A185L+N194Y+R180*+S181*, A185L+N194Y+R180*+T182*, A185L+N194Y+R180*+G183*, A185L+N194Y+S181*+T182*, A185L+N194Y+T182*+G183* and A185L+G475K+S243Q+R180*+S181*.

In one embodiment, the variant comprises multiple alterations of the mature polypeptide of SEQ ID NO: 1 or 2 selected from the list consisting of A185I+R180*+S181*, A185I+R180*+T182*, A185I+R180*+G183*, A185I+S181*+T182*, A185I+T182*+G183*, A185I+N194F+R180*+S181*, A185I+N194F+R180*+T182*, A185I+N194F+R180*+G183*, A185I+N194F+S181*+T182*, A185I+N194F+T182*+G183*, A185I+N194Y+R180*+S181*, A185I+N194Y+R180*+T182*, A185I+N194Y+R180*+G183*, A185I+N194Y+S181*+T182*, A185I+N194Y+T182*+G183* and A185I+G475K+S243Q+R180*+S181*.

In one embodiment, the variant comprises multiple alterations of the mature polypeptide of SEQ ID NO: 1 or 2 selected from the list consisting of A185P+R180*+S181*, A185P+R180*+T182*, A185P+R180*+G183*, A185P+S181*+T182*, A185P+T182*+G183*, A185P+N194F+R180*+S181*, A185P+N194F+R180*+T182*, A185P+N194F+R180*+G183*, A185P+N194F+S181*+T182*, A185P+N194F+T182*+G183*, A185P+N194Y+R180*+S181*, A185P+N194Y+R180*+T182*, A185P+N194Y+R180*+G183*, A185P+N194Y+S181*+T182*, A185P+N194Y+T182*+G183* and A185P+G475K+S243Q+R180*+S181*.

In one embodiment, the variant comprises multiple alterations of the mature polypeptide of SEQ ID NO: 1 or 2 selected from the list consisting of E189P+R180*+S181*, E189P+R180*+T182*, E189P+R180*+G183*, E189P+S181*+T182*, E189P+T182*+G183*, E189P+N194F+R180*+S181*, E189P+N194F+R180*+T182*, E189P+N194F+R180*+G183*, E189P+N194F+S181*+T182*, E189P+N194F+T182*+G183*, E189P+N194Y+R180*+S181*, E189P+N194Y+R180*+T182*, E189P+N194Y+R180*+G183*, E189P+N194Y+S181*+T182*, E189P+N194Y+T182*+G183* and E189P+G475K+S243Q+R180*+S181*.

In one embodiment, the variant comprises multiple alterations of the mature polypeptide of SEQ ID NO: 1 or 2 selected from the list consisting of N194F+R180*+S181*, N194F+R180*+T182*, N194F+R180*+G183*, N194F+S181*+T182*, N194F+T182*+G183* and N194F+G475K+S243Q+R180*+S181*.

In one embodiment, the variant comprises multiple alterations of the mature polypeptide of SEQ ID NO: 1 or 2 selected from the list consisting of N194Y+R180*+S181*, N194Y+R180*+T182*, N194Y+R180*+G183*, N194Y+S181*+T182*, N194Y+T182*+G183* and N194Y+G475K+S243Q+R180*+S181*.

In one embodiment, the variant comprises multiple alterations of the mature polypeptide of SEQ ID NO: 1 or 2 selected from the list consisting of N194H+R180*+S181*, N194H+R180*+T182*, N194H+R180*+G183*, N194H+S181*+T182*, N194H+T182*+G183* and N194H+G475K+S243Q+R180*+S181*.

In one embodiment, the variant comprises multiple alterations of the mature polypeptide of SEQ ID NO: 1 or 2 selected from the list consisting of N194L+R180*+S181*, N194L+R180*+T182*, N194L+R180*+G183*, N194L+S181*+T182*, N194L+T182*+G183* and N194L+G475K+S243Q+R180*+S181*.

In one embodiment, the variant comprises multiple alterations of the mature polypeptide of SEQ ID NO: 1 or 2 selected from the list consisting of N194I+R180*+S181*, N194I+R180*+T182*, N194I+R180*+G183*, N194I+S181*+T182*, N194I+T182*+G183* and N194I+G475K+S243Q+R180*+S181*.

In one embodiment, the variant comprises multiple alterations of the mature polypeptide of SEQ ID NO: 1 or 2 selected from the list consisting of A203S+R180*+S181*, A203S+R180*+T182*, A203S+R180*+G183*, A203S+S181*+T182*, A203S+T182*+G183*, A203S+N194F+R180*+S181*, A203S+N194F+R180*+T182*, A203S+N194F+R180*+G183*, A203S+N194F+S181*+T182*, A203S+N194F+T182*+G183*, A203S+N194Y+R180*+S181*, A203S+N194Y+R180*+T182*, A203S+N194Y+R180*+G183*, A203S+N194Y+S181*+T182*, A203S+N194Y+T182*+G183* and A203S+G475K+S243Q+R180*+S181*.

In one embodiment, the variant comprises multiple alterations of the mature polypeptide of SEQ ID NO: 1 or 2 selected from the list consisting of A203T+R180*+S181*, A203T+R180*+T182*, A203T+R180*+G183*, A203T+S181*+T182*, A203T+T182*+G183*, A203T+N194F+R180*+S181*, A203T+N194F+R180*+T182*, A203T+N194F+R180*+G183*, A203T+N194F+S181*+T182*, A203T+N194F+T182*+G183*, A203T+N194Y+R180*+

S181*, A203T+N194Y+R180*+T182*, A203T+N194Y+ R180*+G183*, A203T+N194Y+S181*+T182*, A203T+ N194Y+T182*+G183* and A203T+G475K+S243Q+ R180*+S181*.

In one embodiment, the variant comprises multiple alterations of the mature polypeptide of SEQ ID NO: 1 or 2 selected from the list consisting of L205F+R180*+S181*, L205F+R180*+T182*, L205F+R180*+G183*, L205F+ S181*+T182*, L205F+T182*+G183*, L205F+N194F+ R180*+S181*, L205F+N194F+R180*+T182*, L205F+ N194F+R180*+G183*, L205F+N194F+S181*+T182*, L205F+N194F+T182*+G183*, L205F+N194Y+R180*+ S181*, L205F+N194Y+R180*+T182*, L205F+N194Y+ R180*+G183*, L205F+N194Y+S181*+T182*, L205F+ N194Y+T182*+G183* and L205F+G475K+S243Q+ R180*+S181*.

In one embodiment, the variant comprises multiple alterations of the mature polypeptide of SEQ ID NO: 1 or 2 selected from the list consisting of L205Y+R180*+S181*, L205Y+R180*+T182*, L205Y+R180*+G183*, L205Y+ S181*+T182*, L205Y+T182*+G183*, L205Y+N194F+ R180*+S181*, L205Y+N194F+R180*+T182*, L205Y+ N194F+R180*+G183*, L205Y+N194F+S181*+T182*, L205Y+N194F+T182*+G183*, L205Y+N194Y+R180*+ S181*, L205Y+N194Y+R180*+T182*, L205Y+N194Y+ R180*+G183*, L205Y+N194Y+S181*+T182*, L205Y+ N194Y+T182*+G183* and L205Y+G475K+S243Q+ R180*+S181*.

In one embodiment, the variant comprises multiple alterations of the mature polypeptide of SEQ ID NO: 1 or 2 selected from the list consisting of L205I+R180*+S181*, L205I+R180*+T182*, L205I+R180*+G183*, L205I+ S181*+T182*, L205I+T182*+G183*, L205I+N194F+ R180*+S181*, L205I+N194F+R180*+T182*, L205I+ N194F+R180*+G183*, L205I+N194F+S181*+T182*, L205I+N194F+T182*+G183*, L205I+N194Y+R180*+ S181*, L205I+N194Y+R180*+T182*, L205I+N194Y+ R180*+G183*, L205I+N194Y+S181*+T182*, L205I+ N194Y+T182*+G183* and L205I+G475K+S243Q+ R180*+S181*.

In one embodiment, the variant comprises multiple alterations of the mature polypeptide of SEQ ID NO: 1 or 2 selected from the list consisting of M208F+R180*+S181*, M208F+R180*+T182*, M208F+R180*+G183*, M208F+ S181*+T182*, M208F+T182*+G183*, M208F+N194F+ R180*+S181*, M208F+N194F+R180*+T182*, M208F+ N194F+R180*+G183*, M208F+N194F+S181*+T182*, M208F+N194F+T182*+G183*, M208F+N194Y+R180*+ S181*, M208F+N194Y+R180*+T182*, M208F+N194Y+ R180*+G183*, M208F+N194Y+S181*+T182*, M208F+ N194Y+T182*+G183* and M208F+G475K+S243Q+ R180*+S181*.

In one embodiment, the variant comprises multiple alterations of the mature polypeptide of SEQ ID NO: 1 or 2 selected from the list consisting of M208I+R180*+S181*, M208I+R180*+T182*, M208I+R180*+G183*, M208I+ S181*+T182*, M208I+T182*+G183*, M208I+N194F+ R180*+S181*, M208I+N194F+R180*+T182*, M208I+ N194F+R180*+G183*, M208I+N194F+S181*+T182*, M208I+N194F+T182*+G183*, M208I+N194Y+R180*+ S181*, M208I+N194Y+R180*+T182*, M208I+N194Y+ R180*+G183*, M208I+N194Y+S181*+T182*, M208I+ N194Y+T182*+G183* and M208I+G475K+S243Q+ R180*+S181*.

In one embodiment, the variant comprises multiple alterations of the mature polypeptide of SEQ ID NO: 1 or 2 selected from the list consisting of M208L+R180*+S181*, M208L+R180*+T182*, M208L+R180*+G183*, M208L+ S181*+T182*, M208L+T182*+G183*, M208L+N194F+ R180*+S181*, M208L+N194F+R180*+T182*, M208L+ N194F+R180*+G183*, M208L+N194F+S181*+T182*, M208L+N194F+T182*+G183*, M208L+N194Y+R180*+ S181*, M208L+N194Y+R180*+T182*, M208L+N194Y+ R180*+G183*, M208L+N194Y+S181*+T182*, M208L+ N194Y+T182*+G183* and M208L+G475K+S243Q+ R180*+S181*.

In one embodiment, the variant comprises multiple alterations of the mature polypeptide of SEQ ID NO: 1 or 2 selected from the list consisting of M208Y+R180*+S181*, M208Y+R180*+T182*, M208Y+R180*+G183*, M208Y+ S181*+T182*, M208Y+T182*+G183*, M208Y+N194F+ R180*+S181*, M208Y+N194F+R180*+T182*, M208Y+ N194F+R180*+G183*, M208Y+N194F+S181*+T182*, M208Y+N194F+T182*+G183*, M208Y+N194Y+R180*+ S181*, M208Y+N194Y+R180*+T182*, M208Y+N194Y+ R180*+G183*, M208Y+N194Y+S181*+T182*, M208Y+ N194Y+T182*+G183* and M208Y+G475K+S243Q+ R180*+S181*.

In one embodiment, the variant comprises multiple alterations of the mature polypeptide of SEQ ID NO: 1 or 2 selected from the list consisting of H209D+R180*+S181*, H209D+R180*+T182*, H209D+R180*+G183*, H209D+ S181*+T182*, H209D+T182*+G183*, H209D+N194F+ R180*+S181*, H209D+N194F+R180*+T182*, H209D+ N194F+R180*+G183*, H209D+N194F+S181*+T182*, H209D+N194F+T182*+G183*, H209D+N194Y+R180*+ S181*, H209D+N194Y+R180*+T182*, H209D+N194Y+ R180*+G183*, H209D+N194Y+S181*+T182*, H209D+ N194Y+T182*+G183* and H209D+G475K+S243Q+ R180*+S181*.

In one embodiment, the variant comprises multiple alterations of the mature polypeptide of SEQ ID NO: 1 or 2 selected from the list consisting of H209M+R180*+S181*, H209M+R180*+T182*, H209M+R180*+G183*, H209M+ S181*+T182*, H209M+T182*+G183*, H209M+N194F+ R180*+S181*, H209M+N194F+R180*+T182*, H209M+ N194F+R180*+G183*, H209M+N194F+S181*+T182*, H209M+N194F+T182*+G183*, H209M+N194Y+R180*+ S181*, H209M+N194Y+R180*+T182*, H209M+N194Y+ R180*+G183*, H209M+N194Y+S181*+T182*, H209M+ N194Y+T182*+G183* and H209M+G475K+S243Q+ R180*+S181*.

In one embodiment, the variant comprises multiple alterations of the mature polypeptide of SEQ ID NO: 1 or 2 selected from the list consisting of H209T+R180*+S181*, H209T+R180*+T182*, H209T+R180*+G183*, H209T+ S181*+T182*, H209T+T182*+G183*, H209T+N194F+ R180*+S181*, H209T+N194F+R180*+T182*, H209T+ N194F+R180*+G183*, H209T+N194F+S181*+T182*, H209T+N194F+T182*+G183*, H209T+N194Y+R180*+ S181*, H209T+N194Y+R180*+T182*, H209T+N194Y+ R180*+G183*, H209T+N194Y+S181*+T182*, H209T+ N194Y+T182*+G183* and H209T+G475K+S243Q+ R180*+S181*.

In one embodiment, the variant comprises multiple alterations of the mature polypeptide of SEQ ID NO: 1 or 2 selected from the list consisting of E211D+R180*+S181*, E211D+R180*+T182*, E211D+R180*+G183*, E211D+ S181*+T182*, E211D+T182*+G183*, E211D+N194F+ R180*+S181*, E211D+N194F+R180*+T182*, E211D+ N194F+R180*+G183*, E211D+N194F+S181*+T182*, E211D+N194F+T182*+G183*, E211D+N194Y+R180*+ S181*, E211D+N194Y+R180*+T182*, E211D+N194Y+

R180*+G183*, E211D+N194Y+S181*+T182*, E211D+N194Y+T182*+G183* and E211D+G475K+S243Q+R180*+S181*.

In one embodiment, the variant comprises multiple alterations of the mature polypeptide of SEQ ID NO: 1 or 2 selected from the list consisting of E211L+R180*+S181*, E211L+R180*+T182*, E211L+R180*+G183*, E211L+S181*+T182*, E211L+T182*+G183*, E211L+N194F+R180*+S181*, E211L+N194F+R180*+T182*, E211L+N194F+R180*+G183*, E211L+N194F+S181*+T182*, E211L+N194F+T182*+G183*, E211L+N194Y+R180*+S181*, E211L+N194Y+R180*+T182*, E211L+N194Y+R180*+G183*, E211L+N194Y+S181*+T182*, E211L+N194Y+T182*+G183* and E211L+G475K+S243Q+R180*+S181*.

In one embodiment, the variant comprises multiple alterations of the mature polypeptide of SEQ ID NO: 1 or 2 selected from the list consisting of Y48W+R180*+S181*, Y48W+R180*+T182*, Y48W+R180*+G183*, Y48W+S181*+T182*, Y48W+T182*+G183*, Y48W+N194F+R180*+S181*, Y48W+N194F+R180*+T182*, Y48W+N194F+R180*+G183*, Y48W+N194F+S181*+T182*, Y48W+N194F+T182*+G183*, Y48W+N194Y+R180*+S181*, Y48W+N194Y+R180*+T182*, Y48W+N194Y+R180*+G183*, Y48W+N194Y+S181*+T182*, Y48W+N194Y+T182*+G183* and Y48W+G475K+S243Q+R180*+S181*.

In one embodiment, the variant comprises multiple alterations of the mature polypeptide of SEQ ID NO: 1 or 2 selected from the list consisting of V212A+R180*+S181*, V212A+R180*+T182*, V212A+R180*+G183*, V212A+S181*+T182*, V212A+T182*+G183*, V212A+N194F+R180*+S181*, V212A+N194F+R180*+T182*, V212A+N194F+R180*+G183*, V212A+N194F+S181*+T182*, V212A+N194F+T182*+G183*, V212A+N194Y+R180*+S181*, V212A+N194Y+R180*+T182*, V212A+N194Y+R180*+G183*, V212A+N194Y+S181*+T182*, V212A+N194Y+T182*+G183* and V212A+G475K+S243Q+R180*+S181*.

In one embodiment, the variant comprises multiple alterations of the mature polypeptide of SEQ ID NO: 1 or 2 selected from the list consisting of R309Q+R180*+S181*, R309Q+R180*+T182*, R309Q+R180*+G183*, R309Q+S181*+T182*, R309Q+T182*+G183*, R309Q+N194F+R180*+S181*, R309Q+N194F+R180*+T182*, R309Q+N194F+R180*+G183*, R309Q+N194F+S181*+T182*, R309Q+N194F+T182*+G183*, R309Q+N194Y+R180*+S181*, R309Q+N194Y+R180*+T182*, R309Q+N194Y+R180*+G183*, R309Q+N194Y+S181*+T182*, R309Q+N194Y+T182*+G183* and R309Q+G475K+S243Q+R180*+S181*.

In one embodiment, the variant comprises multiple alterations of the mature polypeptide of SEQ ID NO: 1 or 2 selected from the list consisting of I390E+R180*+S181*, I390E+R180*+T182*, I390E+R180*+G183*, I390E+S181*+T182*, I390E+T182*+G183*, I390E+N194F+R180*+S181*, I390E+N194F+R180*+T182*, I390E+N194F+R180*+G183*, I390E+N194F+S181*+T182*, I390E+N194F+T182*+G183*, I390E+N194Y+R180*+S181*, I390E+N194Y+R180*+T182*, I390E+N194Y+R180*+G183*, I390E+N194Y+S181*+T182*, I390E+N194Y+T182*+G183* and I390E+G475K+S243Q+R180*+S181*.

In one embodiment, the variant comprises multiple alterations of the mature polypeptide of SEQ ID NO: 1 or 2 selected from the list consisting of M317L+R180*+S181*, M317L+R180*+T182*, M317L+R180*+G183*, M317L+S181*+T182*, M317L+T182*+G183*, M317L+N194F+R180*+S181*, M317L+N194F+R180*+T182*, M317L+N194F+R180*+G183*, M317L+N194F+S181*+T182*, M317L+N194F+T182*+G183*, M317L+N194Y+R180*+S181*, M317L+N194Y+R180*+T182*, M317L+N194Y+R180*+G183*, M317L+N194Y+S181*+T182*, M317L+N194Y+T182*+G183* and M317L+G475K+S243Q+R180*+S181*.

In one embodiment, the variant comprises multiple alterations of the mature polypeptide of SEQ ID NO: 1 or 2 selected from the list consisting of V212N+R180*+S181*, V212N+R180*+T182*, V212N+R180*+G183*, V212N+S181*+T182*, V212N+T182*+G183*, V212N+N194F+R180*+S181*, V212N+N194F+R180*+T182*, V212N+N194F+R180*+G183*, V212N+N194F+S181*+T182*, V212N+N194F+T182*+G183*, V212N+N194Y+R180*+S181*, V212N+N194Y+R180*+T182*, V212N+N194Y+R180*+G183*, V212N+N194Y+S181*+T182*, V212N+N194Y+T182*+G183* and V212N+G475K+S243Q+R180*+S181*.

In one embodiment, the variant comprises multiple alterations of the mature polypeptide of SEQ ID NO: 1 or 2 selected from the list consisting of V212I+R180*+S181*, V212I+R180*+T182*, V212I+R180*+G183*, V212I+S181*+T182*, V212I+T182*+G183*, V212I+N194F+R180*+S181*, V212I+N194F+R180*+T182*, V212I+N194F+R180*+G183*, V212I+N194F+S181*+T182*, V212I+N194F+T182*+G183*, V212I+N194Y+R180*+S181*, V212I+N194Y+R180*+T182*, V212I+N194Y+R180*+G183*, V212I+N194Y+S181*+T182*, V212I+N194Y+T182*+G183* and V212I+G475K+S243Q+R180*+S181*.

In one embodiment, the variant comprises multiple alterations of the mature polypeptide of SEQ ID NO: 1 or 2 selected from the list consisting of N174NN+R180*+S181*, N174NN+R180*+T182*, N174NN+R180*+G183*, N174NN+S181*+T182*, N174NN+T182*+G183*, N174NN+N194F+R180*+S181*, N174NN+N194F+R180*+T182*, N174NN+N194F+R180*+G183*, N174NN+N194F+S181*+T182*, N174NN+N194F+T182*+G183*, N174NN+N194Y+R180*+S181*, N174NN+N194Y+R180*+T182*, N174NN+N194Y+R180*+G183*, N174NN+N194Y+S181*+T182*, N174NN+N194Y+T182*+G183* and N174NN+G475K+S243Q+R180*+S181*.

In one embodiment, the variant comprises multiple alterations of the mature polypeptide of SEQ ID NO: 1 or 2 selected from the list consisting of V213S+R180*+S181*, V213S+R180*+T182*, V213S+R180*+G183*, V213S+S181*+T182*, V213S+T182*+G183*, V213S+N194F+R180*+S181*, V213S+N194F+R180*+T182*, V213S+N194F+R180*+G183*, V213S+N194F+S181*+T182*, V213S+N194F+T182*+G183*, V213S+N194Y+R180*+S181*, V213S+N194Y+R180*+T182*, V213S+N194Y+R180*+G183*, V213S+N194Y+S181*+T182*, V213S+N194Y+T182*+G183* and V213S+G475K+S243Q+R180*+S181*.

In one embodiment, the variant comprises multiple alterations of the mature polypeptide of SEQ ID NO: 1 or 2 selected from the list consisting of N174NQ+R180*+S181*, N174NQ+R180*+T182*, N174NQ+R180*+G183*, N174NQ+S181*+T182*, N174NQ+T182*+G183*, N174NQ+N194F+R180*+S181*, N174NQ+N194F+R180*+T182*, N174NQ+N194F+R180*+G183*, N174NQ+N194F+S181*+T182*, N174NQ+N194F+T182*+G183*, N174NQ+N194Y+R180*+S181*, N174NQ+N194Y+R180*+T182*, N174NQ+N194Y+

R180*+G183*, N174NQ+N194Y+S181*+T182*, N174NQ+N194Y+T182*+G183* and N174NQ+G475K+S243Q+R180*+S181*.

In one embodiment, the variant comprises multiple alterations of the mature polypeptide of SEQ ID NO: 1 or 2 selected from the list consisting of V213Q+R180*+S181*, V213Q+R180*+T182*, V213Q+R180*+G183*, V213Q+S181*+T182*, V213Q+T182*+G183*, V213Q+N194F+R180*+S181*, V213Q+N194F+R180*+T182*, V213Q+N194F+R180*+G183*, V213Q+N194F+S181*+T182*, V213Q+N194F+T182*+G183*, V213Q+N194Y+R180*+S181*, V213Q+N194Y+R180*+T182*, V213Q+N194Y+R180*+G183*, V213Q+N194Y+S181*+T182*, V213Q+N194Y+T182*+G183* and V213Q+G475K+S243Q+R180*+S181*.

In one embodiment, the variant comprises multiple alterations of the mature polypeptide of SEQ ID NO: 1 or 2 selected from the list consisting of K241R+R180*+S181*, K241R+R180*+T182*, K241R+R180*+G183*, K241R+S181*+T182*, K241R+T182*+G183*, K241R+N194F+R180*+S181*, K241R+N194F+R180*+T182*, K241R+N194F+R180*+G183*, K241R+N194F+S181*+T182*, K241R+N194F+T182*+G183*, K241R+N194Y+R180*+S181*, K241R+N194Y+R180*+T182*, K241R+N194Y+R180*+G183*, K241R+N194Y+S181*+T182*, K241R+N194Y+T182*+G183* and K241R+G475K+S243Q+R180*+S181*.

In one embodiment, the variant comprises multiple alterations of the mature polypeptide of SEQ ID NO: 1 or 2 selected from the list consisting of Y242F+R180*+S181*, Y242F+R180*+T182*, Y242F+R180*+G183*, Y242F+S181*+T182*, Y242F+T182*+G183*, Y242F+N194F+R180*+S181*, Y242F+N194F+R180*+T182*, Y242F+N194F+R180*+G183*, Y242F+N194F+S181*+T182*, Y242F+N194F+T182*+G183*, Y242F+N194Y+R180*+S181*, Y242F+N194Y+R180*+T182*, Y242F+N194Y+R180*+G183*, Y242F+N194Y+S181*+T182*, Y242F+N194Y+T182*+G183* and Y242F+G475K+S243Q+R180*+S181*.

In one embodiment, the variant comprises multiple alterations of the mature polypeptide of SEQ ID NO: 1 or 2 selected from the list consisting of F245I+R180*+S181*, F245I+R180*+T182*, F245I+R180*+G183*, F245I+S181*+T182*, F245I+T182*+G183*, F245I+N194F+R180*+S181*, F245I+N194F+R180*+T182*, F245I+N194F+R180*+G183*, F245I+N194F+S181*+T182*, F245I+N194F+T182*+G183*, F245I+N194Y+R180*+S181*, F245I+N194Y+R180*+T182*, F245I+N194Y+R180*+G183*, F245I+N194Y+S181*+T182*, F245I+N194Y+T182*+G183* and F245I+G475K+S243Q+R180*+S181*.

In one embodiment, the variant comprises multiple alterations of the mature polypeptide of SEQ ID NO: 1 or 2 selected from the list consisting of F245L+R180*+S181*, F245L+R180*+T182*, F245L+R180*+G183*, F245L+S181*+T182*, F245L+T182*+G183*, F245L+N194F+R180*+S181*, F245L+N194F+R180*+T182*, F245L+N194F+R180*+G183*, F245L+N194F+S181*+T182*, F245L+N194F+T182*+G183*, F245L+N194Y+R180*+S181*, F245L+N194Y+R180*+T182*, F245L+N194Y+R180*+G183*, F245L+N194Y+S181*+T182*, F245L+N194Y+T182*+G183* and F245L+G475K+S243Q+R180*+S181*.

In one embodiment, the variant comprises multiple alterations of the mature polypeptide of SEQ ID NO: 1 or 2 selected from the list consisting of F245M+R180*+S181*, F245M+R180*+T182*, F245M+R180*+G183*, F245M+S181*+T182*, F245M+T182*+G183*, F245M+N194F+R180*+S181*, F245M+N194F+R180*+T182*, F245M+N194F+R180*+G183*, F245M+N194F+S181*+T182*, F245M+N194F+T182*+G183*, F245M+N194Y+R180*+S181*, F245M+N194Y+R180*+T182*, F245M+N194Y+R180*+G183*, F245M+N194Y+S181*+T182*, F245M+N194Y+T182*+G183* and F245M+G475K+S243Q+R180*+S181*.

In one embodiment, the variant comprises multiple alterations of the mature polypeptide of SEQ ID NO: 1 or 2 selected from the list consisting of F245S+R180*+S181*, F245S+R180*+T182*, F245S+R180*+G183*, F245S+S181*+T182*, F245S+T182*+G183*, F245S+N194F+R180*+S181*, F245S+N194F+R180*+T182*, F245S+N194F+R180*+G183*, F245S+N194F+S181*+T182*, F245S+N194F+T182*+G183*, F245S+N194Y+R180*+S181*, F245S+N194Y+R180*+T182*, F245S+N194Y+R180*+G183*, F245S+N194Y+S181*+T182*, F245S+N194Y+T182*+G183* and F245S+G475K+S243Q+R180*+S181*.

In one embodiment, the variant comprises multiple alterations of the mature polypeptide of SEQ ID NO: 1 or 2 selected from the list consisting of F245T+R180*+S181*, F245T+R180*+T182*, F245T+R180*+G183*, F245T+S181*+T182*, F245T+T182*+G183*, F245T+N194F+R180*+S181*, F245T+N194F+R180*+T182*, F245T+N194F+R180*+G183*, F245T+N194F+S181*+T182*, F245T+N194F+T182*+G183*, F245T+N194Y+R180*+S181*, F245T+N194Y+R180*+T182*, F245T+N194Y+R180*+G183*, F245T+N194Y+S181*+T182*, F245T+N194Y+T182*+G183* and F245T+G475K+S243Q+R180*+S181*.

In one embodiment, the variant comprises multiple alterations of the mature polypeptide of SEQ ID NO: 1 or 2 selected from the list consisting of F245V+R180*+S181*, F245V+R180*+T182*, F245V+R180*+G183*, F245V+S181*+T182*, F245V+T182*+G183*, F245V+N194F+R180*+S181*, F245V+N194F+R180*+T182*, F245V+N194F+R180*+G183*, F245V+N194F+S181*+T182*, F245V+N194F+T182*+G183*, F245V+N194Y+R180*+S181*, F245V+N194Y+R180*+T182*, F245V+N194Y+R180*+G183*, F245V+N194Y+S181*+T182*, F245V+N194Y+T182*+G183* and F245V+G475K+S243Q+R180*+S181*.

In one embodiment, the variant comprises multiple alterations of the mature polypeptide of SEQ ID NO: 1 or 2 selected from the list consisting of F245Y+R180*+S181*, F245Y+R180*+T182*, F245Y+R180*+G183*, F245Y+S181*+T182*, F245Y+T182*+G183*, F245Y+N194F+R180*+S181*, F245Y+N194F+R180*+T182*, F245Y+N194F+R180*+G183*, F245Y+N194F+S181*+T182*, F245Y+N194F+T182*+G183*, F245Y+N194Y+R180*+S181*, F245Y+N194Y+R180*+T182*, F245Y+N194Y+R180*+G183*, F245Y+N194Y+S181*+T182*, F245Y+N194Y+T182*+G183* and F245Y+G475K+S243Q+R180*+S181*.

In one embodiment, the variant comprises multiple alterations of the mature polypeptide of SEQ ID NO: 1 or 2 selected from the list consisting of F266Y+R180*+S181*, F266Y+R180*+T182*, F266Y+R180*+G183*, F266Y+S181*+T182*, F266Y+T182*+G183*, F266Y+N194F+R180*+S181*, F266Y+N194F+R180*+T182*, F266Y+N194F+R180*+G183*, F266Y+N194F+S181*+T182*, F266Y+N194F+T182*+G183*, F266Y+N194Y+R180*+S181*, F266Y+N194Y+R180*+T182*, F266Y+N194Y+

R180*+G183*, F266Y+N194Y+S181*+T182*, F266Y+N194Y+T182*+G183* and F266Y+G475K+S243Q+R180*+S181*.

In one embodiment, the variant comprises multiple alterations of the mature polypeptide of SEQ ID NO: 1 or 2 selected from the list consisting of Y269N+R180*+S181*, Y269N+R180*+T182*, Y269N+R180*+G183*, Y269N+S181*+T182*, Y269N+T182*+G183*, Y269N+N194F+R180*+S181*, Y269N+N194F+R180*+T182*, Y269N+N194F+R180*+G183*, Y269N+N194F+S181*+T182*, Y269N+N194F+T182*+G183*, Y269N+N194Y+R180*+S181*, Y269N+N194Y+R180*+T182*, Y269N+N194Y+R180*+G183*, Y269N+N194Y+S181*+T182*, Y269N+N194Y+T182*+G183* and Y269N+G475K+S243Q+R180*+S181*.

In one embodiment, the variant comprises multiple alterations of the mature polypeptide of SEQ ID NO: 1 or 2 selected from the list consisting of K280R+R180*+S181*, K280R+R180*+T182*, K280R+R180*+G183*, K280R+S181*+T182*, K280R+T182*+G183*, K280R+N194F+R180*+S181*, K280R+N194F+R180*+T182*, K280R+N194F+R180*+G183*, K280R+N194F+S181*+T182*, K280R+N194F+T182*+G183*, K280R+N194Y+R180*+S181*, K280R+N194Y+R180*+T182*, K280R+N194Y+R180*+G183*, K280R+N194Y+S181*+T182*, K280R+N194Y+T182*+G183* and K280R+G475K+S243Q+R180*+S181*.

In one embodiment, the variant comprises multiple alterations of the mature polypeptide of SEQ ID NO: 1 or 2 selected from the list consisting of G283S+R180*+S181*, G283S+R180*+T182*, G283S+R180*+G183*, G283S+S181*+T182*, G283S+T182*+G183*, G283S+N194F+R180*+S181*, G283S+N194F+R180*+T182*, G283S+N194F+R180*+G183*, G283S+N194F+S181*+T182*, G283S+N194F+T182*+G183*, G283S+N194Y+R180*+S181*, G283S+N194Y+R180*+T182*, G283S+N194Y+R180*+G183*, G283S+N194Y+S181*+T182*, G283S+N194Y+T182*+G183* and G283S+G475K+S243Q+R180*+S181*.

In one embodiment, the variant comprises multiple alterations of the mature polypeptide of SEQ ID NO: 1 or 2 selected from the list consisting of M285F+R180*+S181*, M285F+R180*+T182*, M285F+R180*+G183*, M285F+S181*+T182*, M285F+T182*+G183*, M285F+N194F+R180*+S181*, M285F+N194F+R180*+T182*, M285F+N194F+R180*+G183*, M285F+N194F+S181*+T182*, M285F+N194F+T182*+G183*, M285F+N194Y+R180*+S181*, M285F+N194Y+R180*+T182*, M285F+N194Y+R180*+G183*, M285F+N194Y+S181*+T182*, M285F+N194Y+T182*+G183* and M285F+G475K+S243Q+R180*+S181*.

In one embodiment, the variant comprises multiple alterations of the mature polypeptide of SEQ ID NO: 1 or 2 selected from the list consisting of M285H+R180*+S181*, M285H+R180*+T182*, M285H+R180*+G183*, M285H+S181*+T182*, M285H+T182*+G183*, M285H+N194F+R180*+S181*, M285H+N194F+R180*+T182*, M285H+N194F+R180*+G183*, M285H+N194F+S181*+T182*, M285H+N194F+T182*+G183*, M285H+N194Y+R180*+S181*, M285H+N194Y+R180*+T182*, M285H+N194Y+R180*+G183*, M285H+N194Y+S181*+T182*, M285H+N194Y+T182*+G183* and M285H+G475K+S243Q+R180*+S181*.

In one embodiment, the variant comprises multiple alterations of the mature polypeptide of SEQ ID NO: 1 or 2 selected from the list consisting of N294Y+R180*+S181*, N294Y+R180*+T182*, N294Y+R180*+G183*, N294Y+S181*+T182*, N294Y+T182*+G183*, N294Y+N194F+R180*+S181*, N294Y+N194F+R180*+T182*, N294Y+N194F+R180*+G183*, N294Y+N194F+S181*+T182*, N294Y+N194F+T182*+G183*, N294Y+N194Y+R180*+S181*, N294Y+N194Y+R180*+T182*, N294Y+N194Y+R180*+G183*, N294Y+N194Y+S181*+T182*, N294Y+N194Y+T182*+G183* and N294Y+G475K+S243Q+R180*+S181*.

In one embodiment, the variant comprises multiple alterations of the mature polypeptide of SEQ ID NO: 1 or 2 selected from the list consisting of M317F+R180*+S181*, M317F+R180*+T182*, M317F+R180*+G183*, M317F+S181*+T182*, M317F+T182*+G183*, M317F+N194F+R180*+S181*, M317F+N194F+R180*+T182*, M317F+N194F+R180*+G183*, M317F+N194F+S181*+T182*, M317F+N194F+T182*+G183*, M317F+N194Y+R180*+S181*, M317F+N194Y+R180*+T182*, M317F+N194Y+R180*+G183*, M317F+N194Y+S181*+T182*, M317F+N194Y+T182*+G183* and M317F+G475K+S243Q+R180*+S181*.

In one embodiment, the variant comprises multiple alterations of the mature polypeptide of SEQ ID NO: 1 or 2 selected from the list consisting of M317I+R180*+S181*, M317I+R180*+T182*, M317I+R180*+G183*, M317I+S181*+T182*, M317I+T182*+G183*, M317I+N194F+R180*+S181*, M317I+N194F+R180*+T182*, M317I+N194F+R180*+G183*, M317I+N194F+S181*+T182*, M317I+N194F+T182*+G183*, M317I+N194Y+R180*+S181*, M317I+N194Y+R180*+T182*, M317I+N194Y+R180*+G183*, M317I+N194Y+S181*+T182*, M317I+N194Y+T182*+G183* and M317I+G475K+S243Q+R180*+S181*.

In one embodiment, the variant comprises multiple alterations of the mature polypeptide of SEQ ID NO: 1 or 2 selected from the list consisting of M317L+R180*+S181*, M317L+R180*+T182*, M317L+R180*+G183*, M317L+S181*+T182*, M317L+T182*+G183*, M317L+N194F+R180*+S181*, M317L+N194F+R180*+T182*, M317L+N194F+R180*+G183*, M317L+N194F+S181*+T182*, M317L+N194F+T182*+G183*, M317L+N194Y+R180*+S181*, M317L+N194Y+R180*+T182*, M317L+N194Y+R180*+G183*, M317L+N194Y+S181*+T182*, M317L+N194Y+T182*+G183* and M317L+G475K+S243Q+R180*+S181*.

In one embodiment, the variant comprises multiple alterations of the mature polypeptide of SEQ ID NO: 1 or 2 selected from the list consisting of M317V+R180*+S181*, M317V+R180*+T182*, M317V+R180*+G183*, M317V+S181*+T182*, M317V+T182*+G183*, M317V+N194F+R180*+S181*, M317V+N194F+R180*+T182*, M317V+N194F+R180*+G183*, M317V+N194F+S181*+T182*, M317V+N194F+T182*+G183*, M317V+N194Y+R180*+S181*, M317V+N194Y+R180*+T182*, M317V+N194Y+R180*+G183*, M317V+N194Y+S181*+T182*, M317V+N194Y+T182*+G183* and M317V+G475K+S243Q+R180*+S181*.

In one embodiment, the variant comprises multiple alterations of the mature polypeptide of SEQ ID NO: 1 or 2 selected from the list consisting of M317Y+R180*+S181*, M317Y+R180*+T182*, M317Y+R180*+G183*, M317Y+S181*+T182*, M317Y+T182*+G183*, M317Y+N194F+R180*+T182*, M317Y+N194F+R180*+G183*, M317Y+N194F+S181*+T182*, M317Y+N194F+T182*+G183*, M317Y+N194Y+R180*+S181*, M317Y+N194Y+R180*+T182*, M317Y+N194Y+

R180*+G183*, M317Y+N194Y+S181*+T182*, M317Y+ N194Y+T182*+G183* and M317Y+G475K+S243Q+ R180*+S181*.

In one embodiment, the variant comprises multiple alterations of the mature polypeptide of SEQ ID NO: 1 or 2 selected from the list consisting of L323H+R180*+S181*, L323H+R180*+T182*, L323H+R180*+G183*, L323H+ S181*+T182*, L323H+T182*+G183*, L323H+N194F+ R180*+S181*, L323H+N194F+R180*+T182*, L323H+ N194F+R180*+G183*, L323H+N194F+S181*+T182*, L323H+N194F+T182*+G183*, L323H+N194Y+R180*+ S181*, L323H+N194Y+R180*+T182*, L323H+N194Y+ R180*+G183*, L323H+N194Y+S181*+T182*, L323H+ N194Y+T182*+G183* and L323H+G475K+S243Q+ R180*+S181*.

In one embodiment, the variant comprises multiple alterations of the mature polypeptide of SEQ ID NO: 1 or 2 selected from the list consisting of K375Q+R180*+S181*, K375Q+R180*+T182*, K375Q+R180*+G183*, K375Q+ S181*+T182*, K375Q+T182*+G183*, K375Q+N194F+ R180*+S181*, K375Q+N194F+R180*+T182*, K375Q+ N194F+R180*+G183*, K375Q+N194F+S181*+T182*, K375Q+N194F+T182*+G183*, K375Q+N194Y+R180*+ S181*, K375Q+N194Y+R180*+T182*, K375Q+N194Y+ R180*+G183*, K375Q+N194Y+S181*+T182*, K375Q+ N194Y+T182*+G183* and K375Q+G475K+S243Q+ R180*+S181*.

In one embodiment, the variant comprises multiple alterations of the mature polypeptide of SEQ ID NO: 1 or 2 selected from the list consisting of I390E+R180*+S181*, I390E+R180*+T182*, I390E+R180*+G183*, I390E+ S181*+T182*, I390E+T182*+G183*, I390E+N194F+ R180*+S181*, I390E+N194F+R180*+T182*, I390E+ N194F+R180*+G183*, I390E+N194F+S181*+T182*, I390E+N194F+T182*+G183*, I390E+N194Y+R180*+ S181*, I390E+N194Y+R180*+T182*, I390E+N194Y+ R180*+G183*, I390E+N194Y+S181*+T182*, I390E+ N194Y+T182*+G183* and I390E+G475K+S243Q+ R180*+S181*.

In one embodiment, the variant comprises multiple alterations of the mature polypeptide of SEQ ID NO: 1 or 2 selected from the list consisting of I390D+R180*+S181*, I390D+R180*+T182*, I390D+R180*+G183*, I390D+ S181*+T182*, I390D+T182*+G183*, I390D+N194F+ R180*+S181*, I390D+N194F+R180*+T182*, I390D+ N194F+R180*+G183*, I390D+N194F+S181*+T182*, I390D+N194F+T182*+G183*, I390D+N194Y+R180*+ S181*, I390D+N194Y+R180*+T182*, I390D+N194Y+ R180*+G183*, I390D+N194Y+S181*+T182*, I390D+ N194Y+T182*+G183* and I390D+G475K+S243Q+ R180*+S181*.

In one embodiment, the variant comprises multiple alterations of the mature polypeptide of SEQ ID NO: 1 or 2 selected from the list consisting of I390Q+R180*+S181*, I390Q+R180*+T182*, I390Q+R180*+G183*, I390Q+ S181*+T182*, I390Q+T182*+G183*, I390Q+N194F+ R180*+S181*, I390Q+N194F+R180*+T182*, I390Q+ N194F+R180*+G183*, I390Q+N194F+S181*+T182*, I390Q+N194F+T182*+G183*, I390Q+N194Y+R180*+ S181*, I390Q+N194Y+R180*+T182*, I390Q+N194Y+ R180*+G183*, I390Q+N194Y+S181*+T182*, I390Q+ N194Y+T182*+G183* and I390Q+G475K+S243Q+ R180*+S181*.

In one embodiment, the variant comprises multiple alterations of the mature polypeptide of SEQ ID NO: 1 or 2 selected from the list consisting of I390N+R180*+S181*, I390N+R180*+T182*, I390N+R180*+G183*, I390N+ S181*+T182*, I390N+T182*+G183*, I390N+N194F+ R180*+S181*, I390N+N194F+R180*+T182*, I390N+ N194F+R180*+G183*, I390N+N194F+S181*+T182*, I390N+N194F+T182*+G183*, I390N+N194Y+R180*+ S181*, I390N+N194Y+R180*+T182*, I390N+N194Y+ R180*+G183*, I390N+N194Y+S181*+T182*, I390N+ N194Y+T182*+G183* and I390N+G475K+S243Q+ R180*+S181*.

In one embodiment, the variant comprises multiple alterations of the mature polypeptide of SEQ ID NO: 1 or 2 selected from the list consisting of I404F+R180*+S181*, I404F+R180*+T182*, I404F+R180*+G183*, I404F+ S181*+T182*, I404F+T182*+G183*, I404F+N194F+ R180*+S181*, I404F+N194F+R180*+T182*, I404F+ N194F+R180*+G183*, I404F+N194F+S181*+T182*, I404F+N194F+T182*+G183*, I404F+N194Y+R180*+ S181*, I404F+N194Y+R180*+T182*, I404F+N194Y+ R180*+G183*, I404F+N194Y+S181*+T182*, I404F+ N194Y+T182*+G183* and I404F+G475K+S243Q+ R180*+S181*.

In one embodiment, the variant comprises multiple alterations of the mature polypeptide of SEQ ID NO: 1 or 2 selected from the list consisting of I404L+R180*+S181*, I404L+R180*+T182*, I404L+R180*+G183*, I404L+ S181*+T182*, I404L+T182*+G183*, I404L+N194F+ R180*+S181*, I404L+N194F+R180*+T182*, I404L+ N194F+R180*+G183*, I404L+N194F+S181*+T182*, I404L+N194F+T182*+G183*, I404L+N194Y+R180*+ S181*, I404L+N194Y+R180*+T182*, I404L+N194Y+ R180*+G183*, I404L+N194Y+S181*+T182*, I404L+ N194Y+T182*+G183* and I404L+G475K+S243Q+ R180*+S181*.

In one embodiment, the variant comprises multiple alterations of the mature polypeptide of SEQ ID NO: 1 or 2 selected from the list consisting of I404Y+R180*+S181*, I404Y+R180*+T182*, I404Y+R180*+G183*, I404Y+ S181*+T182*, I404Y+T182*+G183*, I404Y+N194F+ R180*+S181*, I404Y+N194F+R180*+T182*, I404Y+ N194F+R180*+G183*, I404Y+N194F+S181*+T182*, I404Y+N194F+T182*+G183*, I404Y+N194Y+R180*+ S181*, I404Y+N194Y+R180*+T182*, I404Y+N194Y+ R180*+G183*, I404Y+N194Y+S181*+T182*, I404Y+ N194Y+T182*+G183* and I404Y+G475K+S243Q+ R180*+S181*.

In one embodiment, the variant comprises multiple alterations of the mature polypeptide of SEQ ID NO: 1 or 2 selected from the list consisting of Q407H+R180*+S181*, Q407H+R180*+T182*, Q407H+R180*+G183*, Q407H+ S181*+T182*, Q407H+T182*+G183*, Q407H+N194F+ R180*+S181*, Q407H+N194F+R180*+T182*, Q407H+ N194F+R180*+G183*, Q407H+N194F+S181*+T182*, Q407H+N194F+T182*+G183*, Q407H+N194Y+R180*+ S181*, Q407H+N194Y+R180*+T182*, Q407H+N194Y+ R180*+G183*, Q407H+N194Y+S181*+T182*, Q407H+ N194Y+T182*+G183* and Q407H+G475K+S243Q+ R180*+S181*.

In one embodiment, the variant comprises multiple alterations of the mature polypeptide of SEQ ID NO: 1 or 2 selected from the list consisting of N194F+L205Y+R180*+ S181*, N194F+L205Y+R180*+T182*, N194F+L205Y+ R180*+G183*, N194F+L205Y+S181*+T182*, N194F+ L205Y+T182*+G183* and N194F+L205Y+G475K+ S243Q+R180*+S181*.

In one embodiment, the variant comprises multiple alterations of the mature polypeptide of SEQ ID NO: 1 or 2 selected from the list consisting of N194F+L205F+R180*+ S181*, N194F+L205F+R180*+T182*, N194F+L205F+

R180*+G183*, N194F+L205F+S181*+T182*, N194F+L205F+T182*+G183* and N194F+L205F+G475K+S243Q+R180*+S181*.

In one embodiment, the variant comprises multiple alterations of the mature polypeptide of SEQ ID NO: 1 or 2 selected from the list consisting of N194Y+L205Y+R180*+S181*, N194Y+L205Y+R180*+T182*, N194Y+L205Y+R180*+G183*, N194Y+L205Y+S181*+T182*, N194Y+L205Y+T182*+G183* and N194Y+L205Y+G475K+S243Q+R180*+S181*.

In one embodiment, the variant comprises multiple alterations of the mature polypeptide of SEQ ID NO: 1 or 2 selected from the list consisting of N194Y+L205F+R180*+S181*, N194Y+L205F+R180*+T182*, N194Y+L205F+R180*+G183*, N194Y+L205F+S181*+T182*, N194Y+L205F+T182*+G183* and N194Y+L205F+G475K+S243Q+R180*+S181*.

In one embodiment, the variant comprises multiple alterations of the mature polypeptide of SEQ ID NO: 1 or 2 selected from the list consisting of R309Q+N174NQ+R180*+S181*, R309Q+N174NQ+R180*+T182*, R309Q+N174NQ+R180*+G183*, R309Q+N174NQ+S181*+T182*, R309Q+N174NQ+T182*+G183*, R309Q+N174NQ+N194F+R180*+S181*, R309Q+N174NQ+N194F+R180*+T182*, R309Q+N174NQ+N194F+R180*+G183*, R309Q+N174NQ+N194F+S181*+T182*, R309Q+N174NQ+N194F+T182*+G183*, R309Q+N174NQ+N194Y+R180*+S181*, R309Q+N174NQ+N194Y+R180*+T182*, R309Q+N174NQ+N194Y+R180*+G183*, R309Q+N174NQ+N194Y+S181*+T182*, R309Q+N174NQ+N194Y+T182*+G183* and R309Q+N174NQ+G475K+S243Q+R180*+S181*.

In one embodiment, the variant comprises multiple alterations of the mature polypeptide of SEQ ID NO: 1 or 2 selected from the list consisting of Y48W+N174NQ+R180*+S181*, Y48W+N174NQ+R180*+T182*, Y48W+N174NQ+R180*+G183*, Y48W+N174NQ+S181*+T182*, Y48W+N174NQ+T182*+G183*, Y48W+N174NQ+N194F+R180*+S181*, Y48W+N174NQ+N194F+R180*+T182*, Y48W+N174NQ+N194F+R180*+G183*, Y48W+N174NQ+N194F+S181*+T182*, Y48W+N174NQ+N194F+T182*+G183*, Y48W+N174NQ+N194Y+R180*+S181*, Y48W+N174NQ+N194Y+R180*+T182*, Y48W+N174NQ+N194Y+R180*+G183*, Y48W+N174NQ+N194Y+S181*+T182*, Y48W+N174NQ+N194Y+T182*+G183* and Y48W+N174NQ+G475K+S243Q+R180*+S181*.

In one embodiment, the variant comprises multiple alterations of the mature polypeptide of SEQ ID NO: 1 or 2 selected from the list consisting of V212N+N174NN+R180*+S181*, V212N+N174NN+R180*+T182*, V212N+N174NN+R180*+G183*, V212N+N174NN+S181*+T182*, V212N+N174NN+T182*+G183*, V212N+N174NN+N194F+R180*+S181*, V212N+N174NN+N194F+R180*+T182*, V212N+N174NN+N194F+R180*+G183*, V212N+N174NN+N194F+S181*+T182*, V212N+N174NN+N194F+T182*+G183*, V212N+N174NN+N194Y+R180*+S181*, V212N+N174NN+N194Y+R180*+T182*, V212N+N174NN+N194Y+R180*+G183*, V212N+N174NN+N194Y+S181*+T182*, V212N+N174NN+N194Y+T182*+G183* and V212N+N174NN+G475K+S243Q+R180*+S181*.

In one embodiment, the variant comprises multiple alterations of the mature polypeptide of SEQ ID NO: 1 or 2 selected from the list consisting of V212N+V213Q+R180*+S181*, V212N+V213Q+R180*+T182*, V212N+V213Q+R180*+G183*, V212N+V213Q+S181*+T182*, V212N+V213Q+T182*+G183*, V212N+V213Q+N194F+R180*+S181*, V212N+V213Q+N194F+R180*+T182*, V212N+V213Q+N194F+R180*+G183*, V212N+V213Q+N194F+S181*+T182*, V212N+V213Q+N194F+T182*+G183*, V212N+V213Q+N194Y+R180*+S181*, V212N+V213Q+N194Y+R180*+T182*, V212N+V213Q+N194Y+R180*+G183*, V212N+V213Q+N194Y+S181*+T182*, V212N+V213Q+N194Y+T182*+G183* and V212N+V213Q+G475K+S243Q+R180*+S181*.

In one embodiment, the variant comprises multiple alterations of the mature polypeptide of SEQ ID NO: 1 or 2 selected from the list consisting of M317L+N174NQ+R180*+S181*, M317L+N174NQ+R180*+T182*, M317L+N174NQ+R180*+G183*, M317L+N174NQ+S181*+T182*, M317L+N174NQ+T182*+G183*, M317L+N174NQ+N194F+R180*+S181*, M317L+N174NQ+N194F+R180*+T182*, M317L+N174NQ+N194F+R180*+G183*, M317L+N174NQ+N194F+S181*+T182*, M317L+N174NQ+N194F+T182*+G183*, M317L+N174NQ+N194Y+R180*+S181*, M317L+N174NQ+N194Y+R180*+T182*, M317L+N174NQ+N194Y+R180*+G183*, M317L+N174NQ+N194Y+S181*+T182*, M317L+N174NQ+N194Y+T182*+G183* and M317L+N174NQ+G475K+S243Q+R180*+S181*.

In one embodiment, the variant comprises multiple alterations of the mature polypeptide of SEQ ID NO: 1 or 2 selected from the list consisting of D16Y+K375Q+R180*+S181*, D16Y+K375Q+R180*+T182*, D16Y+K375Q+R180*+G183*, D16Y+K375Q+S181*+T182*, D16Y+K375Q+T182*+G183*, D16Y+K375Q+N194F+R180*+S181*, D16Y+K375Q+N194F+R180*+T182*, D16Y+K375Q+N194F+R180*+G183*, D16Y+K375Q+N194F+S181*+T182*, D16Y+K375Q+N194F+T182*+G183*, D16Y+K375Q+N194Y+R180*+S181*, D16Y+K375Q+N194Y+R180*+T182*, D16Y+K375Q+N194Y+R180*+G183*, D16Y+K375Q+N194Y+S181*+T182*, D16Y+K375Q+N194Y+T182*+G183* and D16Y+K375Q+G475K+S243Q+R180*+S181*.

In one embodiment, the variant comprises multiple alterations of the mature polypeptide of SEQ ID NO: 1 or 2 selected from the list consisting of N19D+Q53R+R180*+S181*, N19D+Q53R+R180*+T182*, N19D+Q53R+R180*+G183*, N19D+Q53R+S181*+T182*, N19D+Q53R+T182*+G183*, N19D+Q53R+N194F+R180*+S181*, N19D+Q53R+N194F+R180*+T182*, N19D+Q53R+N194F+R180*+G183*, N19D+Q53R+N194F+S181*+T182*, N19D+Q53R+N194F+T182*+G183*, N19D+Q53R+N194Y+R180*+S181*, N19D+Q53R+N194Y+R180*+T182*, N19D+Q53R+N194Y+R180*+G183*, N19D+Q53R+N194Y+S181*+T182*, N19D+Q53R+N194Y+T182*+G183* and N19D+Q53R+G475K+S243Q+R180*+S181*.

In one embodiment, the variant comprises multiple alterations of the mature polypeptide of SEQ ID NO: 1 or 2 selected from the list consisting of Y48W+V60A+R180*+S181*, Y48W+V60A+R180*+T182*, Y48W+V60A+R180*+G183*, Y48W+V60A+S181*+T182*, Y48W+V60A+T182*+G183*, Y48W+V60A+N194F+R180*+S181*, Y48W+V60A+N194F+R180*+T182*, Y48W+V60A+N194F+R180*+G183*, Y48W+V60A+N194F+S181*+T182*, Y48W+V60A+N194F+T182*+G183*, Y48W+V60A+N194Y+R180*+S181*, Y48W+V60A+N194Y+R180*+T182*, Y48W+V60A+N194Y+R180*+G183*, Y48W+V60A+N194Y+S181*+T182*, Y48W+V60A+N194Y+T182*+G183* and Y48W+V60A+G475K+S243Q+R180*+S181*. In one embodiment, the variant comprises multiple alterations of the mature polypeptide of SEQ ID NO: 1 or 2 selected from the list consisting of Y48W+F105M+R180*+S181*, Y48W+F105M+R180*+T182*, Y48W+F105M+R180*+G183*, Y48W+F105M+S181*+T182*, Y48W+F105M+T182*+G183*, Y48W+F105M+N194F+R180*+S181*, Y48W+F105M+N194F+R180*+T182*, Y48W+F105M+N194F+R180*+G183*, Y48W+F105M+N194F+S181*+T182*, Y48W+F105M+N194F+T182*+G183*, Y48W+F105M+N194Y+R180*+S181*, Y48W+F105M+N194Y+R180*+T182*, Y48W+F105M+N194Y+R180*+G183*, Y48W+F105M+N194Y+S181*+T182*, Y48W+F105M+N194Y+T182*+G183* and Y48W+F105M+G475K+S243Q+R180*+S181*.

In one embodiment, the variant comprises multiple alterations of the mature polypeptide of SEQ ID NO: 1 or 2 selected from the list consisting of Y48W+L205Y+R180*+S181*, Y48W+L205Y+R180*+T182*, Y48W+L205Y+R180*+G183*, Y48W+L205Y+S181*+T182*, Y48W+L205Y+T182*+G183*, Y48W+L205Y+N194F+R180*+S181*, Y48W+L205Y+N194F+R180*+T182*, Y48W+L205Y+N194F+R180*+G183*, Y48W+L205Y+N194F+S181*+T182*, Y48W+L205Y+N194F+T182*+G183*, Y48W+L205Y+N194Y+R180*+S181*, Y48W+L205Y+N194Y+R180*+T182*, Y48W+L205Y+N194Y+R180*+G183*, Y48W+L205Y+N194Y+S181*+T182*, Y48W+L205Y+N194Y+T182*+G183* and Y48W+L205Y+G475K+S243Q+R180*+S181*.

In one embodiment, the variant comprises multiple alterations of the mature polypeptide of SEQ ID NO: 1 or 2 selected from the list consisting of V60A+L205Y+R180*+S181*, V60A+L205Y+R180*+T182*, V60A+L205Y+R180*+G183*, V60A+L205Y+S181*+T182*, V60A+L205Y+T182*+G183*, V60A+L205Y+N194F+R180*+S181*, V60A+L205Y+N194F+R180*+T182*, V60A+L205Y+N194F+R180*+G183*, V60A+L205Y+N194F+S181*+T182*, V60A+L205Y+N194F+T182*+G183*, V60A+L205Y+N194Y+R180*+S181*, V60A+L205Y+N194Y+R180*+T182*, V60A+L205Y+N194Y+R180*+G183*, V60A+L205Y+N194Y+S181*+T182*, V60A+L205Y+N194Y+T182*+G183* and V60A+L205Y+G475K+S243Q+R180*+S181*.

In one embodiment, the variant comprises multiple alterations of the mature polypeptide of SEQ ID NO: 1 or 2 selected from the list consisting of Y48W+V60A+F105M+R180*+S181*, Y48W+V60A+F105M+R180*+T182*, Y48W+V60A+F105M+R180*+G183*, Y48W+V60A+F105M+S181*+T182*, Y48W+V60A+F105M+T182*+G183*, Y48W+V60A+F105M+N194F+R180*+S181*, Y48W+V60A+F105M+N194F+R180*+T182*, Y48W+V60A+F105M+N194F+R180*+G183*, Y48W+V60A+F105M+N194F+S181*+T182*, Y48W+V60A+F105M+N194F+T182*+G183*, Y48W+V60A+F105M+N194Y+R180*+S181*, Y48W+V60A+F105M+N194Y+R180*+T182*, Y48W+V60A+F105M+N194Y+R180*+G183*, Y48W+V60A+F105M+N194Y+S181*+T182*, Y48W+V60A+F105M+N194Y+T182*+G183* and Y48W+V60A+F105M+G475K+S243Q+R180*+S181*.

In one embodiment, the variant comprises multiple alterations of the mature polypeptide of SEQ ID NO: 1 or 2 selected from the list consisting of Y48W+V60A+L205F+R180*+S181*, Y48W+V60A+L205F+R180*+T182*, Y48W+V60A+L205F+R180*+G183*, Y48W+V60A+L205F+S181*+T182*, Y48W+V60A+L205F+T182*+G183*, Y48W+V60A+L205F+N194F+R180*+S181*, Y48W+V60A+L205F+N194F+R180*+T182*, Y48W+V60A+L205F+N194F+R180*+G183*, Y48W+V60A+L205F+N194F+S181*+T182*, Y48W+V60A+L205F+N194F+T182*+G183*, Y48W+V60A+L205F+N194Y+R180*+S181*, Y48W+V60A+L205F+N194Y+R180*+T182*, Y48W+V60A+L205F+N194Y+R180*+G183*, Y48W+V60A+L205F+N194Y+S181*+T182*, Y48W+V60A+L205F+N194Y+T182*+G183* and Y48W+V60A+L205F+G475K+S243Q+R180*+S181*.

In one embodiment, the variant comprises multiple alterations of the mature polypeptide of SEQ ID NO: 1 or 2 selected from the list consisting of V60A+F105M+L205F+R180*+S181*, V60A+F105M+L205F+R180*+T182*, V60A+F105M+L205F+R180*+G183*, V60A+F105M+L205F+S181*+T182*, V60A+F105M+L205F+T182*+G183*, V60A+F105M+L205F+N194F+R180*+S181*, V60A+F105M+L205F+N194F+R180*+T182*, V60A+F105M+L205F+N194F+R180*+G183*, V60A+F105M+L205F+N194F+S181*+T182*, V60A+F105M+L205F+N194F+T182*+G183*, V60A+F105M+L205F+N194Y+R180*+S181*, V60A+F105M+L205F+N194Y+R180*+T182*, V60A+F105M+L205F+N194Y+R180*+G183*, V60A+F105M+L205F+N194Y+S181*+T182*, V60A+F105M+L205F+N194Y+T182*+G183* and V60A+F105M+L205F+G475K+S243Q+R180*+S181*.

In one embodiment, the variant comprises multiple alterations of the mature polypeptide of SEQ ID NO: 1 or 2 selected from the list consisting of Y48W+V60A+F105M+L205F+R180*+S181*, Y48W+V60A+F105M+L205F+R180*+T182*, Y48W+V60A+F105M+L205F+R180*+G183*, Y48W+V60A+F105M+L205F+S181*+T182*, Y48W+V60A+F105M+L205F+T182*+G183*, Y48W+V60A+F105M+L205F+N194F+R180*+S181*, Y48W+V60A+F105M+L205F+N194F+R180*+T182*, Y48W+V60A+F105M+L205F+N194F+R180*+G183*, Y48W+V60A+F105M+L205F+N194F+S181*+T182*, Y48W+V60A+F105M+L205F+N194F+T182*+G183*, Y48W+V60A+F105M+L205F+N194Y+R180*+S181*, Y48W+V60A+F105M+L205F+N194Y+R180*+T182*, Y48W+V60A+F105M+L205F+N194Y+R180*+G183*, Y48W+V60A+F105M+L205F+N194Y+S181*+T182*, Y48W+V60A+F105M+L205F+N194Y+T182*+G183* and Y48W+V60A+F105M+L205F+G475K+S243Q+R180*+S181*.

In one embodiment, the variant comprises multiple alterations of the mature polypeptide of SEQ ID NO: 1 or 2 selected from the list consisting of Y48W+V60A+L205Y+R180*+S181*, Y48W+V60A+L205Y+R180*+T182*, Y48W+V60A+L205Y+R180*+G183*, Y48W+V60A+L205Y+S181*+T182*, Y48W+V60A+L205Y+T182*+G183*, Y48W+V60A+L205Y+N194F+R180*+S181*, Y48W+V60A+L205Y+N194F+R180*+T182*, Y48W+V60A+L205Y+N194F+R180*+G183*, Y48W+V60A+L205Y+N194F+S181*+T182*, Y48W+V60A+L205Y+N194F+T182*+G183*, Y48W+V60A+L205Y+N194Y+R180*+S181*, Y48W+V60A+L205Y+N194Y+R180*+T182*, Y48W+V60A+L205Y+N194Y+R180*+G183*, Y48W+V60A+L205Y+N194Y+S181*+T182*, Y48W+V60A+L205Y+N194Y+T182*+G183* and Y48W+V60A+L205Y+G475K+S243Q+R180*+S181*.

In one embodiment, the variant comprises multiple alterations of the mature polypeptide of SEQ ID NO: 1 or 2 selected from the list consisting of V60A+F105M+L205Y+R180*+S181*, V60A+F105M+L205Y+R180*+T182*, V60A+F105M+L205Y+R180*+G183*, V60A+F105M+L205Y+S181*+T182*, V60A+F105M+L205Y+T182*+G183*, V60A+F105M+L205Y+N194F+R180*+S181*, V60A+F105M+L205Y+N194F+R180*+T182*, V60A+F105M+L205Y+N194F+R180*+G183*, V60A+F105M+L205Y+N194F+S181*+T182*, V60A+F105M+L205Y+N194F+T182*+G183*, V60A+F105M+L205Y+N194Y+

R180*+S181*, V60A+F105M+L205Y+N194Y+R180*+T182*, V60A+F105M+L205Y+N194Y+R180*+G183*, V60A+F105M+L205Y+N194Y+S181*+T182*, V60A+F105M+L205Y+N194Y+T182*+G183* and V60A+F105M+L205Y+G475K+S243Q+R180*+S181*.

In one embodiment, the variant comprises multiple alterations of the mature polypeptide of SEQ ID NO: 1 or 2 selected from the list consisting of Y48W+V60A+F105M+L205Y+R180*+S181*, Y48W+V60A+F105M+L205Y+R180*+T182*, Y48W+V60A+F105M+L205Y+R180*+G183*, Y48W+V60A+F105M+L205Y+S181*+T182*, Y48W+V60A+F105M+L205Y+T182*+G183*, Y48W+V60A+F105M+L205Y+N194F+R180*+S181*, Y48W+V60A+F105M+L205Y+N194F+R180*+T182*, Y48W+V60A+F105M+L205Y+N194F+R180*+G183*, Y48W+V60A+F105M+L205Y+N194F+S181*+T182*, Y48W+V60A+F105M+L205Y+N194F+T182*+G183*, Y48W+V60A+F105M+L205Y+N194Y+R180*+S181*, Y48W+V60A+F105M+L205Y+N194Y+R180*+T182*, Y48W+V60A+F105M+L205Y+N194Y+R180*+G183*, Y48W+V60A+F105M+L205Y+N194Y+S181*+T182*, Y48W+V60A+F105M+L205Y+N194Y+T182*+G183* and Y48W+V60A+F105M+L205Y+G475K+S243Q+R180*+S181*.

In one embodiment, the variant comprises multiple alterations of the mature polypeptide of SEQ ID NO: 1 or 2 selected from the list consisting of P124D+S125P+R180*+S181*, P124D+S125P+R180*+T182*, P124D+S125P+R180*+G183*, P124D+S125P+S181*+T182*, P124D+S125P+T182*+G183*, P124D+S125P+N194F+R180*+S181*, P124D+S125P+N194F+R180*+T182*, P124D+S125P+N194F+R180*+G183*, P124D+S125P+N194F+S181*+T182*, P124D+S125P+N194F+T182*+G183*, P124D+S125P+N194Y+R180*+S181*, P124D+S125P+N194Y+R180*+T182*, P124D+S125P+N194Y+R180*+G183*, P124D+S125P+N194Y+S181*+T182*, P124D+S125P+N194Y+T182*+G183* and P124D+S125P+G475K+S243Q+R180*+S181*.

In one embodiment, the variant comprises multiple alterations of the mature polypeptide of SEQ ID NO: 1 or 2 selected from the list consisting of P124D+S125N+R180*+S181*, P124D+S125N+R180*+T182*, P124D+S125N+R180*+G183*, P124D+S125N+S181*+T182*, P124D+S125N+T182*+G183*, P124D+S125N+N194F+R180*+S181*, P124D+S125N+N194F+R180*+T182*, P124D+S125N+N194F+R180*+G183*, P124D+S125N+N194F+S181*+T182*, P124D+S125N+N194F+T182*+G183*, P124D+S125N+N194Y+R180*+S181*, P124D+S125N+N194Y+R180*+T182*, P124D+S125N+N194Y+R180*+G183*, P124D+S125N+N194Y+S181*+T182*, P124D+S125N+N194Y+T182*+G183* and P124D+S125N+G475K+S243Q+R180*+S181*.

In one embodiment, the variant comprises multiple alterations of the mature polypeptide of SEQ ID NO: 1 or 2 selected from the list consisting of S125N+N174NN+R180*+S181*, S125N+N174NN+R180*+T182*, S125N+N174NN+R180*+G183*, S125N+N174NN+S181*+T182*, S125N+N174NN+T182*+G183*, S125N+N174NN+N194F+R180*+S181*, S125N+N174NN+N194F+R180*+T182*, S125N+N174NN+N194F+R180*+G183*, S125N+N174NN+N194F+S181*+T182*, S125N+N174NN+N194F+T182*+G183*, S125N+N174NN+N194Y+R180*+S181*, S125N+N174NN+N194Y+R180*+T182*, S125N+N174NN+N194Y+R180*+G183*, S125N+N174NN+N194Y+S181*+T182*, S125N+N174NN+N194Y+T182*+G183* and S125N+N174NN+G475K+S243Q+R180*+S181*.

In one embodiment, the variant comprises multiple alterations of the mature polypeptide of SEQ ID NO: 1 or 2 selected from the list consisting of K172Q+N174NQ+R180*+S181*, K172Q+N174NQ+R180*+T182*, K172Q+N174NQ+R180*+G183*, K172Q+N174NQ+S181*+T182*, K172Q+N174NQ+T182*+G183*, K172Q+N174NQ+N194F+R180*+S181*, K172Q+N174NQ+N194F+R180*+T182*, K172Q+N174NQ+N194F+R180*+G183*, K172Q+N174NQ+N194F+S181*+T182*, K172Q+N174NQ+N194F+T182*+G183*, K172Q+N174NQ+N194Y+R180*+S181*, K172Q+N174NQ+N194Y+R180*+T182*, K172Q+N174NQ+N194Y+R180*+G183*, K172Q+N174NQ+N194Y+S181*+T182*, K172Q+N174NQ+N194Y+T182*+G183* and K172Q+N174NQ+G475K+S243Q+R180*+S181*.

In one embodiment, the variant comprises multiple alterations of the mature polypeptide of SEQ ID NO: 1 or 2 selected from the list consisting of K172Q+L173F+R180*+S181*, K172Q+L173F+R180*+T182*, K172Q+L173F+R180*+G183*, K172Q+L173F+S181*+T182*, K172Q+L173F+T182*+G183*, K172Q+L173F+N194F+R180*+S181*, K172Q+L173F+N194F+R180*+T182*, K172Q+L173F+N194F+R180*+G183*, K172Q+L173F+N194F+S181*+T182*, K172Q+L173F+N194F+T182*+G183*, K172Q+L173F+N194Y+R180*+S181*, K172Q+L173F+N194Y+R180*+T182*, K172Q+L173F+N194Y+R180*+G183*, K172Q+L173F+N194Y+S181*+T182*, K172Q+L173F+N194Y+T182*+G183* and K172Q+L173F+G475K+S243Q+R180*+S181*.

In one embodiment, the variant comprises multiple alterations of the mature polypeptide of SEQ ID NO: 1 or 2 selected from the list consisting of K172Q+L173F+N174NQ+R180*+S181*, K172Q+L173F+N174NQ+R180*+T182*, K172Q+L173F+N174NQ+R180*+G183*, K172Q+L173F+N174NQ+S181*+T182*, K172Q+L173F+N174NQ+T182*+G183*, K172Q+L173F+N174NQ+N194F+R180*+S181*, K172Q+L173F+N174NQ+N194F+R180*+T182*, K172Q+L173F+N174NQ+N194F+R180*+G183*, K172Q+L173F+N174NQ+N194F+S181*+T182*, K172Q+L173F+N174NQ+N194F+T182*+G183*, K172Q+L173F+N174NQ+N194Y+R180*+S181*, K172Q+L173F+N174NQ+N194Y+R180*+T182*, K172Q+L173F+N174NQ+N194Y+R180*+G183*, K172Q+L173F+N174NQ+N194Y+S181*+T182*, K172Q+L173F+N174NQ+N194Y+T182*+G183* and K172Q+L173F+N174NQ+G475K+S243Q+R180*+S181*.

In one embodiment, the variant comprises multiple alterations of the mature polypeptide of SEQ ID NO: 1 or 2 selected from the list consisting of Y242F+F266Y+R180*+S181*, Y242F+F266Y+R180*+T182*, Y242F+F266Y+R180*+G183*, Y242F+F266Y+S181*+T182*, Y242F+F266Y+T182*+G183*, Y242F+F266Y+N194F+R180*+S181*, Y242F+F266Y+N194F+R180*+T182*, Y242F+F266Y+N194F+R180*+G183*, Y242F+F266Y+N194F+S181*+T182*, Y242F+F266Y+N194F+T182*+G183*, Y242F+F266Y+N194Y+R180*+S181*, Y242F+F266Y+N194Y+R180*+T182*, Y242F+F266Y+N194Y+R180*+G183*, Y242F+F266Y+N194Y+S181*+T182*, Y242F+F266Y+N194Y+T182*+G183* and Y242F+F266Y+G475K+S243Q+R180*+S181*.

In one embodiment, the variant comprises multiple alterations of the mature polypeptide of SEQ ID NO: 1 or 2 selected from the list consisting of Y269N+N294Y+R180*+S181*, Y269N+N294Y+R180*+T182*, Y269N+N294Y+R180*+G183*, Y269N+N294Y+S181*+T182*, Y269N+N294Y+T182*+G183*, Y269N+N294Y+N194F+R180*+S181*, Y269N+N294Y+N194F+R180*+T182*, Y269N+

N294Y+N194F+R180*+G183*, Y269N+N294Y+N194F+S181*+T182*, Y269N+N294Y+N194F+T182*+G183*, Y269N+N294Y+N194Y+R180*+S181*, Y269N+N294Y+N194Y+R180*+T182*, Y269N+N294Y+N194Y+R180*+G183*, Y269N+N294Y+N194Y+S181*+T182*, Y269N+N294Y+N194Y+T182*+G183* and Y269N+N294Y+G475K+S243Q+R180*+S181*.

In one embodiment, the variant comprises multiple alterations of the mature polypeptide of SEQ ID NO: 1 or 2 selected from the list consisting of G283S+L323H+R180*+S181*, G283S+L323H+R180*+T182*, G283S+L323H+R180*+G183*, G283S+L323H+S181*+T182*, G283S+L323H+T182*+G183*, G283S+L323H+N194F+R180*+S181*, G283S+L323H+N194F+R180*+T182*, G283S+L323H+N194F+R180*+G183*, G283S+L323H+N194F+S181*+T182*, G283S+L323H+N194F+T182*+G183*, G283S+L323H+N194Y+R180*+S181*, G283S+L323H+N194Y+R180*+T182*, G283S+L323H+N194Y+R180*+G183*, G283S+L323H+N194Y+S181*+T182*, G283S+L323H+N194Y+T182*+G183* and G283S+L323H+G475K+S243Q+R180*+S181*.

In other embodiments, the variant comprises or consists of the following alterations of the mature polypeptide of SEQ ID NO: 1 (individual embodiments are separated by semicolon): D16Y+R180*+S181*; D16Y+R180*+T182*; D16Y+R180*+G183*; D16Y+S181*+T182*; D16Y+T182*+G183*; D16Y+N194F+R180*+S181*; D16Y+N194F+R180*+T182*; D16Y+N194F+R180*+G183*; D16Y+N194F+S181*+T182*; D16Y+N194F+T182*+G183*; D16Y+N194Y+R180*+S181*; D16Y+N194Y+R180*+T182*; D16Y+N194Y+R180*+G183*; D16Y+N194Y+S181*+T182*; D16Y+N194Y+T182*+G183*; D16Y+G475K+S243Q+R180*+S181*; N19D+R180*+S181*; N19D+R180*+T182*; N19D+R180*+G183*; N19D+S181*+T182*; N19D+T182*+G183*; N19D+N194F+R180*+S181*; N19D+N194F+R180*+T182*; N19D+N194F+R180*+G183*; N19D+N194F+S181*+T182*; N19D+N194F+T182*+G183*; N19D+N194Y+R180*+S181*; N19D+N194Y+R180*+T182*; N19D+N194Y+R180*+G183*; N19D+N194Y+S181*+T182*; N19D+N194Y+T182*+G183*; N19D+G475K+S243Q+R180*+S181*; Y48W+R180*+S181*; Y48W+R180*+T182*; Y48W+R180*+G183*; Y48W+S181*+T182*; Y48W+T182*+G183*; Y48W+N194F+R180*+S181*; Y48W+N194F+R180*+T182*; Y48W+N194F+R180*+G183*; Y48W+N194F+S181*+T182*; Y48W+N194F+T182*+G183*; Y48W+N194Y+R180*+S181*; Y48W+N194Y+R180*+T182*; Y48W+N194Y+R180*+G183*; Y48W+N194Y+S181*+T182*; Y48W+N194Y+T182*+G183*; Y48W+G475K+S243Q+R180*+S181*; Y48F+R180*+S181*; Y48F+R180*+T182*; Y48F+R180*+G183*; Y48F+S181*+T182*; Y48F+T182*+G183*; Y48F+N194F+R180*+S181*; Y48F+N194F+R180*+T182*; Y48F+N194F+R180*+G183*; Y48F+N194F+S181*+T182*; Y48F+N194F+T182*+G183*; Y48F+N194Y+R180*+S181*; Y48F+N194Y+R180*+T182*; Y48F+N194Y+R180*+G183*; Y48F+N194Y+S181*+T182*; Y48F+N194Y+T182*+G183*; Y48F+G475K+S243Q+R180*+S181*; Q53R+R180*+S181*; Q53R+R180*+T182*; Q53R+R180*+G183*; Q53R+S181*+T182*; Q53R+T182*+G183*; Q53R+N194F+R180*+S181*; Q53R+N194F+R180*+T182*; Q53R+N194F+R180*+G183*; Q53R+N194F+S181*+T182*; Q53R+N194F+T182*+G183*; Q53R+N194Y+R180*+S181*; Q53R+N194Y+R180*+T182*; Q53R+N194Y+R180*+G183*; Q53R+N194Y+S181*+T182*; Q53R+N194Y+T182*+G183*; Q53R+G475K+S243Q+R180*+S181*; V60A+R180*+S181*; V60A+R180*+T182*; V60A+R180*+G183*; V60A+S181*+T182*; V60A+T182*+G183*; V60A+N194F+R180*+S181*; V60A+N194F+R180*+T182*; V60A+N194F+R180*+G183*; V60A+N194F+S181*+T182*; V60A+N194F+T182*+G183*; V60A+N194Y+R180*+S181*; V60A+N194Y+R180*+T182*; V60A+N194Y+R180*+G183*; V60A+N194Y+S181*+T182*; V60A+N194Y+T182*+G183*; V60A+G475K+S243Q+R180*+S181*; F105M+R180*+S181*; F105M+R180*+T182*; F105M+R180*+G183*; F105M+S181*+T182*; F105M+T182*+G183*; F105M+N194F+R180*+S181*; F105M+N194F+R180*+T182*; F105M+N194F+R180*+G183*; F105M+N194F+S181*+T182*; F105M+N194F+T182*+G183*; F105M+N194Y+R180*+S181*; F105M+N194Y+R180*+T182*; F105M+N194Y+R180*+G183*; F105M+N194Y+S181*+T182*; F105M+N194Y+T182*+G183*; F105M+G475K+S243Q+R180*+S181*; F116W+R180*+S181*; F116W+R180*+T182*; F116W+R180*+G183*; F116W+S181*+T182*; F116W+T182*+G183*; F116W+N194F+R180*+S181*; F116W+N194F+R180*+T182*; F116W+N194F+R180*+G183*; F116W+N194F+S181*+T182*; F116W+N194F+T182*+G183*; F116W+N194Y+R180*+S181*; F116W+N194Y+R180*+T182*; F116W+N194Y+R180*+G183*; F116W+N194Y+S181*+T182*; F116W+N194Y+T182*+G183*; F116W+G475K+S243Q+R180*+S181*; P124*+R180*+S181*; P124*+R180*+T182*; P124*+R180*+G183*; P124*+S181*+T182*; P124*+T182*+G183*; P124*+N194F+R180*+S181*; P124*+N194F+R180*+T182*; P124*+N194F+R180*+G183*; P124*+N194F+S181*+T182*; P124*+N194F+T182*+G183*; P124*+N194Y+R180*+S181*; P124*+N194Y+R180*+T182*; P124*+N194Y+R180*+G183*; P124*+N194Y+S181*+T182*; P124*+N194Y+T182*+G183*; P124*+G475K+S243Q+R180*+S181*; P124D+R180*+S181*; P124D+R180*+T182*; P124D+R180*+G183*; P124D+S181*+T182*; P124D+T182*+G183*; P124D+N194F+R180*+S181*; P124D+N194F+R180*+T182*; P124D+N194F+R180*+G183*; P124D+N194F+S181*+T182*; P124D+N194F+T182*+G183*; P124D+N194Y+R180*+S181*; P124D+N194Y+R180*+T182*; P124D+N194Y+R180*+G183*; P124D+N194Y+S181*+T182*; P124D+N194Y+T182*+G183*; P124D+G475K+S243Q+R180*+S181*; P124S+R180*+S181*; P124S+R180*+T182*; P124S+R180*+G183*; P124S+S181*+T182*; P124S+T182*+G183*; P124S+N194F+R180*+S181*; P124S+N194F+R180*+T182*; P124S+N194F+R180*+G183*; P124S+N194F+S181*+T182*; P124S+N194F+T182*+G183*; P124S+N194Y+R180*+S181*; P124S+N194Y+R180*+T182*; P124S+N194Y+R180*+G183*; P124S+N194Y+S181*+T182*; P124S+N194Y+T182*+G183*; P124S+G475K+S243Q+R180*+S181*; P124T+R180*+S181*; P124T+R180*+T182*; P124T+R180*+G183*; P124T+S181*+T182*; P124T+T182*+G183*; P124T+N194F+R180*+S181*; P124T+N194F+R180*+T182*; P124T+N194F+R180*+G183*; P124T+N194F+S181*+T182*; P124T+N194F+T182*+G183*; P124T+N194Y+R180*+S181*; P124T+N194Y+R180*+T182*; P124T+N194Y+R180*+G183*; P124T+N194Y+S181*+T182*; P124T+N194Y+T182*+G183*; P124T+G475K+S243Q+R180*+S181*; S125N+R180*+S181*; S125N+R180*+T182*; S125N+R180*+G183*; S125N+S181*+T182*; S125N+T182*+G183*; S125N+N194F+R180*+S181*; S125N+N194F+R180*+T182*; S125N+N194F+R180*+G183*; S125N+N194F+S181*+T182*; S125N+N194F+T182*+G183*; S125N+N194Y+R180*+S181*; S125N+N194Y+R180*+T182*; S125N+N194Y+R180*+G183*; S125N+N194Y+

S181*+T182*; S125N+N194Y+T182*+G183*; S125N+G475K+S243Q+R180*+S181*; S125P+R180*+S181*; S125P+R180*+T182*; S125P+R180*+G183*; S125P+S181*+T182*; S125P+T182*+G183*; S125P+N194F+R180*+S181*; S125P+N194F+R180*+T182*; S125P+N194F+R180*+G183*; S125P+N194F+S181*+T182*; S125P+N194F+T182*+G183*; S125P+N194Y+R180*+S181*; S125P+N194Y+R180*+T182*; S125P+N194Y+R180*+G183*; S125P+N194Y+S181*+T182*; S125P+N194Y+T182*+G183*; S125P+G475K+S243Q+R180*+S181*; N128F+R180*+S181*; N128F+R180*+T182*; N128F+R180*+G183*; N128F+S181*+T182*; N128F+T182*+G183*; N128F+N194F+R180*+S181*; N128F+N194F+R180*+T182*; N128F+N194F+R180*+G183*; N128F+N194F+S181*+T182*; N128F+N194F+T182*+G183*; N128F+N194Y+R180*+S181*; N128F+N194Y+R180*+T182*; N128F+N194Y+R180*+G183*; N128F+N194Y+S181*+T182*; N128F+N194Y+T182*+G183*; N128F+G475K+S243Q+R180*+S181*; N128H+R180*+S181*; N128H+R180*+T182*; N128H+R180*+G183*; N128H+S181*+T182*; N128H+T182*+G183*; N128H+N194F+R180*+S181*; N128H+N194F+R180*+T182*; N128H+N194F+R180*+G183*; N128H+N194F+S181*+T182*; N128H+N194F+T182*+G183*; N128H+N194Y+R180*+S181*; N128H+N194Y+R180*+T182*; N128H+N194Y+R180*+G183*; N128H+N194Y+S181*+T182*; N128H+N194Y+T182*+G183*; N128H+G475K+S243Q+R180*+S181*; N128I+R180*+S181*; N128I+R180*+T182*; N128I+R180*+G183*; N128I+S181*+T182*; N128I+T182*+G183*; N128I+N194F+R180*+S181*; N128I+N194F+R180*+T182*; N128I+N194F+R180*+G183*; N128I+N194F+S181*+T182*; N128I+N194F+T182*+G183*; N128I+N194Y+R180*+S181*; N128I+N194Y+R180*+T182*; N128I+N194Y+R180*+G183*; N128I+N194Y+S181*+T182*; N128I+N194Y+T182*+G183*; N128I+G475K+S243Q+R180*+S181*; N128K+R180*+S181*; N128K+R180*+T182*; N128K+R180*+G183*; N128K+S181*+T182*; N128K+T182*+G183*; N128K+N194F+R180*+S181*; N128K+N194F+R180*+T182*; N128K+N194F+R180*+G183*; N128K+N194F+S181*+T182*; N128K+N194F+T182*+G183*; N128K+N194Y+R180*+S181*; N128K+N194Y+R180*+T182*; N128K+N194Y+R180*+G183*; N128K+N194Y+S181*+T182*; N128K+N194Y+T182*+G183*; N128K+G475K+S243Q+R180*+S181*; N128R+R180*+S181*; N128R+R180*+T182*; N128R+R180*+G183*; N128R+S181*+T182*; N128R+T182*+G183*; N128R+N194F+R180*+S181*; N128R+N194F+R180*+T182*; N128R+N194F+R180*+G183*; N128R+N194F+S181*+T182*; N128R+N194F+T182*+G183*; N128R+N194Y+R180*+S181*; N128R+N194Y+R180*+T182*; N128R+N194Y+R180*+G183*; N128R+N194Y+S181*+T182*; N128R+N194Y+T182*+G183*; N128R+G475K+S243Q+R180*+S181*; T131D+R180*+S181*; T131 D+R180*+T182*; T131 D+R180*+G183*; T131D+S181*+T182*; T131D+T182*+G183*; T131D+N194F+R180*+S181*; T131D+N194F+R180*+T182*; T131D+N194F+R180*+G183*; T131D+N194F+S181*+T182*; T131D+N194F+T182*+G183*; T131D+N194Y+R180*+S181*; T131D+N194Y+R180*+T182*; T131D+N194Y+R180*+G183*; T131D+N194Y+S181*+T182*; T131D+N194Y+T182*+G183*; T131 D+G475K+S243Q+R180*+S181*; T131E+R180*+S181*; T131E+R180*+T182*; T131E+R180*+G183*; T131E+S181*+T182*; T131E+T182*+G183*; T131E+N194F+R180*+S181*; T131E+N194F+R180*+T182*; T131E+N194F+R180*+G183*; T131E+N194F+S181*+T182*; T131E+N194F+T182*+G183*; T131E+N194Y+R180*+S181*; T131E+N194Y+R180*+T182*; T131E+N194Y+R180*+G183*; T131E+N194Y+S181*+T182*; T131E+N194Y+T182*+G183*; T131E+G475K+S243Q+R180*+S181*; T131L+R180*+S181*; T131L+R180*+T182*; T131L+R180*+G183*; T131L+S181*+T182*; T131L+T182*+G183*; T131L+N194F+R180*+S181*; T131L+N194F+R180*+T182*; T131L+N194F+R180*+G183*; T131L+N194F+S181*+T182*; T131L+N194F+T182*+G183*; T131L+N194Y+R180*+S181*; T131L+N194Y+R180*+T182*; T131L+N194Y+R180*+G183*; T131L+N194Y+S181*+T182*; T131L+N194Y+T182*+G183*; T131 L+G475K+S243Q+R180*+S181*; G133D+R180*+S181*; G133D+R180*+T182*; G133D+R180*+G183*; G133D+S181*+T182*; G133D+T182*+G183*; G133D+N194F+R180*+S181*; G133D+N194F+R180*+T182*; G133D+N194F+R180*+G183*; G133D+N194F+S181*+T182*; G133D+N194F+T182*+G183*; G133D+N194Y+R180*+S181*; G133D+N194Y+R180*+T182*; G133D+N194Y+R180*+G183*; G133D+N194Y+S181*+T182*; G133D+N194Y+T182*+G183*; G133D+G475K+S243Q+R180*+S181*; K172Q+R180*+S181*; K172Q+R180*+T182*; K172Q+R180*+G183*; K172Q+S181*+T182*; K172Q+T182*+G183*; K172Q+N194F+R180*+S181*; K172Q+N194F+R180*+T182*; K172Q+N194F+R180*+G183*; K172Q+N194F+S181*+T182*; K172Q+N194F+T182*+G183*; K172Q+N194Y+R180*+S181*; K172Q+N194Y+R180*+T182*; K172Q+N194Y+R180*+G183*; K172Q+N194Y+S181*+T182*; K172Q+N194Y+T182*+G183*; K172Q+G475K+S243Q+R180*+S181*; L173F+R180*+S181*; L173F+R180*+T182*; L173F+R180*+G183*; L173F+S181*+T182*; L173F+T182*+G183*; L173F+N194F+R180*+S181*; L173F+N194F+R180*+T182*; L173F+N194F+R180*+G183*; L173F+N194F+S181*+T182*; L173F+N194F+T182*+G183*; L173F+N194Y+R180*+S181*; L173F+N194Y+R180*+T182*; L173F+N194Y+R180*+G183*; L173F+N194Y+S181*+T182*; L173F+N194Y+T182*+G183*; L173F+G475K+S243Q+R180*+S181*; L173Y+R180*+S181*; L173Y+R180*+T182*; L173Y+R180*+G183*; L173Y+S181*+T182*; L173Y+T182*+G183*; L173Y+N194F+R180*+S181*; L173Y+N194F+R180*+T182*; L173Y+N194F+R180*+G183*; L173Y+N194F+S181*+T182*; L173Y+N194F+T182*+G183*; L173Y+N194Y+R180*+S181*; L173Y+N194Y+R180*+T182*; L173Y+N194Y+R180*+G183*; L173Y+N194Y+S181*+T182*; L173Y+N194Y+T182*+G183*; L173Y+G475K+S243Q+R180*+S181*; N174NQ+R180*+S181*; N174NQ+R180*+T182*; N174NQ+R180*+G183*; N174NQ+S181*+T182*; N174NQ+T182*+G183*; N174NQ+N194F+R180*+S181*; N174NQ+N194F+R180*+T182*; N174NQ+N194F+R180*+G183*; N174NQ+N194F+S181*+T182*; N174NQ+N194F+T182*+G183*; N174NQ+N194Y+R180*+S181*; N174NQ+N194Y+R180*+T182*; N174NQ+N194Y+R180*+G183*; N174NQ+N194Y+S181*+T182*; N174NQ+N194Y+T182*+G183*; N174NQ+G475K+S243Q+R180*+S181*; N174NN+R180*+S181*; N174NN+R180*+T182*; N174NN+R180*+G183*; N174NN+S181*+T182*; N174NN+T182*+G183*; N174NN+N194F+R180*+S181*; N174NN+N194F+R180*+T182*; N174NN+N194F+R180*+G183*; N174NN+N194F+S181*+T182*; N174NN+N194F+T182*+G183*; N174NN+N194Y+R180*+S181*; N174NN+N194Y+R180*+T182*; N174NN+N194Y+R180*+G183*; N174NN+N194Y+S181*+T182*; N174NN+N194Y+T182*+G183*; N174NN+G475K+S243Q+R180*+S181*; N174NE+R180*+S181*; N174NE+R180*+T182*; N174NE+R180*+

G183*; N174NE+S181*+T182*; N174NE+T182*+G183*; N174NE+N194F+R180*+S181*; N174NE+N194F+R180*+T182*; N174NE+N194F+R180*+G183*; N174NE+N194F+S181*+T182*; N174NE+N194F+T182*+G183*; N174NE+N194Y+R180*+S181*; N174NE+N194Y+R180*+T182*; N174NE+N194Y+R180*+G183*; N174NE+N194Y+S181*+T182*; N174NE+N194Y+T182*+G183*; N174NE+G475K+S243Q+R180*+S181*; N174ND+R180*+S181*; N174ND+R180*+T182*; N174ND+R180*+G183*; N174ND+S181*+T182*; N174ND+T182*+G183*; N174ND+N194F+R180*+S181*; N174ND+N194F+R180*+T182*; N174ND+N194F+R180*+G183*; N174ND+N194F+S181*+T182*; N174ND+N194F+T182*+G183*; N174ND+N194Y+R180*+S181*; N174ND+N194Y+R180*+T182*; N174ND+N194Y+R180*+G183*; N174ND+N194Y+S181*+T182*; N174ND+N194Y+T182*+G183*; N174ND+G475K+S243Q+R180*+S181*; K178L+R180*+S181*; K178L+R180*+T182*; K178L+R180*+G183*; K178L+S181*+T182*; K178L+T182*+G183*; K178L+N194F+R180*+S181*; K178L+N194F+R180*+T182*; K178L+N194F+R180*+G183*; K178L+N194F+S181*+T182*; K178L+N194F+T182*+G183*; K178L+N194Y+R180*+S181*; K178L+N194Y+R180*+T182*; K178L+N194Y+R180*+G183*; K178L+N194Y+S181*+T182*; K178L+N194Y+T182*+G183*; K178L+G475K+S243Q+R180*+S181*; A185F+R180*+S181*; A185F+R180*+T182*; A185F+R180*+G183*; A185F+S181*+T182*; A185F+T182*+G183*; A185F+N194F+R180*+S181*; A185F+N194F+R180*+T182*; A185F+N194F+R180*+G183*; A185F+N194F+S181*+T182*; A185F+N194F+T182*+G183*; A185F+N194Y+R180*+S181*; A185F+N194Y+R180*+T182*; A185F+N194Y+R180*+G183*; A185F+N194Y+S181*+T182*; A185F+N194Y+T182*+G183*; A185F+G475K+S243Q+R180*+S181*; A185H+R180*+S181*; A185H+R180*+T182*; A185H+R180*+G183*; A185H+S181*+T182*; A185H+T182*+G183*; A185H+N194F+R180*+S181*; A185H+N194F+R180*+T182*; A185H+N194F+R180*+G183*; A185H+N194F+S181*+T182*; A185H+N194F+T182*+G183*; A185H+N194Y+R180*+S181*; A185H+N194Y+R180*+T182*; A185H+N194Y+R180*+G183*; A185H+N194Y+S181*+T182*; A185H+N194Y+T182*+G183*; A185H+G475K+S243Q+R180*+S181*; A185L+R180*+S181*; A185L+R180*+T182*; A185L+R180*+G183*; A185L+S181*+T182*; A185L+T182*+G183*; A185L+N194F+R180*+S181*; A185L+N194F+R180*+T182*; A185L+N194F+R180*+G183*; A185L+N194F+S181*+T182*; A185L+N194F+T182*+G183*; A185L+N194Y+R180*+S181*; A185L+N194Y+R180*+T182*; A185L+N194Y+R180*+G183*; A185L+N194Y+S181*+T182*; A185L+N194Y+T182*+G183*; A185L+G475K+S243Q+R180*+S181*; A185I+R180*+S181*; A185I+R180*+T182*; A185I+R180*+G183*; A185I+S181*+T182*; A185I+T182*+G183*; A185I+N194F+R180*+S181*; A185I+N194F+R180*+T182*; A185I+N194F+R180*+G183*; A185I+N194F+S181*+T182*; A185I+N194F+T182*+G183*; A185I+N194Y+R180*+S181*; A185I+N194Y+R180*+T182*; A185I+N194Y+R180*+G183*; A185I+N194Y+S181*+T182*; A185I+N194Y+T182*+G183*; A185I+G475K+S243Q+R180*+S181*; A185P+R180*+S181*; A185P+R180*+T182*; A185P+R180*+G183*; A185P+S181*+T182*; A185P+T182*+G183*; A185P+N194F+R180*+S181*; A185P+N194F+R180*+T182*; A185P+N194F+R180*+G183*; A185P+N194F+S181*+T182*; A185P+N194F+T182*+G183*; A185P+N194Y+R180*+S181*; A185P+N194Y+R180*+T182*; A185P+N194Y+R180*+G183*; A185P+N194Y+S181*+T182*; A185P+N194Y+T182*+G183*; A185P+G475K+S243Q+R180*+S181*; E189P+R180*+S181*; E189P+R180*+T182*; E189P+R180*+G183*; E189P+S181*+T182*; E189P+T182*+G183*; E189P+N194F+R180*+S181*; E189P+N194F+R180*+T182*; E189P+N194F+R180*+G183*; E189P+N194F+S181*+T182*; E189P+N194F+T182*+G183*; E189P+N194Y+R180*+S181*; E189P+N194Y+R180*+T182*; E189P+N194Y+R180*+G183*; E189P+N194Y+S181*+T182*; E189P+N194Y+T182*+G183*; E189P+G475K+S243Q+R180*+S181*; N194F+R180*+S181*; N194F+R180*+T182*; N194F+R180*+G183*; N194F+S181*+T182*; N194F+T182*+G183*; N194F+G475K+S243Q+R180*+S181*; N194Y+R180*+S181*; N194Y+R180*+T182*; N194Y+R180*+G183*; N194Y+S181*+T182*; N194Y+T182*+G183*; N194Y+G475K+S243Q+R180*+S181*; N194H+R180*+S181*; N194H+R180*+T182*; N194H+R180*+G183*; N194H+S181*+T182*; N194H+T182*+G183*; N194H+G475K+S243Q+R180*+S181*; N194L+R180*+S181*; N194L+R180*+T182*; N194L+R180*+G183*; N194L+S181*+T182*; N194L+T182*+G183*; N194L+G475K+S243Q+R180*+S181*; N194I+R180*+S181*; N194I+R180*+T182*; N194I+R180*+G183*; N194I+S181*+T182*; N194I+T182*+G183*; N194I+G475K+S243Q+R180*+S181*; A203S+R180*+S181*; A203S+R180*+T182*; A203S+R180*+G183*; A203S+S181*+T182*; A203S+T182*+G183*; A203S+N194F+R180*+S181*; A203S+N194F+R180*+T182*; A203S+N194F+R180*+G183*; A203S+N194F+S181*+T182*; A203S+N194F+T182*+G183*; A203S+N194Y+R180*+S181*; A203S+N194Y+R180*+T182*; A203S+N194Y+R180*+G183*; A203S+N194Y+S181*+T182*; A203S+N194Y+T182*+G183*; A203S+G475K+S243Q+R180*+S181*; A203T+R180*+S181*; A203T+R180*+T182*; A203T+R180*+G183*; A203T+S181*+T182*; A203T+T182*+G183*; A203T+N194F+R180*+S181*; A203T+N194F+R180*+T182*; A203T+N194F+R180*+G183*; A203T+N194F+S181*+T182*; A203T+N194F+T182*+G183*; A203T+N194Y+R180*+S181*; A203T+N194Y+R180*+T182*; A203T+N194Y+R180*+G183*; A203T+N194Y+S181*+T182*; A203T+N194Y+T182*+G183*; A203T+G475K+S243Q+R180*+S181*; L205F+R180*+S181*; L205F+R180*+T182*; L205F+R180*+G183*; L205F+S181*+T182*; L205F+T182*+G183*; L205F+N194F+R180*+S181*; L205F+N194F+R180*+T182*; L205F+N194F+R180*+G183*; L205F+N194F+S181*+T182*; L205F+N194F+T182*+G183*; L205F+N194Y+R180*+S181*; L205F+N194Y+R180*+T182*; L205F+N194Y+R180*+G183*; L205F+N194Y+S181*+T182*; L205F+N194Y+T182*+G183*; L205F+G475K+S243Q+R180*+S181*; L205Y+R180*+S181*; L205Y+R180*+T182*; L205Y+R180*+G183*; L205Y+S181*+T182*; L205Y+T182*+G183*; L205Y+N194F+R180*+S181*; L205Y+N194F+R180*+T182*; L205Y+N194F+R180*+G183*; L205Y+N194F+S181*+T182*; L205Y+N194F+T182*+G183*; L205Y+N194Y+R180*+S181*; L205Y+N194Y+R180*+T182*; L205Y+N194Y+R180*+G183*; L205Y+N194Y+S181*+T182*; L205Y+N194Y+T182*+G183*; L205Y+G475K+S243Q+R180*+S181*; L205I+R180*+S181*; L205I+R180*+T182*; L205I+R180*+G183*; L205I+S181*+T182*; L205I+T182*+G183*; L205I+N194F+R180*+S181*; L205I+N194F+R180*+T182*; L205I+N194F+R180*+G183*; L205I+N194F+S181*+T182*; L205I+N194F+T182*+G183*; L205I+N194Y+R180*+S181*; L205I+N194Y+R180*+T182*; L205I+N194Y+R180*+G183*; L205I+N194Y+

S181*+T182*; L205I+N194Y+T182*+G183*; L205I+
G475K+S243Q+R180*+S181*; M208F+R180*+S181*;
M208F+R180*+T182*; M208F+R180*+G183*; M208F+
S181*+T182*; M208F+T182*+G183*; M208F+N194F+
R180*+S181*; M208F+N194F+R180*+T182*; M208F+
N194F+R180*+G183*; M208F+N194F+S181*+T182*;
M208F+N194F+T182*+G183*; M208F+N194Y+R180*+
S181*; M208F+N194Y+R180*+T182*; M208F+N194Y+
R180*+G183*; M208F+N194Y+S181*+T182*; M208F+
N194Y+T182*+G183*; M208F+G475K+S243Q+R180*+
S181*; M208I+R180*+S181*; M208I+R180*+T182*;
M208I+R180*+G183*; M208I+S181*+T182*; M208I+
T182*+G183*; M208I+N194F+R180*+S181*; M208I+
N194F+R180*+T182*; M208I+N194F+R180*+G183*;
M208I+N194F+S181*+T182*; M208I+N194F+T182*+
G183*; M208I+N194Y+R180*+S181*; M208I+N194Y+
R180*+T182*; M208I+N194Y+R180*+G183*; M208I+
N194Y+S181*+T182*; M208I+N194Y+T182*+G183*;
M208I+G475K+S243Q+R180*+S181*; M208L+R180*+
S181*; M208L+R180*+T182*; M208L+R180*+G183*;
M208L+S181*+T182*; M208L+T182*+G183*; M208L+
N194F+R180*+S181*; M208L+N194F+R180*+T182*;
M208L+N194F+R180*+G183*; M208L+N194F+S181*+
T182*; M208L+N194F+T182*+G183*; M208L+N194Y+
R180*+S181*; M208L+N194Y+R180*+T182*; M208L+
N194Y+R180*+G183*; M208L+N194Y+S181*+T182*;
M208L+N194Y+T182*+G183*; M208L+G475K+S243Q+
R180*+S181*; M208Y+R180*+S181*; M208Y+R180*+
T182*; M208Y+R180*+G183*; M208Y+S181*+T182*;
M208Y+T182*+G183*; M208Y+N194F+R180*+S181*;
M208Y+N194F+R180*+T182*; M208Y+N194F+R180*+
G183*; M208Y+N194F+S181*+T182*; M208Y+N194F+
T182*+G183*; M208Y+N194Y+R180*+S181*; M208Y+
N194Y+R180*+T182*; M208Y+N194Y+R180*+G183*;
M208Y+N194Y+S181*+T182*; M208Y+N194Y+T182*+
G183*; M208Y+G475K+S243Q+R180*+S181*; H209D+
R180*+S181*; H209D+R180*+T182*; H209D+R180*+
G183*; H209D+S181*+T182*; H209D+T182*+G183*;
H209D+N194F+R180*+S181*; H209D+N194F+R180*+
T182*; H209D+N194F+R180*+G183*; H209D+N194F+
S181*+T182*; H209D+N194F+T182*+G183*; H209D+
N194Y+R180*+S181*; H209D+N194Y+R180*+T182*;
H209D+N194Y+R180*+G183*; H209D+N194Y+S181*+
T182*; H209D+N194Y+T182*+G183*; H209D+G475K+
S243Q+R180*+S181*; H209M+R180*+S181*; H209M+
R180*+T182*; H209M+R180*+G183*; H209M+S181*+
T182*; H209M+T182*+G183*; H209M+N194F+R180*+
S181*; H209M+N194F+R180*+T182*; H209M+N194F+
R180*+G183*; H209M+N194F+S181*+T182*; H209M+
N194F+T182*+G183*; H209M+N194Y+R180*+S181*;
H209M+N194Y+R180*+T182*; H209M+N194Y+R180*+
G183*; H209M+N194Y+S181*+T182*; H209M+N194Y+
T182*+G183*; H209M+G475K+S243Q+R180*+S181*;
H209T+R180*+S181*; H209T+R180*+T182*; H209T+
R180*+G183*; H209T+S181*+T182*; H209T+T182*+
G183*; H209T+N194F+R180*+S181*; H209T+N194F+
R180*+T182*; H209T+N194F+R180*+G183*; H209T+
N194F+S181*+T182*; H209T+N194F+T182*+G183*;
H209T+N194Y+R180*+S181*; H209T+N194Y+R180*+
T182*; H209T+N194Y+R180*+G183*; H209T+N194Y+
S181*+T182*; H209T+N194Y+T182*+G183*; H209T+
G475K+S243Q+R180*+S181*; E211D+R180*+S181*;
E211D+R180*+T182*; E211D+R180*+G183*; E211D+
S181*+T182*; E211D+T182*+G183*; E211D+N194F+
R180*+S181*; E211D+N194F+R180*+T182*; E211D+
N194F+R180*+G183*; E211D+N194F+S181*+T182*;
E211D+N194F+T182*+G183*; E211D+N194Y+R180*+
S181*; E211D+N194Y+R180*+T182*; E211D+N194Y+
R180*+G183*; E211D+N194Y+S181*+T182*; E211D+
N194Y+T182*+G183*; E211D+G475K+S243Q+R180*+
S181*; E211L+R180*+S181*; E211L+R180*+T182*;
E211L+R180*+G183*; E211L+S181*+T182*; E211L+
T182*+G183*; E211L+N194F+R180*+S181*; E211L+
N194F+R180*+T182*; E211L+N194F+R180*+G183*;
E211L+N194F+S181*+T182*; E211L+N194F+T182*+
G183*; E211L+N194Y+R180*+S181*; E211L+N194Y+
R180*+T182*; E211L+N194Y+R180*+G183*; E211L+
N194Y+S181*+T182*; E211L+N194Y+T182*+G183*;
E211L+G475K+S243Q+R180*+S181*; Y48W+R180*+
S181*; Y48W+R180*+T182*; Y48W+R180*+G183*;
Y48W+S181*+T182*; Y48W+T182*+G183*; Y48W+
N194F+R180*+S181*; Y48W+N194F+R180*+T182*;
Y48W+N194F+R180*+G183*; Y48W+N194F+S181*+
T182*; Y48W+N194F+T182*+G183*; Y48W+N194Y+
R180*+S181*; Y48W+N194Y+R180*+T182*; Y48W+
N194Y+R180*+G183*; Y48W+N194Y+S181*+T182*;
Y48W+N194Y+T182*+G183*; Y48W+G475K+S243Q+
R180*+S181*; V212A+R180*+S181*; V212A+R180*+
T182*; V212A+R180*+G183*; V212A+S181*+T182*;
V212A+T182*+G183*; V212A+N194F+R180*+S181*;
V212A+N194F+R180*+T182*; V212A+N194F+R180*+
G183*; V212A+N194F+S181*+T182*; V212A+N194F+
T182*+G183*; V212A+N194Y+R180*+S181*; V212A+
N194Y+R180*+T182*; V212A+N194Y+R180*+G183*;
V212A+N194Y+S181*+T182*; V212A+N194Y+T182*+
G183*; V212A+G475K+S243Q+R180*+S181*; R309Q+
R180*+S181*; R309Q+R180*+T182*; R309Q+R180*+
G183*; R309Q+S181*+T182*; R309Q+T182*+G183*;
R309Q+N194F+R180*+S181*; R309Q+N194F+R180*+
T182*; R309Q+N194F+R180*+G183*; R309Q+N194F+
S181*+T182*; R309Q+N194F+T182*+G183*; R309Q+
N194Y+R180*+S181*; R309Q+N194Y+R180*+T182*;
R309Q+N194Y+R180*+G183*; R309Q+N194Y+S181*+
T182*; R309Q+N194Y+T182*+G183*; R309Q+G475K+
S243Q+R180*+S181*; I390E+R180*+S181*; I390E+
R180*+T182*; I390E+R180*+G183*; I390E+S181*+
T182*; I390E+T182*+G183*; I390E+N194F+R180*+
S181*; I390E+N194F+R180*+T182*; I390E+N194F+
R180*+G183*; I390E+N194F+S181*+T182*; I390E+
N194F+T182*+G183*; I390E+N194Y+R180*+S181*;
I390E+N194Y+R180*+T182*; I390E+N194Y+R180*+
G183*; I390E+N194Y+S181*+T182*; I390E+N194Y+
T182*+G183*; I390E+G475K+S243Q+R180*+S181*;
V212P+R180*+S181*; V212P+R180*+T182*; V212P+
R180*+G183*; V212P+S181*+T182*; V212P+T182*+
G183*; V212P+N194F+R180*+S181*; V212P+N194F+
R180*+T182*; V212P+N194F+R180*+G183*; V212P+
N194F+S181*+T182*; V212P+N194F+T182*+G183*;
V212P+N194Y+R180*+S181*; V212P+N194Y+R180*+
T182*; V212P+N194Y+R180*+G183*; V212P+N194Y+
S181*+T182*; V212P+N194Y+T182*+G183*; V212P+
G475K+S243Q+R180*+S181*; V212N+R180*+S181*;
V212N+R180*+T182*; V212N+R180*+G183*; V212N+
S181*+T182*; V212N+T182*+G183*; V212N+N194F+
R180*+S181*; V212N+N194F+R180*+T182*; V212N+
N194F+R180*+G183*; V212N+N194F+S181*+T182*;
V212N+N194F+T182*+G183*; V212N+N194Y+R180*+
S181*; V212N+N194Y+R180*+T182*; V212N+N194Y+
R180*+G183*; V212N+N194Y+S181*+T182*; V212N+
N194Y+T182*+G183*; V212N+G475K+S243Q+R180*+
S181*; V212I+R180*+S181*; V212I+R180*+T182*;
V212I+R180*+G183*; V212I+S181*+T182*; V212I+
T182*+G183*; V212I+N194F+R180*+S181*; V212I+
N194F+R180*+T182*; V212I+N194F+R180*+G183*;

V212I+N194F+S181*+T182*; V212I+N194F+T182*+G183*; V212I+N194Y+R180*+S181*; V212I+N194Y+R180*+T182*; V212I+N194Y+R180*+G183*; V212I+N194Y+S181*+T182*; V212I+N194Y+T182*+G183*; V212I+G475K+S243Q+R180*+S181*; N174NN+R180*+S181*; N174NN+R180*+T182*; N174NN+R180*+G183*; N174NN+S181*+T182*; N174NN+T182*+G183*; N174NN+N194F+R180*+S181*; N174NN+N194F+R180*+T182*; N174NN+N194F+R180*+G183*; N174NN+N194F+S181*+T182*; N174NN+N194F+T182*+G183*; N174NN+N194Y+R180*+S181*; N174NN+N194Y+R180*+T182*; N174NN+N194Y+R180*+G183*; N174NN+N194Y+S181*+T182*; V213I+N194Y+T182*+G183*; V213I+G475K+S243Q+R180*+S181*; V213S+R180*+S181*; V213S+R180*+T182*; V213S+R180*+G183*; V213S+S181*+T182*; V213S+T182*+G183*; V213S+N194F+R180*+S181*; V213S+N194F+R180*+T182*; V213S+N194F+R180*+G183*; V213S+N194F+S181*+T182*; V213S+N194F+T182*+G183*; V213S+N194Y+R180*+S181*; V213S+N194Y+R180*+T182*; V213S+N194Y+R180*+G183*; V213S+N194Y+S181*+T182*; V213S+N194Y+T182*+G183*; V213S+G475K+S243Q+R180*+S181*; N174NQ+R180*+S181*; N174NQ+R180*+T182*; N174NQ+R180*+G183*; N174NQ+S181*+T182*; N174NQ+T182*+G183*; N174NQ+N194F+R180*+S181*; N174NQ+N194F+R180*+T182*; N174NQ+N194F+R180*+G183*; N174NQ+N194F+S181*+T182*; N174NQ+N194F+T182*+G183*; N174NQ+N194Y+R180*+S181*; N174NQ+N194Y+R180*+T182*; N174NQ+N194Y+R180*+G183*; N174NQ+N194Y+S181*+T182*; N174NQ+N194Y+T182*+G183*; N174NQ+G475K+S243Q+R180*+S181*; V213Q+R180*+S181*; V213Q+R180*+T182*; V213Q+R180*+G183*; V213Q+S181*+T182*; V213Q+T182*+G183*; V213Q+N194F+R180*+S181*; V213Q+N194F+R180*+T182*; V213Q+N194F+R180*+G183*; V213Q+N194F+S181*+T182*; V213Q+N194F+T182*+G183*; V213Q+N194Y+R180*+S181*; V213Q+N194Y+R180*+T182*; V213Q+N194Y+R180*+G183*; V213Q+N194Y+S181*+T182*; V213Q+N194Y+T182*+G183*; V213Q+G475K+S243Q+R180*+S181*; K241R+R180*+S181*; K241R+R180*+T182*; K241R+R180*+G183*; K241R+S181*+T182*; K241R+T182*+G183*; K241R+N194F+R180*+S181*; K241R+N194F+R180*+T182*; K241R+N194F+R180*+G183*; K241R+N194F+S181*+T182*; K241R+N194F+T182*+G183*; K241R+N194Y+R180*+S181*; K241R+N194Y+R180*+T182*; K241R+N194Y+R180*+G183*; K241R+N194Y+S181*+T182*; K241R+N194Y+T182*+G183*; K241R+G475K+S243Q+R180*+S181*; Y242F+R180*+S181*; Y242F+R180*+T182*; Y242F+R180*+G183*; Y242F+S181*+T182*; Y242F+T182*+G183*; Y242F+N194F+R180*+S181*; Y242F+N194F+R180*+T182*; Y242F+N194F+R180*+G183*; Y242F+N194F+S181*+T182*; Y242F+N194F+T182*+G183*; Y242F+N194Y+R180*+S181*; Y242F+N194Y+R180*+T182*; Y242F+N194Y+R180*+G183*; Y242F+N194Y+S181*+T182*; Y242F+N194Y+T182*+G183*; Y242F+G475K+S243Q+R180*+S181*; F245I+R180*+S181*; F245I+R180*+T182*; F245I+R180*+G183*; F245I+S181*+T182*; F245I+T182*+G183*; F245I+N194F+R180*+S181*; F245I+N194F+R180*+T182*; F245I+N194F+R180*+G183*; F245I+N194F+S181*+T182*; F245I+N194F+T182*+G183*; F245I+N194Y+R180*+S181*; F245I+N194Y+R180*+T182*; F245I+N194Y+R180*+G183*; F245I+N194Y+S181*+T182*; F245I+N194Y+T182*+G183*; F245I+G475K+S243Q+R180*+S181*; F245L+R180*+S181*; F245L+R180*+T182*; F245L+R180*+G183*; F245L+S181*+T182*; F245L+T182*+G183*; F245L+N194F+R180*+S181*; F245L+N194F+R180*+T182*; F245L+N194F+R180*+G183*; F245L+N194F+S181*+T182*; F245L+N194F+T182*+G183*; F245L+N194Y+R180*+S181*; F245L+N194Y+R180*+T182*; F245L+N194Y+R180*+G183*; F245L+N194Y+S181*+T182*; F245L+N194Y+T182*+G183*; F245L+G475K+S243Q+R180*+S181*; F245M+R180*+S181*; F245M+R180*+T182*; F245M+R180*+G183*; F245M+S181*+T182*; F245M+T182*+G183*; F245M+N194F+R180*+S181*; F245M+N194F+R180*+T182*; F245M+N194F+R180*+G183*; F245M+N194F+S181*+T182*; F245M+N194F+T182*+G183*; F245M+N194Y+R180*+S181*; F245M+N194Y+R180*+T182*; F245M+N194Y+R180*+G183*; F245M+N194Y+S181*+T182*; F245M+N194Y+T182*+G183*; F245M+G475K+S243Q+R180*+S181*; F245S+R180*+S181*; F245S+R180*+T182*; F245S+R180*+G183*; F245S+S181*+T182*; F245S+T182*+G183*; F245S+N194F+R180*+S181*; F245S+N194F+R180*+T182*; F245S+N194F+R180*+G183*; F245S+N194F+S181*+T182*; F245S+N194F+T182*+G183*; F245S+N194Y+R180*+S181*; F245S+N194Y+R180*+T182*; F245S+N194Y+R180*+G183*; F245S+N194Y+S181*+T182*; F245S+N194Y+T182*+G183*; F245S+G475K+S243Q+R180*+S181*; F245T+R180*+S181*; F245T+R180*+T182*; F245T+R180*+G183*; F245T+S181*+T182*; F245T+T182*+G183*; F245T+N194F+R180*+S181*; F245T+N194F+R180*+T182*; F245T+N194F+R180*+G183*; F245T+N194F+S181*+T182*; F245T+N194F+T182*+G183*; F245T+N194Y+R180*+S181*; F245T+N194Y+R180*+T182*; F245T+N194Y+R180*+G183*; F245T+N194Y+S181*+T182*; F245T+N194Y+T182*+G183*; F245T+G475K+S243Q+R180*+S181*; F245V+R180*+S181*; F245V+R180*+T182*; F245V+R180*+G183*; F245V+S181*+T182*; F245V+T182*+G183*; F245V+N194F+R180*+S181*; F245V+N194F+R180*+T182*; F245V+N194F+R180*+G183*; F245V+N194F+S181*+T182*; F245V+N194F+T182*+G183*; F245V+N194Y+R180*+S181*; F245V+N194Y+R180*+T182*; F245V+N194Y+R180*+G183*; F245V+N194Y+S181*+T182*; F245V+N194Y+T182*+G183*; F245V+G475K+S243Q+R180*+S181*; F245Y+R180*+S181*; F245Y+R180*+T182*; F245Y+R180*+G183*; F245Y+S181*+T182*; F245Y+T182*+G183*; F245Y+N194F+R180*+S181*; F245Y+N194F+R180*+T182*; F245Y+N194F+R180*+G183*; F245Y+N194F+S181*+T182*; F245Y+N194F+T182*+G183*; F245Y+N194Y+R180*+S181*; F245Y+N194Y+R180*+T182*; F245Y+N194Y+R180*+G183*; F245Y+N194Y+S181*+T182*; F245Y+N194Y+T182*+G183*; F245Y+G475K+S243Q+R180*+S181*; F266Y+R180*+S181*; F266Y+R180*+T182*; F266Y+R180*+G183*; F266Y+S181*+T182*; F266Y+T182*+G183*; F266Y+N194F+R180*+S181*; F266Y+N194F+R180*+T182*; F266Y+N194F+R180*+G183*; F266Y+N194F+S181*+T182*; F266Y+N194F+T182*+G183*; F266Y+N194Y+R180*+S181*; F266Y+N194Y+R180*+T182*; F266Y+N194Y+R180*+G183*; F266Y+N194Y+S181*+T182*; F266Y+N194Y+T182*+G183*; F266Y+G475K+S243Q+R180*+S181*; Y269N+R180*+S181*; Y269N+R180*+T182*; Y269N+R180*+G183*; Y269N+S181*+T182*; Y269N+T182*+G183*; Y269N+N194F+R180*+S181*; Y269N+N194F+R180*+T182*; Y269N+N194F+R180*+G183*; Y269N+N194F+S181*+T182*; Y269N+N194F+T182*+G183*; Y269N+N194Y+R180*+S181*; Y269N+N194Y+R180*+T182*; Y269N+N194Y+R180*+G183*; Y269N+N194Y+S181*+T182*;

Y269N+N194Y+T182*+G183*; Y269N+G475K+S243Q+ R180*+S181*; K280R+R180*+S181*; K280R+R180*+ T182*; K280R+R180*+G183*; K280R+S181*+T182*; K280R+T182*+G183*; K280R+N194F+R180*+S181*; K280R+N194F+R180*+T182*; K280R+N194F+R180*+ G183*; K280R+N194F+S181*+T182*; K280R+N194F+ T182*+G183*; K280R+N194Y+R180*+S181*; K280R+ N194Y+R180*+T182*; K280R+N194Y+R180*+G183*; K280R+N194Y+S181*+T182*; K280R+N194Y+T182*+ G183*; K280R+G475K+S243Q+R180*+S181*; G283S+ R180*+S181*; G283S+R180*+T182*; G283S+R180*+ G183*; G283S+S181*+T182*; G283S+T182*+G183*; G283S+N194F+R180*+S181*; G283S+N194F+R180*+ T182*; G283S+N194F+R180*+G183*; G283S+N194F+ S181*+T182*; G283S+N194F+T182*+G183*; G283S+ N194Y+R180*+S181*; G283S+N194Y+R180*+T182*; G283S+N194Y+R180*+G183*; G283S+N194Y+S181*+ T182*; G283S+N194Y+T182*+G183*; G283S+G475K+ S243Q+R180*+S181*; M285F+R180*+S181*; M285F+ R180*+T182*; M285F+R180*+G183*; M285F+S181*+ T182*; M285F+T182*+G183*; M285F+N194F+R180*+ S181*; M285F+N194F+R180*+T182*; M285F+N194F+ R180*+G183*; M285F+N194F+S181*+T182*; M285F+ N194F+T182*+G183*; M285F+N194Y+R180*+S181*; M285F+N194Y+R180*+T182*; M285F+N194Y+R180*+ G183*; M285F+N194Y+S181*+T182*; M285F+N194Y+ T182*+G183*; M285F+G475K+S243Q+R180*+S181*; M285H+R180*+S181*; M285H+R180*+T182*; M285H+ R180*+G183*; M285H+S181*+T182*; M285H+T182*+ G183*; M285H+N194F+R180*+S181*; M285H+N194F+ R180*+T182*; M285H+N194F+R180*+G183*; M285H+ N194F+S181*+T182*; M285H+N194F+T182*+G183*; M285H+N194Y+R180*+S181*; M285H+N194Y+R180*+ T182*; M285H+N194Y+R180*+G183*; M285H+N194Y+ S181*+T182*; M285H+N194Y+T182*+G183*; M285H+ G475K+S243Q+R180*+S181*; N294Y+R180*+S181*; N294Y+R180*+T182*; N294Y+R180*+G183*; N294Y+ S181*+T182*; N294Y+T182*+G183*; N294Y+N194F+ R180*+S181*; N294Y+N194F+R180*+T182*; N294Y+ N194F+R180*+G183*; N294Y+N194F+S181*+T182*; N294Y+N194F+T182*+G183*; N294Y+N194Y+R180*+ S181*; N294Y+N194Y+R180*+T182*; N294Y+N194Y+ R180*+G183*; N294Y+N194Y+S181*+T182*; N294Y+ N194Y+T182*+G183*; N294Y+G475K+S243Q+R180*+ S181*; M317F+R180*+S181*; M317F+R180*+T182*; M317F+R180*+G183*; M317F+S181*+T182*; M317F+ T182*+G183*; M317F+N194F+R180*+S181*; M317F+ N194F+R180*+T182*; M317F+N194F+R180*+G183*; M317F+N194F+S181*+T182*; M317F+N194F+T182*+ G183*; M317F+N194Y+R180*+S181*; M317F+N194Y+ R180*+T182*; M317F+N194Y+R180*+G183*; M317F+ N194Y+S181*+T182*; M317F+N194Y+T182*+G183*; M317F+G475K+S243Q+R180*+S181*; M317I+R180*+ S181*; M317I+R180*+T182*; M317I+R180*+G183*; M317I+S181*+T182*; M317I+T182*+G183*; M317I+ N194F+R180*+S181*; M317I+N194F+R180*+T182*; M317I+N194F+R180*+G183*; M317I+N194F+S181*+ T182*; M317I+N194F+T182*+G183*; M317I+N194Y+ R180*+S181*; M317I+N194Y+R180*+T182*; M317I+ N194Y+R180*+G183*; M317I+N194Y+S181*+T182*; M317I+N194Y+T182*+G183*; M317I+G475K+S243Q+ R180*+S181*; M317L+R180*+S181*; M317L+R180*+ T182*; M317L+R180*+G183*; M317L+S181*+T182*; M317L+T182*+G183*; M317L+N194F+R180*+S181*; M317L+N194F+R180*+T182*; M317L+N194F+R180*+ G183*; M317L+N194F+S181*+T182*; M317L+N194F+ T182*+G183*; M317L+N194Y+R180*+S181*; M317L+ N194Y+R180*+T182*; M317L+N194Y+R180*+G183*; M317L+N194Y+S181*+T182*; M317L+N194Y+T182*+ G183*; M317L+G475K+S243Q+R180*+S181*; M317V+ R180*+S181*; M317V+R180*+T182*; M317V+R180*+ G183*; M317V+S181*+T182*; M317V+T182*+G183*; M317V+N194F+R180*+S181*; M317V+N194F+R180*+ T182*; M317V+N194F+R180*+G183*; M317V+N194F+ S181*+T182*; M317V+N194F+T182*+G183*; M317V+ N194Y+R180*+S181*; M317V+N194Y+R180*+T182*; M317V+N194Y+R180*+G183*; M317V+N194Y+S181*+ T182*; M317V+N194Y+T182*+G183*; M317V+G475K+ S243Q+R180*+S181*; M317Y+R180*+S181*; M317Y+ R180*+T182*; M317Y+R180*+G183*; M317Y+S181*+ T182*; M317Y+T182*+G183*; M317Y+N194F+R180*+ S181*; M317Y+N194F+R180*+T182*; M317Y+N194F+ R180*+G183*; M317Y+N194F+S181*+T182*; M317Y+ N194F+T182*+G183*; M317Y+N194Y+R180*+S181*; M317Y+N194Y+R180*+T182*; M317Y+N194Y+R180*+ G183*; M317Y+N194Y+S181*+T182*; M317Y+N194Y+ T182*+G183*; M317Y+G475K+S243Q+R180*+S181*; L323H+R180*+S181*; L323H+R180*+T182*; L323H+ R180*+G183*; L323H+S181*+T182*; L323H+T182*+ G183*; L323H+N194F+R180*+S181*; L323H+N194F+ R180*+T182*; L323H+N194F+R180*+G183*; L323H+ N194F+S181*+T182*; L323H+N194F+T182*+G183*; L323H+N194Y+R180*+S181*; L323H+N194Y+R180*+ T182*; L323H+N194Y+R180*+G183*; L323H+N194Y+ S181*+T182*; L323H+N194Y+T182*+G183*; L323H+ G475K+S243Q+R180*+S181*; K375Q+R180*+S181*; K375Q+R180*+T182*; K375Q+R180*+G183*; K375Q+ S181*+T182*; K375Q+T182*+G183*; K375Q+N194F+ R180*+S181*; K375Q+N194F+R180*+T182*; K375Q+ N194F+R180*+G183*; K375Q+N194F+S181*+T182*; K375Q+N194F+T182*+G183*; K375Q+N194Y+R180*+ S181*; K375Q+N194Y+R180*+T182*; K375Q+N194Y+ R180*+G183*; K375Q+N194Y+S181*+T182*; K375Q+ N194Y+T182*+G183*; K375Q+G475K+S243Q+R180*+ S181*; I390E+R180*+S181*; I390E+R180*+T182*; I390E+R180*+G183*; I390E+S181*+T182*; I390E+ T182*+G183*; I390E+N194F+R180*+S181*; I390E+ N194F+R180*+T182*; I390E+N194F+R180*+G183*; I390E+N194F+S181*+T182*; I390E+N194F+T182*+ G183*; I390E+N194Y+R180*+S181*; I390E+N194Y+ R180*+T182*; I390E+N194Y+R180*+G183*; I390E+ N194Y+S181*+T182*; I390E+N194Y+T182*+G183*; I390E+G475K+S243Q+R180*+S181*; I390D+R180*+ S181*; I390D+R180*+T182*; I390D+R180*+G183*; I390D+S181*+T182*; I390D+T182*+G183*; I390D+ N194F+R180*+S181*; I390D+N194F+R180*+T182*; I390D+N194F+R180*+G183*; I390D+N194F+S181*+ T182*; I390D+N194F+T182*+G183*; I390D+N194Y+ R180*+S181*; I390D+N194Y+R180*+T182*; I390D+ N194Y+R180*+G183*; I390D+N194Y+S181*+T182*; I390D+N194Y+T182*+G183*; I390D+G475K+S243Q+R180*+S181*; I390Q+R180*+S181*; I390Q+R180*+T182*; I390Q+R180*+G183*; I390Q+S181*+T182*; I390Q+T182*+G183*; I390Q+N194F+R180*+S181*; I390Q+N194F+R180*+T182*; I390Q+N194F+R180*+G183*; I390Q+N194F+S181*+T182*; I390Q+N194F+T182*+G183*; I390Q+N194Y+R180*+S181*; I390Q+N194Y+R180*+T182*; I390Q+N194Y+R180*+G183*; I390Q+N194Y+S181*+T182*; I390Q+N194Y+T182*+G183*; I390Q+G475K+S243Q+R180*+S181*; I390N+R180*+S181*; I390N+R180*+T182*; I390N+R180*+G183*; I390N+S181*+T182*; I390N+T182*+G183*; I390N+N194F+R180*+S181*; I390N+N194F+R180*+T182*; I390N+N194F+R180*+G183*; I390N+N194F+

S181*+T182*; I390N+N194F+T182*+G183*; I390N+N194Y+R180*+S181*; I390N+N194F+R180*+T182*; I390N+N194Y+R180*+G183*; I390N+N194Y+S181*+T182*; I390N+N194Y+T182*+G183*; I390N+G475K+S243Q+R180*+S181*; I404F+R180*+S181*; I404F+R180*+T182*; I404F+R180*+G183*; I404F+S181*+T182*; I404F+T182*+G183*; I404F+N194F+R180*+S181*; I404F+N194F+R180*+T182*; I404F+N194F+R180*+G183*; I404F+N194F+S181*+T182*; I404F+N194F+T182*+G183*; I404F+N194Y+R180*+S181*; I404F+N194Y+R180*+T182*; I404F+N194Y+R180*+G183*; I404F+N194Y+S181*+T182*; I404F+N194Y+T182*+G183*; I404F+G475K+S243Q+R180*+S181*; I404L+R180*+S181*; I404L+R180*+T182*; I404L+R180*+G183*; I404L+S181*+T182*; I404L+T182*+G183*; I404L+N194F+R180*+S181*; I404L+N194F+R180*+T182*; I404L+N194F+R180*+G183*; I404L+N194F+S181*+T182*; I404L+N194F+T182*+G183*; I404L+N194Y+R180*+S181*; I404L+N194Y+R180*+T182*; I404L+N194Y+R180*+G183*; I404L+N194Y+S181*+T182*; I404L+N194Y+T182*+G183*; I404L+G475K+S243Q+R180*+S181*; I404Y+R180*+S181*; I404Y+R180*+T182*; I404Y+R180*+G183*; I404Y+S181*+T182*; I404Y+T182*+G183*; I404Y+N194F+R180*+S181*; I404Y+N194F+R180*+T182*; I404Y+N194F+R180*+G183*; I404Y+N194F+S181*+T182*; I404Y+N194F+T182*+G183*; I404Y+N194Y+R180*+S181*; I404Y+N194Y+R180*+T182*; I404Y+N194Y+R180*+G183*; I404Y+N194Y+S181*+T182*; I404Y+N194Y+T182*+G183*; I404Y+G475K+S243Q+R180*+S181*; Q407H+R180*+S181*; Q407H+R180*+T182*; Q407H+R180*+G183*; Q407H+S181*+T182*; Q407H+T182*+G183*; Q407H+N194F+R180*+S181*; Q407H+N194F+R180*+T182*; Q407H+N194F+R180*+G183*; Q407H+N194F+S181*+T182*; Q407H+N194F+T182*+G183*; Q407H+N194Y+R180*+S181*; Q407H+N194Y+R180*+T182*; Q407H+N194Y+R180*+G183*; Q407H+N194Y+S181*+T182*; Q407H+N194Y+T182*+G183*; Q407H+G475K+S243Q+R180*+S181*; N194F+L205Y+R180*+S181*; N194F+L205Y+R180*+T182*; N194F+L205Y+R180*+G183*; N194F+L205Y+S181*+T182*; N194F+L205Y+T182*+G183*; N194F+L205Y+G475K+S243Q+R180*+S181*; N194F+L205F+R180*+S181*; N194F+L205F+R180*+T182*; N194F+L205F+R180*+G183*; N194F+L205F+S181*+T182*; N194F+L205F+T182*+G183*; N194F+L205F+G475K+S243Q+R180*+S181*; N194Y+L205Y+R180*+S181*; N194Y+L205Y+R180*+T182*; N194Y+L205Y+R180*+G183*; N194Y+L205Y+S181*+T182*; N194Y+L205Y+T182*+G183*; N194Y+L205Y+G475K+S243Q+R180*+S181*; N194Y+L205F+R180*+S181*; N194Y+L205F+R180*+T182*; N194Y+L205F+R180*+G183*; N194Y+L205F+S181*+T182*; N194Y+L205F+T182*+G183*; N194Y+L205F+G475K+S243Q+R180*+S181*; R309Q+N174NQ+R180*+S181*; R309Q+N174NQ+R180*+T182*; R309Q+N174NQ+R180*+G183*; R309Q+N174NQ+S181*+T182*; R309Q+N174NQ+T182*+G183*; R309Q+N174NQ+N194F+R180*+S181*; R309Q+N174NQ+N194F+R180*+T182*; R309Q+N174NQ+N194F+R180*+G183*; R309Q+N174NQ+N194F+S181*+T182*; R309Q+N174NQ+N194F+T182*+G183*; R309Q+N174NQ+N194Y+R180*+S181*; R309Q+N174NQ+N194Y+R180*+T182*; R309Q+N174NQ+N194Y+R180*+G183*; R309Q+N174NQ+N194Y+S181*+T182*; R309Q+N174NQ+N194Y+T182*+G183*; R309Q+N174NQ+G475K+S243Q+R180*+S181*; Y48W+N174NQ+R180*+S181*; Y48W+N174NQ+R180*+T182*; Y48W+N174NQ+R180*+G183*; Y48W+N174NQ+S181*+T182*; Y48W+N174NQ+T182*+G183*; Y48W+N174NQ+N194F+R180*+S181*; Y48W+N174NQ+N194F+R180*+T182*; Y48W+N174NQ+N194F+R180*+G183*; Y48W+N174NQ+N194F+S181*+T182*; Y48W+N174NQ+N194F+T182*+G183*; Y48W+N174NQ+N194Y+R180*+S181*; Y48W+N174NQ+N194Y+R180*+T182*; Y48W+N174NQ+N194Y+R180*+G183*; Y48W+N174NQ+N194Y+S181*+T182*; Y48W+N174NQ+N194Y+T182*+G183*; Y48W+N174NQ+G475K+S243Q+R180*+S181*; V212N+V213I+R180*+S181*; V212N+V213I+R180*+T182*; V212N+V213I+R180*+G183*; V212N+V213 I+S181*+T182*; V212N+V213I+T182*+G183*; V212N+V213I+N194F+R180*+S181*; V212N+V213I+N194F+R180*+T182*; V212N+V213I+N194F+R180*+G183*; V212N+V213I+N194F+S181*+T182*; V212N+V213I+N194F+T182*+G183*; V212N+V213I+N194Y+R180*+S181*; V212N+V213I+N194Y+R180*+T182*; V212N+V213I+N194Y+R180*+G183*; V212N+V213I+N194Y+S181*+T182*; V212N+V213I+N194Y+T182*+G183*; V212N+V213I+G475K+S243Q+R180*+S181*; V212N+V213Q+R180*+S181*; V212N+V213Q+R180*+T182*; V212N+V213Q+R180*+G183*; V212N+V213Q+S181*+T182*; V212N+V213Q+T182*+G183*; V212N+V213Q+N194F+R180*+S181*; V212N+V213Q+N194F+R180*+T182*; V212N+V213Q+N194F+R180*+G183*; V212N+V213Q+N194F+S181*+T182*; V212N+V213Q+N194F+T182*+G183*; V212N+V213Q+N194Y+R180*+S181*; V212N+V213Q+N194Y+R180*+T182*; V212N+V213Q+N194Y+R180*+G183*; V212N+V213Q+N194Y+S181*+T182*; V212N+V213Q+N194Y+T182*+G183*; V212N+V213Q+G475K+S243Q+R180*+S181*; V212P+N174NQ+R180*+S181*; V212P+N174NQ+R180*+T182*; V212P+N174NQ+R180*+G183*; V212P+N174NQ+S181*+T182*; V212P+N174NQ+T182*+G183*; V212P+N174NQ+N194F+R180*+S181*; V212P+N174NQ+N194F+R180*+T182*; V212P+N174NQ+N194F+R180*+G183*; V212P+N174NQ+N194F+S181*+T182*; V212P+N174NQ+N194F+T182*+G183*; V212P+N174NQ+N194Y+R180*+S181*; V212P+N174NQ+N194Y+R180*+T182*; V212P+N174NQ+N194Y+R180*+G183*; V212P+N174NQ+N194Y+S181*+T182*; V212P+N174NQ+N194Y+T182*+G183*; V212P+N174NQ+G475K+S243Q+R180*+S181*; D16Y+K375Q+R180*+S181*; D16Y+K375Q+R180*+T182*; D16Y+K375Q+R180*+G183*; D16Y+K375Q+S181*+T182*; D16Y+K375Q+T182*+G183*; D16Y+K375Q+N194F+R180*+S181*; D16Y+K375Q+N194F+R180*+T182*; D16Y+K375Q+N194F+R180*+G183*; D16Y+K375Q+N194F+S181*+T182*; D16Y+K375Q+N194F+T182*+G183*; D16Y+K375Q+N194Y+R180*+S181*; D16Y+K375Q+N194Y+R180*+T182*; D16Y+K375Q+N194Y+R180*+G183*; D16Y+K375Q+N194Y+S181*+T182*; D16Y+K375Q+N194Y+T182*+G183*; D16Y+K375Q+G475K+S243Q+R180*+S181*; N19D+Q53R+R180*+S181*; N19D+Q53R+R180*+T182*; N19D+Q53R+R180*+G183*; N19D+Q53R+S181*+T182*; N19D+Q53R+T182*+G183*; N19D+Q53R+N194F+R180*+S181*; N19D+Q53R+N194F+R180*+T182*; N19D+Q53R+N194F+R180*+G183*; N19D+Q53R+N194F+S181*+T182*; N19D+Q53R+N194F+T182*+G183*; N19D+Q53R+N194Y+R180*+S181*; N19D+Q53R+N194Y+R180*+T182*; N19D+Q53R+N194Y+R180*+G183*; N19D+Q53R+N194Y+S181*+T182*; N19D+Q53R+N194Y+T182*+G183*; N19D+Q53R+G475K+S243Q+R180*+S181*; Y48W+V60A+R180*+S181*; Y48W+V60A+R180*+T182*; Y48W+

V60A+R180*+G183*; Y48W+V60A+S181*+T182*; Y48W+V60A+T182*+G183*; Y48W+V60A+N194F+R180*+S181*; Y48W+V60A+N194F+R180*+T182*; Y48W+V60A+N194F+R180*+G183*; Y48W+V60A+N194F+S181*+T182*; Y48W+V60A+N194F+T182*+G183*; Y48W+V60A+N194Y+R180*+S181*; Y48W+V60A+N194Y+R180*+T182*; Y48W+V60A+N194Y+R180*+G183*; Y48W+V60A+N194Y+S181*+T182*; Y48W+V60A+N194Y+T182*+G183*; Y48W+V60A+G475K+S243Q+R180*+S181*; Y48W+F105M+R180*+S181*; Y48W+F105M+R180*+T182*; Y48W+F105M+R180*+G183*; Y48W+F105M+S181*+T182*; Y48W+F105M+T182*+G183*; Y48W+F105M+N194F+R180*+S181*; Y48W+F105M+N194F+R180*+T182*; Y48W+F105M+N194F+R180*+G183*; Y48W+F105M+N194F+S181*+T182*; Y48W+F105M+N194F+T182*+G183*; Y48W+F105M+N194Y+R180*+S181*; Y48W+F105M+N194Y+R180*+T182*; Y48W+F105M+N194Y+R180*+G183*; Y48W+F105M+N194Y+S181*+T182*; Y48W+F105M+N194Y+T182*+G183*; Y48W+F105M+G475K+S243Q+R180*+S181*; Y48W+L205Y+R180*+S181*; Y48W+L205Y+R180*+T182*; Y48W+L205Y+R180*+G183*; Y48W+L205Y+S181*+T182*; Y48W+L205Y+T182*+G183*; Y48W+L205Y+N194F+R180*+S181*; Y48W+L205Y+N194F+R180*+T182*; Y48W+L205Y+N194F+R180*+G183*; Y48W+L205Y+N194F+S181*+T182*; Y48W+L205Y+N194F+T182*+G183*; Y48W+L205Y+N194Y+R180*+S181*; Y48W+L205Y+N194Y+R180*+T182*; Y48W+L205Y+N194Y+R180*+G183*; Y48W+L205Y+N194Y+S181*+T182*; Y48W+L205Y+N194Y+T182*+G183*; Y48W+L205Y+G475K+S243Q+R180*+S181*; V60A+L205Y+R180*+S181*; V60A+L205Y+R180*+T182*; V60A+L205Y+R180*+G183*; V60A+L205Y+S181*+T182*; V60A+L205Y+T182*+G183*; V60A+L205Y+N194F+R180*+S181*; V60A+L205Y+N194F+R180*+T182*; V60A+L205Y+N194F+R180*+G183*; V60A+L205Y+N194F+S181*+T182*; V60A+L205Y+N194F+T182*+G183*; V60A+L205Y+N194Y+R180*+S181*; V60A+L205Y+N194Y+R180*+T182*; V60A+L205Y+N194Y+R180*+G183*; V60A+L205Y+N194Y+S181*+T182*; V60A+L205Y+N194Y+T182*+G183*; V60A+L205Y+G475K+S243Q+R180*+S181*; Y48W+V60A+F105M+R180*+S181*; Y48W+V60A+F105M+R180*+T182*; Y48W+V60A+F105M+R180*+G183*; Y48W+V60A+F105M+S181*+T182*; Y48W+V60A+F105M+T182*+G183*; Y48W+V60A+F105M+N194F+R180*+S181*; Y48W+V60A+F105M+N194F+R180*+T182*; Y48W+V60A+F105M+N194F+R180*+G183*; Y48W+V60A+F105M+N194F+S181*+T182*; Y48W+V60A+F105M+N194F+T182*+G183*; Y48W+V60A+F105M+N194Y+R180*+S181*; Y48W+V60A+F105M+N194Y+R180*+T182*; Y48W+V60A+F105M+N194Y+R180*+G183*; Y48W+V60A+F105M+N194Y+S181*+T182*; Y48W+V60A+F105M+N194Y+T182*+G183*; Y48W+V60A+F105M+G475K+S243Q+R180*+S181*; Y48W+V60A+L205F+R180*+S181*; Y48W+V60A+L205F+R180*+T182*; Y48W+V60A+L205F+R180*+G183*; Y48W+V60A+L205F+S181*+T182*; Y48W+V60A+L205F+T182*+G183*; Y48W+V60A+L205F+N194F+R180*+S181*; Y48W+V60A+L205F+N194F+R180*+T182*; Y48W+V60A+L205F+N194F+R180*+G183*; Y48W+V60A+L205F+N194F+S181*+T182*; Y48W+V60A+L205F+N194F+T182*+G183*; Y48W+V60A+L205F+N194Y+R180*+S181*; Y48W+V60A+L205F+N194Y+R180*+T182*; Y48W+V60A+L205F+N194Y+R180*+G183*; Y48W+V60A+L205F+N194Y+S181*+T182*; Y48W+V60A+L205F+N194Y+T182*+G183*; Y48W+V60A+L205F+G475K+S243Q+R180*+S181*; V60A+F105M+L205F+R180*+S181*; V60A+F105M+L205F+R180*+T182*; V60A+F105M+L205F+R180*+G183*; V60A+F105M+L205F+S181*+T182*; V60A+F105M+L205F+T182*+G183*; V60A+F105M+L205F+N194F+R180*+S181*; V60A+F105M+L205F+N194F+R180*+T182*; V60A+F105M+L205F+N194F+R180*+G183*; V60A+F105M+L205F+N194F+S181*+T182*; V60A+F105M+L205F+N194F+T182*+G183*; V60A+F105M+L205F+N194Y+R180*+S181*; V60A+F105M+L205F+N194Y+R180*+T182*; V60A+F105M+L205F+N194Y+R180*+G183*; V60A+F105M+L205F+N194Y+S181*+T182*; V60A+F105M+L205F+N194Y+T182*+G183*; V60A+F105M+L205F+G475K+S243Q+R180*+S181*; Y48W+V60A+F105M+L205F+R180*+S181*; Y48W+V60A+F105M+L205F+R180*+T182*; Y48W+V60A+F105M+L205F+R180*+G183*; Y48W+V60A+F105M+L205F+S181*+T182*; Y48W+V60A+F105M+L205F+T182*+G183*; Y48W+V60A+F105M+L205F+N194F+R180*+S181*; Y48W+V60A+F105M+L205F+N194F+R180*+T182*; Y48W+V60A+F105M+L205F+N194F+R180*+G183*; Y48W+V60A+F105M+L205F+N194F+S181*+T182*; Y48W+V60A+F105M+L205F+N194F+T182*+G183*; Y48W+V60A+F105M+L205F+N194Y+R180*+S181*; Y48W+V60A+F105M+L205F+N194Y+R180*+T182*; Y48W+V60A+F105M+L205F+N194Y+R180*+G183*; Y48W+V60A+F105M+L205F+N194Y+S181*+T182*; Y48W+V60A+F105M+L205F+N194Y+T182*+G183*; Y48W+V60A+F105M+L205F+G475K+S243Q+R180*+S181*; Y48W+V60A+L205Y+R180*+S181*; Y48W+V60A+L205Y+R180*+T182*; Y48W+V60A+L205Y+R180*+G183*; Y48W+V60A+L205Y+S181*+T182*; Y48W+V60A+L205Y+T182*+G183*; Y48W+V60A+L205Y+N194F+R180*+S181*; Y48W+V60A+L205Y+N194F+R180*+T182*; Y48W+V60A+L205Y+N194F+R180*+G183*; Y48W+V60A+L205Y+N194F+S181*+T182*; Y48W+V60A+L205Y+N194F+T182*+G183*; Y48W+V60A+L205Y+N194Y+R180*+S181*; Y48W+V60A+L205Y+N194Y+R180*+T182*; Y48W+V60A+L205Y+N194Y+R180*+G183*; Y48W+V60A+L205Y+N194Y+S181*+T182*; Y48W+V60A+L205Y+N194Y+T182*+G183*; Y48W+V60A+L205Y+G475K+S243Q+R180*+S181*; V60A+F105M+L205Y+R180*+S181*; V60A+F105M+L205Y+R180*+T182*; V60A+F105M+L205Y+R180*+G183*; V60A+F105M+L205Y+S181*+T182*; V60A+F105M+L205Y+T182*+G183*; V60A+F105M+L205Y+N194F+R180*+S181*; V60A+F105M+L205Y+N194F+R180*+T182*; V60A+F105M+L205Y+N194F+R180*+G183*; V60A+F105M+L205Y+N194F+S181*+T182*; V60A+F105M+L205Y+N194F+T182*+G183*; V60A+F105M+L205Y+N194Y+R180*+S181*; V60A+F105M+L205Y+N194Y+R180*+T182*; V60A+F105M+L205Y+N194Y+R180*+G183*; V60A+F105M+L205Y+N194Y+S181*+T182*; V60A+F105M+L205Y+N194Y+T182*+G183*; V60A+F105M+L205Y+G475K+S243Q+R180*+S181*; Y48W+V60A+F105M+L205Y+R180*+S181*; Y48W+V60A+F105M+L205Y+R180*+T182*; Y48W+V60A+F105M+L205Y+R180*+G183*; Y48W+V60A+F105M+L205Y+S181*+T182*; Y48W+V60A+F105M+L205Y+T182*+G183*; Y48W+V60A+F105M+L205Y+N194F+R180*+S181*; Y48W+V60A+F105M+L205Y+N194F+R180*+T182*; Y48W+V60A+F105M+L205Y+N194F+R180*+G183*; Y48W+V60A+F105M+L205Y+N194F+S181*+T182*; Y48W+V60A+F105M+L205Y+N194F+T182*+G183*; Y48W+V60A+F105M+

L205Y+N194Y+R180*+T182*; L205Y+N194Y+R180*+G183*; L205Y+N194Y+S181*+T182*; L205Y+N194Y+T182*+G183*; L205Y+G475K+S243Q+R180*+S181*; P124D+S125P+R180*+S181*; P124D+S125P+R180*+T182*; P124D+S125P+R180*+G183*; P124D+S125P+S181*+T182*; P124D+S125P+T182*+G183*; P124D+S125P+N194F+R180*+S181*; P124D+S125P+N194F+R180*+T182*; P124D+S125P+N194F+R180*+G183*; P124D+S125P+N194F+S181*+T182*; P124D+S125P+N194F+T182*+G183*; P124D+S125P+N194Y+R180*+S181*; P124D+S125P+N194Y+R180*+T182*; P124D+S125P+N194Y+R180*+G183*; P124D+S125P+N194Y+S181*+T182*; P124D+S125P+N194Y+T182*+G183*; P124D+S125P+G475K+S243Q+R180*+S181*; P124D+S125N+R180*+S181*; P124D+S125N+R180*+T182*; P124D+S125N+R180*+G183*; P124D+S125N+S181*+T182*; P124D+S125N+T182*+G183*; P124D+S125N+N194F+R180*+S181*; P124D+S125N+N194F+R180*+T182*; P124D+S125N+N194F+R180*+G183*; P124D+S125N+N194F+S181*+T182*; P124D+S125N+N194F+T182*+G183*; P124D+S125N+N194Y+R180*+S181*; P124D+S125N+N194Y+R180*+T182*; P124D+S125N+N194Y+R180*+G183*; P124D+S125N+N194Y+S181*+T182*; P124D+S125N+N194Y+T182*+G183*; P124D+S125N+G475K+S243Q+R180*+S181*; S125N+N174NN+R180*+S181*; S125N+N174NN+R180*+T182*; S125N+N174NN+R180*+G183*; S125N+N174NN+S181*+T182*; S125N+N174NN+T182*+G183*; S125N+N174NN+N194F+R180*+S181*; S125N+N174NN+N194F+R180*+T182*; S125N+N174NN+N194F+R180*+G183*; S125N+N174NN+N194F+S181*+T182*; S125N+N174NN+N194F+T182*+G183*; S125N+N174NN+N194Y+R180*+S181*; S125N+N174NN+N194Y+R180*+T182*; S125N+N174NN+N194Y+R180*+G183*; S125N+N174NN+N194Y+S181*+T182*; S125N+N174NN+N194Y+T182*+G183*; S125N+N174NN+G475K+S243Q+R180*+S181*; K172Q+N174NQ+R180*+S181*; K172Q+N174NQ+R180*+T182*; K172Q+N174NQ+R180*+G183*; K172Q+N174NQ+S181*+T182*; K172Q+N174NQ+T182*+G183*; K172Q+N174NQ+N194F+R180*+S181*; K172Q+N174NQ+N194F+R180*+T182*; K172Q+N174NQ+N194F+R180*+G183*; K172Q+N174NQ+N194F+S181*+T182*; K172Q+N174NQ+N194F+T182*+G183*; K172Q+N174NQ+N194Y+R180*+S181*; K172Q+N174NQ+N194Y+R180*+T182*; K172Q+N174NQ+N194Y+R180*+G183*; K172Q+N174NQ+N194Y+S181*+T182*; K172Q+N174NQ+N194Y+T182*+G183*; K172Q+N174NQ+G475K+S243Q+R180*+S181*; K172Q+L173F+R180*+S181*; K172Q+L173F+R180*+T182*; K172Q+L173F+R180*+G183*; K172Q+L173F+S181*+T182*; K172Q+L173F+T182*+G183*; K172Q+L173F+N194F+R180*+S181*; K172Q+L173F+N194F+R180*+T182*; K172Q+L173F+N194F+R180*+G183*; K172Q+L173F+N194F+S181*+T182*; K172Q+L173F+N194F+T182*+G183*; K172Q+L173F+N194Y+R180*+S181*; K172Q+L173F+N194Y+R180*+T182*; K172Q+L173F+N194Y+R180*+G183*; K172Q+L173F+N194Y+S181*+T182*; K172Q+L173F+N194Y+T182*+G183*; K172Q+L173F+G475K+S243Q+R180*+S181*; K172Q+L173F+N174NQ+R180*+S181*; K172Q+L173F+N174NQ+R180*+T182*; K172Q+L173F+N174NQ+R180*+G183*; K172Q+L173F+N174NQ+S181*+T182*; K172Q+L173F+N174NQ+T182*+G183*; K172Q+L173F+N174NQ+N194F+R180*+S181*; K172Q+L173F+N174NQ+N194F+R180*+T182*; K172Q+L173F+N174NQ+N194F+R180*+G183*; K172Q+L173F+N174NQ+N194F+S181*+T182*; K172Q+L173F+N174NQ+N194F+T182*+G183*; K172Q+L173F+N174NQ+N194Y+R180*+S181*; K172Q+L173F+N174NQ+N194Y+R180*+T182*; K172Q+L173F+N174NQ+N194Y+R180*+G183*; K172Q+L173F+N174NQ+N194Y+S181*+T182*; K172Q+L173F+N174NQ+N194Y+T182*+G183*; K172Q+L173F+N174NQ+G475K+S243Q+R180*+S181*; Y242F+F266Y+R180*+S181*; Y242F+F266Y+R180*+T182*; Y242F+F266Y+R180*+G183*; Y242F+F266Y+S181*+T182*; Y242F+F266Y+T182*+G183*; Y242F+F266Y+N194F+R180*+S181*; Y242F+F266Y+N194F+R180*+T182*; Y242F+F266Y+N194F+R180*+G183*; Y242F+F266Y+N194F+S181*+T182*; Y242F+F266Y+N194F+T182*+G183*; Y242F+F266Y+N194Y+R180*+S181*; Y242F+F266Y+N194Y+R180*+T182*; Y242F+F266Y+N194Y+R180*+G183*; Y242F+F266Y+N194Y+S181*+T182*; Y242F+F266Y+N194Y+T182*+G183*; Y242F+F266Y+G475K+S243Q+R180*+S181*; Y269N+N294Y+R180*+S181*; Y269N+N294Y+R180*+T182*; Y269N+N294Y+R180*+G183*; Y269N+N294Y+S181*+T182*; Y269N+N294Y+T182*+G183*; Y269N+N294Y+N194F+R180*+S181*; Y269N+N294Y+N194F+R180*+T182*; Y269N+N294Y+N194F+R180*+G183*; Y269N+N294Y+N194F+S181*+T182*; Y269N+N294Y+N194F+T182*+G183*; Y269N+N294Y+N194Y+R180*+S181*; Y269N+N294Y+N194Y+R180*+T182*; Y269N+N294Y+N194Y+R180*+G183*; Y269N+N294Y+N194Y+S181*+T182*; Y269N+N294Y+N194Y+T182*+G183*; Y269N+N294Y+G475K+S243Q+R180*+S181*; G283S+L323H+R180*+S181*; G283S+L323H+R180*+T182*; G283S+L323H+R180*+G183*; G283S+L323H+S181*+T182*; G283S+L323H+T182*+G183*; G283S+L323H+N194F+R180*+S181*; G283S+L323H+N194F+R180*+T182*; G283S+L323H+N194F+R180*+G183*; G283S+L323H+N194F+S181*+T182*; G283S+L323H+N194F+T182*+G183*; G283S+L323H+N194Y+R180*+S181*; G283S+L323H+N194Y+R180*+T182*; G283S+L323H+N194Y+R180*+G183*; G283S+L323H+N194Y+S181*+T182*; G283S+L323H+N194Y+T182*+G183*; G283S+L323H+G475K+S243Q+R180*+S181*, wherein the variant has at least 80% and less than 100% sequence identity to the alpha-amylase of SEQ ID NO: 1.

In other embodiments, the variant comprises or consists of the following alterations of the mature polypeptide of SEQ ID NO: 2 (individual embodiments are separated by semicolon): D16Y+R180*+S181*; D16Y+R180*+T182*; D16Y+R180*+G183*; D16Y+S181*+T182*; D16Y+T182*+G183*; D16Y+N194F+R180*+S181*; D16Y+N194F+R180*+T182*; D16Y+N194F+R180*+G183*; D16Y+N194F+S181*+T182*; D16Y+N194F+T182*+G183*; D16Y+N194Y+R180*+S181*; D16Y+N194Y+R180*+T182*; D16Y+N194Y+R180*+G183*; D16Y+N194Y+S181*+T182*; D16Y+N194Y+T182*+G183*; D16Y+G475K+S243Q+R180*+S181*; N19D+R180*+S181*; N19D+R180*+T182*; N19D+R180*+G183*; N19D+S181*+T182*; N19D+T182*+G183*; N19D+N194F+R180*+S181*; N19D+N194F+R180*+T182*; N19D+N194F+R180*+G183*; N19D+N194F+S181*+T182*; N19D+N194F+T182*+G183*; N19D+N194Y+R180*+S181*; N19D+N194Y+R180*+T182*; N19D+N194Y+R180*+G183*; N19D+N194Y+S181*+T182*; N19D+N194Y+T182*+G183*; N19D+G475K+S243Q+R180*+S181*; Y48W+R180*+S181*; Y48W+R180*+T182*; Y48W+R180*+G183*; Y48W+S181*+T182*; Y48W+T182*+G183*; Y48W+N194F+R180*+S181*; Y48W+N194F+R180*+T182*; Y48W+N194F+R180*+

G183\*; Y48W+N194F+S181\*+T182\*; Y48W+N194F+ T182\*+G183\*; Y48W+N194F+R180\*+S181\*; Y48W+ N194Y+R180\*+T182\*; Y48W+N194Y+R180\*+G183\*; Y48W+N194Y+S181\*+T182\*; Y48W+N194Y+T182\*+ G183\*; Y48W+G475K+S243Q+R180\*+S181\*; Y48F+ R180\*+S181\*; Y48F+R180\*+T182\*; Y48F+R180\*+ G183\*; Y48F+S181\*+T182\*; Y48F+T182\*+G183\*; Y48F+N194F+R180\*+S181\*; Y48F+N194F+R180\*+ T182\*; Y48F+N194F+R180\*+G183\*; Y48F+N194F+ S181\*+T182\*; Y48F+N194F+T182\*+G183\*; Y48F+ N194Y+R180\*+S181\*; Y48F+N194Y+R180\*+T182\*; Y48F+N194Y+R180\*+G183\*; Y48F+N194Y+S181\*+ T182\*; Y48F+N194Y+T182\*+G183\*; Y48F+G475K+ S243Q+R180\*+S181\*; Q53R+R180\*+S181\*; Q53R+ R180\*+T182\*; Q53R+R180\*+G183\*; Q53R+S181\*+ T182\*; Q53R+T182\*+G183\*; Q53R+N194F+R180\*+ S181\*; Q53R+N194F+R180\*+T182\*; Q53R+N194F+ R180\*+G183\*; Q53R+N194F+S181\*+T182\*; Q53R+ N194F+T182\*+G183\*; Q53R+N194Y+R180\*+S181\*; Q53R+N194Y+R180\*+T182\*; Q53R+N194Y+R180\*+ G183\*; Q53R+N194Y+S181\*+T182\*; Q53R+N194Y+ T182\*+G183\*; Q53R+G475K+S243Q+R180\*+S181\*; V60A+R180\*+S181\*; V60A+R180\*+T182\*; V60A+ R180\*+G183\*; V60A+S181\*+T182\*; V60A+T182\*+ G183\*; V60A+N194F+R180\*+S181\*; V60A+N194F+ R180\*+T182\*; V60A+N194F+R180\*+G183\*; V60A+ N194F+S181\*+T182\*; V60A+N194F+T182\*+G183\*; V60A+N194Y+R180\*+S181\*; V60A+N194Y+R180\*+ T182\*; V60A+N194Y+R180\*+G183\*; V60A+N194Y+ S181\*+T182\*; V60A+N194Y+T182\*+G183\*; V60A+ G475K+S243Q+R180\*+S181\*; F105M+R180\*+S181\*; F105M+R180\*+T182\*; F105M+R180\*+G183\*; F105M+ S181\*+T182\*; F105M+T182\*+G183\*; F105M+N194F+ R180\*+S181\*; F105M+N194F+R180\*+T182\*; F105M+ N194F+R180\*+G183\*; F105M+N194F+S181\*+T182\*; F105M+N194F+T182\*+G183\*; F105M+N194Y+R180\*+ S181\*; F105M+N194Y+R180\*+T182\*; F105M+N194Y+ R180\*+G183\*; F105M+N194Y+S181\*+T182\*; F105M+ N194Y+T182\*+G183\*; F105M+G475K+S243Q+R180\*+ S181\*; F116W+R180\*+S181\*; F116W+R180\*+T182\*; F116W+R180\*+G183\*; F116W+S181\*+T182\*; F116W+ T182\*+G183\*; F116W+N194F+R180\*+S181\*; F116W+ N194F+R180\*+T182\*; F116W+N194F+R180\*+G183\*; F116W+N194F+S181\*+T182\*; F116W+N194F+T182\*+ G183\*; F116W+N194Y+R180\*+S181\*; F116W+N194Y+ R180\*+T182\*; F116W+N194Y+R180\*+G183\*; F116W+ N194Y+S181\*+T182\*; F116W+N194Y+T182\*+G183\*; F116W+G475K+S243Q+R180\*+S181\*; P124\*+R180\*+ S181\*; P124\*+R180\*+T182\*; P124\*+R180\*+G183\*; P124\*+S181\*+T182\*; P124\*+T182\*+G183\*; P124\*+ N194F+R180\*+S181\*; P124\*+N194F+R180\*+T182\*; P124\*+N194F+R180\*+G183\*; P124\*+N194F+S181\*+ T182\*; P124\*+N194F+T182\*+G183\*; P124\*+N194Y+ R180\*+S181\*; P124\*+N194Y+R180\*+T182\*; P124\*+ N194Y+R180\*+G183\*; P124\*+N194Y+S181\*+T182\*; P124\*+N194Y+T182\*+G183\*; P124\*+G475K+S243Q+ R180\*+S181\*; P124D+R180\*+S181\*; P124D+R180\*+ T182\*; P124D+R180\*+G183\*; P124D+S181\*+T182\*; P124D+T182\*+G183\*; P124D+N194F+R180\*+S181\*; P124D+N194F+R180\*+T182\*; P124D+N194F+R180\*+ G183\*; P124D+N194F+S181\*+T182\*; P124D+N194F+ T182\*+G183\*; P124D+N194Y+R180\*+S181\*; P124D+ N194Y+R180\*+T182\*; P124D+N194Y+R180\*+G183\*; P124D+N194Y+S181\*+T182\*; P124D+N194Y+T182\*+ G183\*; P124D+G475K+S243Q+R180\*+S181\*; P124S+ R180\*+S181\*; P124S+R180\*+T182\*; P124S+R180\*+ G183\*; P124S+S181\*+T182\*; P124S+T182\*+G183\*; P124S+N194F+R180\*+S181\*; P124S+N194F+R180\*+ T182\*; P124S+N194F+R180\*+G183\*; P124S+N194F+ S181\*+T182\*; P124S+N194F+T182\*+G183\*; P124S+ N194Y+R180\*+S181\*; P124S+N194Y+R180\*+T182\*; P124S+N194Y+R180\*+G183\*; P124S+N194Y+S181\*+ T182\*; P124S+N194Y+T182\*+G183\*; P124S+G475K+ S243Q+R180\*+S181\*; P124T+R180\*+S181\*; P124T+ R180\*+T182\*; P124T+R180\*+G183\*; P124T+S181\*+ T182\*; P124T+T182\*+G183\*; P124T+N194F+R180\*+ S181\*; P124T+N194F+R180\*+T182\*; P124T+N194F+ R180\*+G183\*; P124T+N194F+S181\*+T182\*; P124T+ N194F+T182\*+G183\*; P124T+N194Y+R180\*+S181\*; P124T+N194Y+R180\*+T182\*; P124T+N194Y+R180\*+ G183\*; P124T+N194Y+S181\*+T182\*; P124T+N194Y+ T182\*+G183\*; P124T+G475K+S243Q+R180\*+S181\*; S125N+R180\*+S181\*; S125N+R180\*+T182\*; S125N+ R180\*+G183\*; S125N+S181\*+T182\*; S125N+T182\*+ G183\*; S125N+N194F+R180\*+S181\*; S125N+N194F+ R180\*+T182\*; S125N+N194F+R180\*+G183\*; S125N+ N194F+S181\*+T182\*; S125N+N194F+T182\*+G183\*; S125N+N194Y+R180\*+S181\*; S125N+N194Y+R180\*+ T182\*; S125N+N194Y+R180\*+G183\*; S125N+N194Y+ S181\*+T182\*; S125N+N194Y+T182\*+G183\*; S125N+ G475K+S243Q+R180\*+S181\*; S125P+R180\*+S181\*; S125P+R180\*+T182\*; S125P+R180\*+G183\*; S125P+ S181\*+T182\*; S125P+T182\*+G183\*; S125P+N194F+ R180\*+S181\*; S125P+N194F+R180\*+T182\*; S125P+ N194F+R180\*+G183\*; S125P+N194F+S181\*+T182\*; S125P+N194F+T182\*+G183\*; S125P+N194Y+R180\*+ S181\*; S125P+N194Y+R180\*+T182\*; S125P+N194Y+ R180\*+G183\*; S125P+N194Y+S181\*+T182\*; S125P+ N194Y+T182\*+G183\*; S125P+G475K+S243Q+R180\*+ S181\*; N128F+R180\*+S181\*; N128F+R180\*+T182\*; N128F+R180\*+G183\*; N128F+S181\*+T182\*; N128F+ T182\*+G183\*; N128F+N194F+R180\*+S181\*; N128F+ N194F+R180\*+T182\*; N128F+N194F+R180\*+G183\*; N128F+N194F+S181\*+T182\*; N128F+N194F+T182\*+ G183\*; N128F+N194Y+R180\*+S181\*; N128F+N194Y+ R180\*+T182\*; N128F+N194Y+R180\*+G183\*; N128F+ N194Y+S181\*+T182\*; N128F+N194Y+T182\*+G183\*; N128F+G475K+S243Q+R180\*+S181\*; N128H+R180\*+ S181\*; N128H+R180\*+T182\*; N128H+R180\*+G183\*; N128H+S181\*+T182\*; N128H+T182\*+G183\*; N128H+ N194F+R180\*+S181\*; N128H+N194F+R180\*+T182\*; N128H+N194F+R180\*+G183\*; N128H+N194F+S181\*+ T182\*; N128H+N194F+T182\*+G183\*; N128H+N194Y+ R180\*+S181\*; N128H+N194Y+R180\*+T182\*; N128H+ N194Y+R180\*+G183\*; N128H+N194Y+S181\*+T182\*; N128H+N194Y+T182\*+G183\*; N128H+G475K+S243Q+ R180\*+S181\*; N128I+R180\*+S181\*; N128I+R180\*+ T182\*; N128I+R180\*+G183\*; N128I+S181\*+T182\*; N128I+T182\*+G183\*; N128I+N194F+R180\*+S181\*; N128I+N194F+R180\*+T182\*; N128I+N194F+R180\*+ G183\*; N128I+N194F+S181\*+T182\*; N128I+N194F+ T182\*+G183\*; N128I+N194Y+R180\*+S181\*; N128I+ N194Y+R180\*+T182\*; N128I+N194Y+R180\*+G183\*; N128I+N194Y+S181\*+T182\*; N128I+N194Y+T182\*+ G183\*; N128I+G475K+S243Q+R180\*+S181\*; N128K+ R180\*+S181\*; N128K+R180\*+T182\*; N128K+R180\*+ G183\*; N128K+S181\*+T182\*; N128K+T182\*+G183\*; N128K+N194F+R180\*+S181\*; N128K+N194F+R180\*+ T182\*; N128K+N194F+R180\*+G183\*; N128K+N194F+ S181\*+T182\*; N128K+N194F+T182\*+G183\*; N128K+ N194Y+R180\*+S181\*; N128K+N194Y+R180\*+T182\*; N128K+N194Y+R180\*+G183\*; N128K+N194Y+S181\*+ T182\*; N128K+N194Y+T182\*+G183\*; N128K+G475K+ S243Q+R180\*+S181\*; N128R+R180\*+S181\*; N128R+

R180*+T182*; N128R+R180*+G183*; N128R+S181*+ T182*; N128R+T182*+G183*; N128R+N194F+R180*+ S181*; N128R+N194F+R180*+T182*; N128R+N194F+ R180*+G183*; N128R+N194F+S181*+T182*; N128R+ N194F+T182*+G183*; N128R+N194Y+R180*+S181*; N128R+N194Y+R180*+T182*; N128R+N194Y+R180*+ G183*; N128R+N194Y+S181*+T182*; N128R+N194Y+ T182*+G183*; N128R+G475K+S243Q+R180*+S181*; T131D+R180*+S181*; T131 D+R180*+T182*; T131 D+R180*+G183*; T131D+S181*+T182*; T131D+T182*+ G183*; T131D+N194F+R180*+S181*; T131D+N194F+ R180*+T182*; T131D+N194F+R180*+G183*; T131D+ N194F+S181*+T182*; T131D+N194F+T182*+G183*; T131D+N194Y+R180*+S181*; T131D+N194Y+R180*+ T182*; T131D+N194Y+R180*+G183*; T131D+N194Y+ S181*+T182*; T131D+N194Y+T182*+G183*; T131 D+G475K+S243Q+R180*+S181*; T131E+R180*+S181*; T131E+R180*+T182*; T131E+R180*+G183*; T131E+ S181*+T182*; T131E+T182*+G183*; T131E+N194F+ R180*+S181*; T131E+N194F+R180*+T182*; T131E+ N194F+R180*+G183*; T131E+N194F+S181*+T182*; T131E+N194F+T182*+G183*; T131E+N194Y+R180*+ S181*; T131E+N194Y+R180*+T182*; T131E+N194Y+ R180*+G183*; T131E+N194Y+S181*+T182*; T131E+ N194Y+T182*+G183*; T131E+G475K+S243Q+R180*+ S181*; T131L+R180*+S181*; T131L+R180*+T182*; T131L+R180*+G183*; T131L+S181*+T182*; T131L+ T182*+G183*; T131L+N194F+R180*+S181*; T131L+ N194F+R180*+T182*; T131L+N194F+R180*+G183*; T131L+N194F+S181*+T182*; T131L+N194F+T182*+ G183*; T131L+N194Y+R180*+S181*; T131L+N194Y+ R180*+T182*; T131L+N194Y+R180*+G183*; T131L+ N194Y+S181*+T182*; T131L+N194Y+T182*+G183*; T131 L+G475K+S243Q+R180*+S181*; G133D+R180*+ S181*; G133D+R180*+T182*; G133D+R180*+G183*; G133D+S181*+T182*; G133D+T182*+G183*; G133D+ N194F+R180*+S181*; G133D+N194F+R180*+T182*; G133D+N194F+R180*+G183*; G133D+N194F+S181*+ T182*; G133D+N194F+T182*+G183*; G133D+N194Y+ R180*+S181*; G133D+N194Y+R180*+T182*; G133D+ N194Y+R180*+G183*; G133D+N194Y+S181*+T182*; G133D+N194Y+T182*+G183*; G133D+G475K+S243Q+ R180*+S181*; K172Q+R180*+S181*; K172Q+R180*+ T182*; K172Q+R180*+G183*; K172Q+S181*+T182*; K172Q+T182*+G183*; K172Q+N194F+R180*+S181*; K172Q+N194F+R180*+T182*; K172Q+N194F+R180*+ G183*; K172Q+N194F+S181*+T182*; K172Q+N194F+ T182*+G183*; K172Q+N194Y+R180*+S181*; K172Q+ N194Y+R180*+T182*; K172Q+N194Y+R180*+G183*; K172Q+N194Y+S181*+T182*; K172Q+N194Y+T182*+ G183*; K172Q+G475K+S243Q+R180*+S181*; L173F+ R180*+S181*; L173F+R180*+T182*; L173F+R180*+ G183*; L173F+S181*+T182*; L173F+T182*+G183*; L173F+N194F+R180*+S181*; L173F+N194F+R180*+ T182*; L173F+N194F+R180*+G183*; L173F+N194F+ S181*+T182*; L173F+N194F+T182*+G183*; L173F+ N194Y+R180*+S181*; L173F+N194Y+R180*+T182*; L173F+N194Y+R180*+G183*; L173F+N194Y+S181*+ T182*; L173F+N194Y+T182*+G183*; L173F+G475K+ S243Q+R180*+S181*; L173Y+R180*+S181*; L173Y+ R180*+T182*; L173Y+R180*+G183*; L173Y+S181*+ T182*; L173Y+T182*+G183*; L173Y+N194F+R180*+ S181*; L173Y+N194F+R180*+T182*; L173Y+N194F+ R180*+G183*; L173Y+N194F+S181*+T182*; L173Y+ N194F+T182*+G183*; L173Y+N194Y+R180*+S181*; L173Y+N194Y+R180*+T182*; L173Y+N194Y+R180*+ G183*; L173Y+N194Y+S181*+T182*; L173Y+N194Y+ T182*+G183*; L173Y+G475K+S243Q+R180*+S181*; N174NQ+R180*+S181*; N174NQ+R180*+T182*; N174NQ+R180*+G183*; N174NQ+S181*+T182*; N174NQ+T182*+G183*; N174NQ+N194F+R180*+ S181*; N174NQ+N194F+R180*+T182*; N174NQ+ N194F+R180*+G183*; N174NQ+N194F+S181*+T182*; N174NQ+N194F+T182*+G183*; N174NQ+N194Y+ R180*+S181*; N174NQ+N194Y+R180*+T182*; N174NQ+N194Y+R180*+G183*; N174NQ+N194Y+ S181*+T182*; N174NQ+N194Y+T182*+G183*; N174NQ+G475K+S243Q+R180*+S181*; N174NN+ R180*+S181*; N174NN+R180*+T182*; N174NN+ R180*+G183*; N174NN+S181*+T182*; N174NN+ T182*+G183*; N174NN+N194F+R180*+S181*; N174NN+N194F+R180*+T182*; N174NN+N194F+ R180*+G183*; N174NN+N194F+S181*+T182*; N174NN+N194F+T182*+G183*; N174NN+N194Y+ R180*+S181*; N174NN+N194Y+R180*+T182*; N174NN+N194Y+R180*+G183*; N174NN+N194Y+ S181*+T182*; N174NN+N194Y+T182*+G183*; N174NN+G475K+S243Q+R180*+S181*; N174NE+ R180*+S181*; N174NE+R180*+T182*; N174NE+R180*+ G183*; N174NE+S181*+T182*; N174NE+T182*+G183*; N174NE+N194F+R180*+S181*; N174NE+N194F+ R180*+T182*; N174NE+N194F+R180*+G183*; N174NE+N194F+S181*+T182*; N174NE+N194F+ T182*+G183*; N174NE+N194Y+R180*+S181*; N174NE+N194Y+R180*+T182*; N174NE+N194Y+ R180*+G183*; N174NE+N194Y+S181*+T182*; N174NE+N194Y+T182*+G183*; N174NE+G475K+ S243Q+R180*+S181*; N174ND+R180*+S181*; N174ND+R180*+T182*; N174ND+R180*+G183*; N174ND+S181*+T182*; N174ND+T182*+G183*; N174ND+N194F+R180*+S181*; N174ND+N194F+ R180*+T182*; N174ND+N194F+R180*+G183*; N174ND+N194F+S181*+T182*; N174ND+N194F+ T182*+G183*; N174ND+N194Y+R180*+S181*; N174ND+N194Y+R180*+T182*; N174ND+N194Y+ R180*+G183*; N174ND+N194Y+S181*+T182*; N174ND+N194Y+T182*+G183*; N174ND+G475K+ S243Q+R180*+S181*; K178L+R180*+S181*; K178L+ R180*+T182*; K178L+R180*+G183*; K178L+S181*+ T182*; K178L+T182*+G183*; K178L+N194F+R180*+ S181*; K178L+N194F+R180*+T182*; K178L+N194F+ R180*+G183*; K178L+N194F+S181*+T182*; K178L+ N194F+T182*+G183*; K178L+N194Y+R180*+S181*; K178L+N194Y+R180*+T182*; K178L+N194Y+R180*+ G183*; K178L+N194Y+S181*+T182*; K178L+N194Y+ T182*+G183*; K178L+G475K+S243Q+R180*+S181*; A185F+R180*+S181*; A185F+R180*+T182*; A185F+ R180*+G183*; A185F+S181*+T182*; A185F+T182*+ G183*; A185F+N194F+R180*+S181*; A185F+N194F+ R180*+T182*; A185F+N194F+R180*+G183*; A185F+ N194F+S181*+T182*; A185F+N194F+T182*+G183*; A185F+N194Y+R180*+S181*; A185F+N194Y+R180*+ T182*; A185F+N194Y+R180*+G183*; A185F+N194Y+ S181*+T182*; A185F+N194Y+T182*+G183*; A185F+ G475K+S243Q+R180*+S181*; A185H+R180*+S181*; A185H+R180*+T182*; A185H+R180*+G183*; A185H+ S181*+T182*; A185H+T182*+G183*; A185H+N194F+ R180*+S181*; A185H+N194F+R180*+T182*; A185H+ N194F+R180*+G183*; A185H+N194F+S181*+T182*; A185H+N194F+T182*+G183*; A185H+N194Y+R180*+ S181*; A185H+N194Y+R180*+T182*; A185H+N194Y+ R180*+G183*; A185H+N194Y+S181*+T182*; A185H+ N194Y+T182*+G183*; A185H+G475K+S243Q+R180*+ S181*; A185L+R180*+S181*; A185L+R180*+T182*;

A185L+R180*+G183*; A185L+S181*+T182*; A185L+T182*+G183*; A185L+N194F+R180*+S181*; A185L+N194F+R180*+T182*; A185L+N194F+R180*+G183*; A185L+N194F+S181*+T182*; A185L+N194F+T182*+G183*; A185L+N194Y+R180*+S181*; A185L+N194Y+R180*+T182*; A185L+N194Y+R180*+G183*; A185L+N194Y+S181*+T182*; A185L+N194Y+T182*+G183*; A185L+G475K+S243Q+R180*+S181*; A185I+R180*+S181*; A185I+R180*+T182*; A185I+R180*+G183*; A185I+S181*+T182*; A185I+T182*+G183*; A185I+N194F+R180*+S181*; A185I+N194F+R180*+T182*; A185I+N194F+R180*+G183*; A185I+N194F+S181*+T182*; A185I+N194F+T182*+G183*; A185I+N194Y+R180*+S181*; A185I+N194Y+R180*+T182*; A185I+N194Y+R180*+G183*; A185I+N194Y+S181*+T182*; A185I+N194Y+T182*+G183*; A185I+G475K+S243Q+R180*+S181*; A185P+R180*+S181*; A185P+R180*+T182*; A185P+R180*+G183*; A185P+S181*+T182*; A185P+T182*+G183*; A185P+N194F+R180*+S181*; A185P+N194F+R180*+T182*; A185P+N194F+R180*+G183*; A185P+N194F+S181*+T182*; A185P+N194F+T182*+G183*; A185P+N194Y+R180*+S181*; A185P+N194Y+R180*+T182*; A185P+N194Y+R180*+G183*; A185P+N194Y+S181*+T182*; A185P+N194Y+T182*+G183*; A185P+G475K+S243Q+R180*+S181*; E189P+R180*+S181*; E189P+R180*+T182*; E189P+R180*+G183*; E189P+S181*+T182*; E189P+T182*+G183*; E189P+N194F+R180*+S181*; E189P+N194F+R180*+T182*; E189P+N194F+R180*+G183*; E189P+N194F+S181*+T182*; E189P+N194F+T182*+G183*; E189P+N194Y+R180*+S181*; E189P+N194Y+R180*+T182*; E189P+N194Y+R180*+G183*; E189P+N194Y+S181*+T182*; E189P+N194Y+T182*+G183*; E189P+G475K+S243Q+R180*+S181*; N194F+R180*+S181*; N194F+R180*+T182*; N194F+R180*+G183*; N194F+S181*+T182*; N194F+T182*+G183*; N194F+G475K+S243Q+R180*+S181*; N194Y+R180*+S181*; N194Y+R180*+T182*; N194Y+R180*+G183*; N194Y+S181*+T182*; N194Y+T182*+G183*; N194Y+G475K+S243Q+R180*+S181*; N194H+R180*+S181*; N194H+R180*+T182*; N194H+R180*+G183*; N194H+S181*+T182*; N194H+T182*+G183*; N194H+G475K+S243Q+R180*+S181*; N194L+R180*+S181*; N194L+R180*+T182*; N194L+R180*+G183*; N194L+S181*+T182*; N194L+T182*+G183*; N194L+G475K+S243Q+R180*+S181*; N194I+R180*+S181*; N194I+R180*+T182*; N194I+R180*+G183*; N194I+S181*+T182*; N194I+T182*+G183*; N194I+G475K+S243Q+R180*+S181*; A203S+R180*+S181*; A203S+R180*+T182*; A203S+R180*+G183*; A203S+S181*+T182*; A203S+T182*+G183*; A203S+N194F+R180*+S181*; A203S+N194F+R180*+T182*; A203S+N194F+R180*+G183*; A203S+N194F+S181*+T182*; A203S+N194F+T182*+G183*; A203S+N194Y+R180*+S181*; A203S+N194Y+R180*+T182*; A203S+N194Y+R180*+G183*; A203S+N194Y+S181*+T182*; A203S+N194Y+T182*+G183*; A203S+G475K+S243Q+R180*+S181*; A203T+R180*+S181*; A203T+R180*+T182*; A203T+R180*+G183*; A203T+S181*+T182*; A203T+T182*+G183*; A203T+N194F+R180*+S181*; A203T+N194F+R180*+T182*; A203T+N194F+R180*+G183*; A203T+N194F+S181*+T182*; A203T+N194F+T182*+G183*; A203T+N194Y+R180*+S181*; A203T+N194Y+R180*+T182*; A203T+N194Y+R180*+G183*; A203T+N194Y+S181*+T182*; A203T+N194Y+T182*+G183*; A203T+G475K+S243Q+R180*+S181*; L205F+R180*+S181*; L205F+R180*+T182*; L205F+R180*+G183*; L205F+S181*+T182*; L205F+T182*+G183*; L205F+N194F+R180*+S181*; L205F+N194F+R180*+T182*; L205F+N194F+R180*+G183*; L205F+N194F+S181*+T182*; L205F+N194F+T182*+G183*; L205F+N194Y+R180*+S181*; L205F+N194Y+R180*+T182*; L205F+N194Y+R180*+G183*; L205F+N194Y+S181*+T182*; L205F+N194Y+T182*+G183*; L205F+G475K+S243Q+R180*+S181*; L205Y+R180*+S181*; L205Y+R180*+T182*; L205Y+R180*+G183*; L205Y+S181*+T182*; L205Y+T182*+G183*; L205Y+N194F+R180*+S181*; L205Y+N194F+R180*+T182*; L205Y+N194F+R180*+G183*; L205Y+N194F+S181*+T182*; L205Y+N194F+T182*+G183*; L205Y+N194Y+R180*+S181*; L205Y+N194Y+R180*+T182*; L205Y+N194Y+R180*+G183*; L205Y+N194Y+S181*+T182*; L205Y+N194Y+T182*+G183*; L205Y+G475K+S243Q+R180*+S181*; L205I+R180*+S181*; L205I+R180*+T182*; L205I+R180*+G183*; L205I+S181*+T182*; L205I+T182*+G183*; L205I+N194F+R180*+S181*; L205I+N194F+R180*+T182*; L205I+N194F+R180*+G183*; L205I+N194F+S181*+T182*; L205I+N194F+T182*+G183*; L205I+N194Y+R180*+S181*; L205I+N194Y+R180*+T182*; L205I+N194Y+R180*+G183*; L205I+N194Y+S181*+T182*; L205I+N194Y+T182*+G183*; L205I+G475K+S243Q+R180*+S181*; M208F+R180*+S181*; M208F+R180*+T182*; M208F+R180*+G183*; M208F+S181*+T182*; M208F+T182*+G183*; M208F+N194F+R180*+S181*; M208F+N194F+R180*+T182*; M208F+N194F+R180*+G183*; M208F+N194F+S181*+T182*; M208F+N194F+T182*+G183*; M208F+N194Y+R180*+S181*; M208F+N194Y+R180*+T182*; M208F+N194Y+R180*+G183*; M208F+N194Y+S181*+T182*; M208F+N194Y+T182*+G183*; M208F+G475K+S243Q+R180*+S181*; M208I+R180*+S181*; M208I+R180*+T182*; M208I+R180*+G183*; M208I+S181*+T182*; M208I+T182*+G183*; M208I+N194F+R180*+S181*; M208I+N194F+R180*+T182*; M208I+N194F+R180*+G183*; M208I+N194F+S181*+T182*; M208I+N194F+T182*+G183*; M208I+N194Y+R180*+S181*; M208I+N194Y+R180*+T182*; M208I+N194Y+R180*+G183*; M208I+N194Y+S181*+T182*; M208I+N194Y+T182*+G183*; M208I+G475K+S243Q+R180*+S181*; M208L+R180*+S181*; M208L+R180*+T182*; M208L+R180*+G183*; M208L+S181*+T182*; M208L+T182*+G183*; M208L+N194F+R180*+S181*; M208L+N194F+R180*+T182*; M208L+N194F+R180*+G183*; M208L+N194F+S181*+T182*; M208L+N194F+T182*+G183*; M208L+N194Y+R180*+S181*; M208L+N194Y+R180*+T182*; M208L+N194Y+R180*+G183*; M208L+N194Y+S181*+T182*; M208L+N194Y+T182*+G183*; M208L+G475K+S243Q+R180*+S181*; M208Y+R180*+S181*; M208Y+R180*+T182*; M208Y+R180*+G183*; M208Y+S181*+T182*; M208Y+T182*+G183*; M208Y+N194F+R180*+S181*; M208Y+N194F+R180*+T182*; M208Y+N194F+R180*+G183*; M208Y+N194F+S181*+T182*; M208Y+N194F+T182*+G183*; M208Y+N194Y+R180*+S181*; M208Y+N194Y+R180*+T182*; M208Y+N194Y+R180*+G183*; M208Y+N194Y+S181*+T182*; M208Y+N194Y+T182*+G183*; M208Y+G475K+S243Q+R180*+S181*; H209D+R180*+S181*; H209D+R180*+T182*; H209D+R180*+G183*; H209D+S181*+T182*; H209D+T182*+G183*; H209D+N194F+R180*+S181*; H209D+N194F+R180*+T182*; H209D+N194F+R180*+G183*; H209D+N194F+S181*+T182*; H209D+N194F+T182*+G183*; H209D+N194Y+R180*+S181*; H209D+N194Y+R180*+T182*; H209D+N194Y+R180*+G183*; H209D+N194Y+S181*+T182*; H209D+N194Y+T182*+G183*; H209D+G475K+S243Q+R180*+S181*; H209M+R180*+S181*; H209M+

R180*+T182*; H209M+R180*+G183*; H209M+S181*+T182*; H209M+T182*+G183*; H209M+N194F+R180*+S181*; H209M+N194F+R180*+T182*; H209M+N194F+R180*+G183*; H209M+N194F+S181*+T182*; H209M+N194F+T182*+G183*; H209M+N194Y+R180*+S181*; H209M+N194Y+R180*+T182*; H209M+N194Y+R180*+G183*; H209M+N194Y+S181*+T182*; H209M+N194Y+T182*+G183*; H209M+G475K+S243Q+R180*+S181*; H209T+R180*+S181*; H209T+R180*+T182*; H209T+R180*+G183*; H209T+S181*+T182*; H209T+T182*+G183*; H209T+N194F+R180*+S181*; H209T+N194F+R180*+T182*; H209T+N194F+R180*+G183*; H209T+N194F+S181*+T182*; H209T+N194F+T182*+G183*; H209T+N194Y+R180*+S181*; H209T+N194Y+R180*+T182*; H209T+N194Y+R180*+G183*; H209T+N194Y+S181*+T182*; H209T+N194Y+T182*+G183*; H209T+G475K+S243Q+R180*+S181*; E211D+R180*+S181*; E211D+R180*+T182*; E211D+R180*+G183*; E211D+S181*+T182*; E211D+T182*+G183*; E211D+N194F+R180*+S181*; E211D+N194F+R180*+T182*; E211D+N194F+R180*+G183*; E211D+N194F+S181*+T182*; E211D+N194F+T182*+G183*; E211D+N194Y+R180*+S181*; E211D+N194Y+R180*+T182*; E211D+N194Y+R180*+G183*; E211D+N194Y+S181*+T182*; E211D+N194Y+T182*+G183*; E211D+G475K+S243Q+R180*+S181*; E211L+R180*+S181*; E211L+R180*+T182*; E211L+R180*+G183*; E211L+S181*+T182*; E211L+T182*+G183*; E211L+N194F+R180*+S181*; E211L+N194F+R180*+T182*; E211L+N194F+R180*+G183*; E211L+N194F+S181*+T182*; E211L+N194F+T182*+G183*; E211L+N194Y+R180*+S181*; E211L+N194Y+R180*+T182*; E211L+N194Y+R180*+G183*; E211L+N194Y+S181*+T182*; E211L+N194Y+T182*+G183*; E211L+G475K+S243Q+R180*+S181*; Y48W+R180*+S181*; Y48W+R180*+T182*; Y48W+R180*+G183*; Y48W+S181*+T182*; Y48W+T182*+G183*; Y48W+N194F+R180*+S181*; Y48W+N194F+R180*+T182*; Y48W+N194F+R180*+G183*; Y48W+N194F+S181*+T182*; Y48W+N194F+T182*+G183*; Y48W+N194Y+R180*+S181*; Y48W+N194Y+R180*+T182*; Y48W+N194Y+R180*+G183*; Y48W+N194Y+S181*+T182*; Y48W+N194Y+T182*+G183*; Y48W+G475K+S243Q+R180*+S181*; V212A+R180*+S181*; V212A+R180*+T182*; V212A+R180*+G183*; V212A+S181*+T182*; V212A+T182*+G183*; V212A+N194F+R180*+S181*; V212A+N194F+R180*+T182*; V212A+N194F+R180*+G183*; V212A+N194F+S181*+T182*; V212A+N194F+T182*+G183*; V212A+N194Y+R180*+S181*; V212A+N194Y+R180*+T182*; V212A+N194Y+R180*+G183*; V212A+N194Y+S181*+T182*; V212A+N194Y+T182*+G183*; V212A+G475K+S243Q+R180*+S181*; R309Q+R180*+S181*; R309Q+R180*+T182*; R309Q+R180*+G183*; R309Q+S181*+T182*; R309Q+T182*+G183*; R309Q+N194F+R180*+S181*; R309Q+N194F+R180*+T182*; R309Q+N194F+R180*+G183*; R309Q+N194F+S181*+T182*; R309Q+N194F+T182*+G183*; R309Q+N194Y+R180*+S181*; R309Q+N194Y+R180*+T182*; R309Q+N194Y+R180*+G183*; R309Q+N194Y+S181*+T182*; R309Q+N194Y+T182*+G183*; R309Q+G475K+S243Q+R180*+S181*; I390E+R180*+S181*; I390E+R180*+T182*; I390E+R180*+G183*; I390E+S181*+T182*; I390E+T182*+G183*; I390E+N194F+R180*+S181*; I390E+N194F+R180*+T182*; I390E+N194F+R180*+G183*; I390E+N194F+S181*+T182*; I390E+N194F+T182*+G183*; I390E+N194Y+R180*+S181*; I390E+N194Y+R180*+T182*; I390E+N194Y+R180*+G183*; I390E+N194Y+S181*+T182*; I390E+N194Y+T182*+G183*; I390E+G475K+S243Q+R180*+S181*; V212P+R180*+S181*; V212P+R180*+T182*; V212P+R180*+G183*; V212P+S181*+T182*; V212P+T182*+G183*; V212P+N194F+R180*+S181*; V212P+N194F+R180*+T182*; V212P+N194F+R180*+G183*; V212P+N194F+S181*+T182*; V212P+N194F+T182*+G183*; V212P+N194Y+R180*+S181*; V212P+N194Y+R180*+T182*; V212P+N194Y+R180*+G183*; V212P+N194Y+S181*+T182*; V212P+N194Y+T182*+G183*; V212P+G475K+S243Q+R180*+S181*; V212N+R180*+S181*; V212N+R180*+T182*; V212N+R180*+G183*; V212N+S181*+T182*; V212N+T182*+G183*; V212N+N194F+R180*+S181*; V212N+N194F+R180*+T182*; V212N+N194F+R180*+G183*; V212N+N194F+S181*+T182*; V212N+N194F+T182*+G183*; V212N+N194Y+R180*+S181*; V212N+N194Y+R180*+T182*; V212N+N194Y+R180*+G183*; V212N+N194Y+S181*+T182*; V212N+N194Y+T182*+G183*; V212N+G475K+S243Q+R180*+S181*; V212I+R180*+S181*; V212I+R180*+T182*; V212I+R180*+G183*; V212I+S181*+T182*; V212I+T182*+G183*; V212I+N194F+R180*+S181*; V212I+N194F+R180*+T182*; V212I+N194F+R180*+G183*; V212I+N194F+S181*+T182*; V212I+N194F+T182*+G183*; V212I+N194Y+R180*+S181*; V212I+N194Y+R180*+T182*; V212I+N194Y+R180*+G183*; V212I+N194Y+S181*+T182*; V212I+N194Y+T182*+G183*; V212I+G475K+S243Q+R180*+S181*; N174NN+R180*+S181*; N174NN+R180*+T182*; N174NN+R180*+G183*; N174NN+S181*+T182*; N174NN+T182*+G183*; N174NN+N194F+R180*+S181*; N174NN+N194F+R180*+T182*; N174NN+N194F+R180*+G183*; N174NN+N194F+S181*+T182*; N174NN+N194F+T182*+G183*; N174NN+N194Y+R180*+S181*; N174NN+N194Y+R180*+T182*; N174NN+N194Y+R180*+G183*; N174NN+N194Y+S181*+T182*; N174NN+N194Y+T182*+G183*; N174NN+G475K+S243Q+R180*+S181*; V213S+R180*+S181*; V213S+R180*+T182*; V213S+R180*+G183*; V213S+S181*+T182*; V213S+T182*+G183*; V213S+N194F+R180*+S181*; V213S+N194F+R180*+T182*; V213S+N194F+R180*+G183*; V213S+N194F+S181*+T182*; V213S+N194F+T182*+G183*; V213S+N194Y+R180*+S181*; V213S+N194Y+R180*+T182*; V213S+N194Y+R180*+G183*; V213S+N194Y+S181*+T182*; V213S+N194Y+T182*+G183*; V213S+G475K+S243Q+R180*+S181*; N174NQ+R180*+S181*; N174NQ+R180*+T182*; N174NQ+R180*+G183*; N174NQ+S181*+T182*; N174NQ+T182*+G183*; N174NQ+N194F+R180*+S181*; N174NQ+N194F+R180*+T182*; N174NQ+N194F+R180*+G183*; N174NQ+N194F+S181*+T182*; N174NQ+N194F+T182*+G183*; N174NQ+N194Y+R180*+S181*; N174NQ+N194Y+R180*+T182*; N174NQ+N194Y+R180*+G183*; N174NQ+N194Y+S181*+T182*; N174NQ+N194Y+T182*+G183*; N174NQ+G475K+S243Q+R180*+S181*; V213Q+R180*+S181*; V213Q+R180*+T182*; V213Q+R180*+G183*; V213Q+S181*+T182*; V213Q+T182*+G183*; V213Q+N194F+R180*+S181*; V213Q+N194F+R180*+T182*; V213Q+N194F+R180*+G183*; V213Q+N194F+S181*+T182*; V213Q+N194F+T182*+G183*; V213Q+N194Y+R180*+S181*; V213Q+N194Y+R180*+T182*; V213Q+N194Y+R180*+G183*; V213Q+N194Y+S181*+T182*; V213Q+N194Y+T182*+G183*; V213Q+G475K+S243Q+R180*+S181*; K241R+R180*+S181*; K241R+R180*+T182*; K241R+R180*+G183*; K241R+S181*+T182*; K241R+T182*+G183*; K241R+N194F+R180*+S181*; K241R+N194F+R180*+T182*; K241R+N194F+R180*+

G183*; K241R+N194F+S181*+T182*; K241R+N194F+ T182*+G183*; K241R+N194Y+R180*+S181*; K241R+ N194Y+R180*+T182*; K241R+N194Y+R180*+G183*; K241R+N194Y+S181*+T182*; K241R+N194Y+T182*+ G183*; K241R+G475K+S243Q+R180*+S181*; Y242F+ R180*+S181*; Y242F+R180*+T182*; Y242F+R180*+ G183*; Y242F+S181*+T182*; Y242F+T182*+G183*; Y242F+N194F+R180*+S181*; Y242F+N194F+R180*+ T182*; Y242F+N194F+R180*+G183*; Y242F+N194F+ S181*+T182*; Y242F+N194F+T182*+G183*; Y242F+ N194Y+R180*+S181*; Y242F+N194Y+R180*+T182*; Y242F+N194Y+R180*+G183*; Y242F+N194Y+S181*+ T182*; Y242F+N194Y+T182*+G183*; Y242F+G475K+ S243Q+R180*+S181*; F245I+R180*+S181*; F245I+ R180*+T182*; F245I+R180*+G183*; F245I+S181*+ T182*; F245I+T182*+G183*; F245I+N194F+R180*+ S181*; F245I+N194F+R180*+T182*; F245I+N194F+ R180*+G183*; F245I+N194F+S181*+T182*; F245I+ N194F+T182*+G183*; F245I+N194Y+R180*+S181*; F245I+N194Y+R180*+T182*; F245I+N194Y+R180*+ G183*; F245I+N194Y+S181*+T182*; F245I+N194Y+ T182*+G183*; F245I+G475K+S243Q+R180*+S181*; F245L+R180*+S181*; F245L+R180*+T182*; F245L+ R180*+G183*; F245L+S181*+T182*; F245L+T182*+ G183*; F245L+N194F+R180*+S181*; F245L+N194F+ R180*+T182*; F245L+N194F+R180*+G183*; F245L+ N194F+S181*+T182*; F245L+N194F+T182*+G183*; F245L+N194Y+R180*+S181*; F245L+N194Y+R180*+ T182*; F245L+N194Y+R180*+G183*; F245L+N194Y+ S181*+T182*; F245L+N194Y+T182*+G183*; F245L+ G475K+S243Q+R180*+S181*; F245M+R180*+S181*; F245M+R180*+T182*; F245M+R180*+G183*; F245M+ S181*+T182*; F245M+T182*+G183*; F245M+N194F+ R180*+S181*; F245M+N194F+R180*+T182*; F245M+ N194F+R180*+G183*; F245M+N194F+S181*+T182*; F245M+N194F+T182*+G183*; F245M+N194Y+R180*+ S181*; F245M+N194Y+R180*+T182*; F245M+N194Y+ R180*+G183*; F245M+N194Y+S181*+T182*; F245M+ N194Y+T182*+G183*; F245M+G475K+S243Q+R180*+ S181*; F245S+R180*+S181*; F245S+R180*+T182*; F245S+R180*+G183*; F245S+S181*+T182*; F245S+ T182*+G183*; F245S+N194F+R180*+S181*; F245S+ N194F+R180*+T182*; F245S+N194F+R180*+G183*; F245S+N194F+S181*+T182*; F245S+N194F+T182*+ G183*; F245S+N194Y+R180*+S181*; F245S+N194Y+ R180*+T182*; F245S+N194Y+R180*+G183*; F245S+ N194Y+S181*+T182*; F245S+N194Y+T182*+G183*; F245S+G475K+S243Q+R180*+S181*; F245T+R180*+ S181*; F245T+R180*+T182*; F245T+R180*+G183*; F245T+S181*+T182*; F245T+T182*+G183*; F245T+ N194F+R180*+S181*; F245T+N194F+R180*+T182*; F245T+N194F+R180*+G183*; F245T+N194F+S181*+ T182*; F245T+N194F+T182*+G183*; F245T+N194Y+ R180*+S181*; F245T+N194Y+R180*+T182*; F245T+ N194Y+R180*+G183*; F245T+N194Y+S181*+T182*; F245T+N194Y+T182*+G183*; F245T+G475K+S243Q+ R180*+S181*; F245V+R180*+S181*; F245V+R180*+ T182*; F245V+R180*+G183*; F245V+S181*+T182*; F245V+T182*+G183*; F245V+N194F+R180*+S181*; F245V+N194F+R180*+T182*; F245V+N194F+R180*+ G183*; F245V+N194F+S181*+T182*; F245V+N194F+ T182*+G183*; F245V+N194Y+R180*+S181*; F245V+ N194Y+R180*+T182*; F245V+N194Y+R180*+G183*; F245V+N194Y+S181*+T182*; F245V+N194Y+T182*+ G183*; F245V+G475K+S243Q+R180*+S181*; F245Y+ R180*+S181*; F245Y+R180*+T182*; F245Y+R180*+ G183*; F245Y+S181*+T182*; F245Y+T182*+G183*; F245Y+N194F+R180*+S181*; F245Y+N194F+R180*+ T182*; F245Y+N194F+R180*+G183*; F245Y+N194F+ S181*+T182*; F245Y+N194F+T182*+G183*; F245Y+ N194Y+R180*+S181*; F245Y+N194Y+R180*+T182*; F245Y+N194Y+R180*+G183*; F245Y+N194Y+S181*+ T182*; F245Y+N194Y+T182*+G183*; F245Y+G475K+ S243Q+R180*+S181*; F266Y+R180*+S181*; F266Y+ R180*+T182*; F266Y+R180*+G183*; F266Y+S181*+ T182*; F266Y+T182*+G183*; F266Y+N194F+R180*+ S181*; F266Y+N194F+R180*+T182*; F266Y+N194F+ R180*+G183*; F266Y+N194F+S181*+T182*; F266Y+ N194F+T182*+G183*; F266Y+N194Y+R180*+S181*; F266Y+N194Y+R180*+T182*; F266Y+N194Y+R180*+ G183*; F266Y+N194Y+S181*+T182*; F266Y+N194Y+ T182*+G183*; F266Y+G475K+S243Q+R180*+S181*; Y269N+R180*+S181*; Y269N+R180*+T182*; Y269N+ R180*+G183*; Y269N+S181*+T182*; Y269N+T182*+ G183*; Y269N+N194F+R180*+S181*; Y269N+N194F+ R180*+T182*; Y269N+N194F+R180*+G183*; Y269N+ N194F+S181*+T182*; Y269N+N194F+T182*+G183*; Y269N+N194Y+R180*+S181*; Y269N+N194Y+R180*+ T182*; Y269N+N194Y+R180*+G183*; Y269N+N194Y+ S181*+T182*; Y269N+N194Y+T182*+G183*; Y269N+ G475K+S243Q+R180*+S181*; K280R+R180*+S181*; K280R+R180*+T182*; K280R+R180*+G183*; K280R+ S181*+T182*; K280R+T182*+G183*; K280R+N194F+ R180*+S181*; K280R+N194F+R180*+T182*; K280R+ N194F+R180*+G183*; K280R+N194F+S181*+T182*; K280R+N194F+T182*+G183*; K280R+N194Y+R180*+ S181*; K280R+N194Y+R180*+T182*; K280R+N194Y+ R180*+G183*; K280R+N194Y+S181*+T182*; K280R+ N194Y+T182*+G183*; K280R+G475K+S243Q+R180*+ S181*; G283S+R180*+S181*; G283S+R180*+T182*; G283S+R180*+G183*; G283S+S181*+T182*; G283S+ T182*+G183*; G283S+N194F+R180*+S181*; G283S+ N194F+R180*+T182*; G283S+N194F+R180*+G183*; G283S+N194F+S181*+T182*; G283S+N194F+T182*+ G183*; G283S+N194Y+R180*+S181*; G283S+N194Y+ R180*+T182*; G283S+N194Y+R180*+G183*; G283S+ N194Y+S181*+T182*; G283S+N194Y+T182*+G183*; G283S+G475K+S243Q+R180*+S181*; M285F+R180*+ S181*; M285F+R180*+T182*; M285F+R180*+G183*; M285F+S181*+T182*; M285F+T182*+G183*; M285F+ N194F+R180*+S181*; M285F+N194F+R180*+T182*; M285F+N194F+R180*+G183*; M285F+N194F+S181*+ T182*; M285F+N194F+T182*+G183*; M285F+N194Y+ R180*+S181*; M285F+N194Y+R180*+T182*; M285F+ N194Y+R180*+G183*; M285F+N194Y+S181*+T182*; M285F+N194Y+T182*+G183*; M285F+G475K+S243Q+ R180*+S181*; M285H+R180*+S181*; M285H+R180*+ T182*; M285H+R180*+G183*; M285H+S181*+T182*; M285H+T182*+G183*; M285H+N194F+R180*+S181*; M285H+N194F+R180*+T182*; M285H+N194F+R180*+ G183*; M285H+N194F+S181*+T182*; M285H+N194F+ T182*+G183*; M285H+N194Y+R180*+S181*; M285H+ N194Y+R180*+T182*; M285H+N194Y+R180*+G183*; M285H+N194Y+S181*+T182*; M285H+N194Y+T182*+ G183*; M285H+G475K+S243Q+R180*+S181*; N294Y+ R180*+S181*; N294Y+R180*+T182*; N294Y+R180*+ G183*; N294Y+S181*+T182*; N294Y+T182*+G183*; N294Y+N194F+R180*+S181*; N294Y+N194F+R180*+ T182*; N294Y+N194F+R180*+G183*; N294Y+N194F+ S181*+T182*; N294Y+N194F+T182*+G183*; N294Y+ N194Y+R180*+S181*; N294Y+N194Y+R180*+T182*; N294Y+N194Y+R180*+G183*; N294Y+N194Y+S181*+ T182*; N294Y+N194Y+T182*+G183*; N294Y+G475K+ S243Q+R180*+S181*; M317F+R180*+S181*; M317F+

R180*+T182*; M317F+R180*+G183*; M317F+S181*+ T182*; M317F+T182*+G183*; M317F+N194F+R180*+ S181*; M317F+N194F+R180*+T182*; M317F+N194F+ R180*+G183*; M317F+N194F+S181*+T182*; M317F+ N194F+T182*+G183*; M317F+N194Y+R180*+S181*; M317F+N194Y+R180*+T182*; M317F+N194Y+R180*+ G183*; M317F+N194Y+S181*+T182*; M317F+N194Y+ T182*+G183*; M317F+G475K+S243Q+R180*+S181*; M317I+R180*+S181*; M317I+R180*+T182*; M317I+ R180*+G183*; M317I+S181*+T182*; M317I+T182*+ G183*; M317I+N194F+R180*+S181*; M317I+N194F+ R180*+T182*; M317I+N194F+R180*+G183*; M317I+ N194F+S181*+T182*; M317I+N194F+T182*+G183*; M317I+N194Y+R180*+S181*; M317I+N194Y+R180*+ T182*; M317I+N194Y+R180*+G183*; M317I+N194Y+ S181*+T182*; M317I+N194Y+T182*+G183*; M317I+ G475K+S243Q+R180*+S181*; M317L+R180*+S181*; M317L+R180*+T182*; M317L+R180*+G183*; M317L+ S181*+T182*; M317L+T182*+G183*; M317L+N194F+ R180*+S181*; M317L+N194F+R180*+T182*; M317L+ N194F+R180*+G183*; M317L+N194F+S181*+T182*; M317L+N194F+T182*+G183*; M317L+N194Y+R180*+ S181*; M317L+N194Y+R180*+T182*; M317L+N194Y+ R180*+G183*; M317L+N194Y+S181*+T182*; M317L+ N194Y+T182*+G183*; M317L+G475K+S243Q+R180*+ S181*; M317V+R180*+S181*; M317V+R180*+T182*; M317V+R180*+G183*; M317V+S181*+T182*; M317V+ T182*+G183*; M317V+N194F+R180*+S181*; M317V+ N194F+R180*+T182*; M317V+N194F+R180*+G183*; M317V+N194F+S181*+T182*; M317V+N194F+T182*+ G183*; M317V+N194Y+R180*+S181*; M317V+N194Y+ R180*+T182*; M317V+N194Y+R180*+G183*; M317V+ N194Y+S181*+T182*; M317V+N194Y+T182*+G183*; M317V+G475K+S243Q+R180*+S181*; M317Y+R180*+ S181*; M317Y+R180*+T182*; M317Y+R180*+G183*; M317Y+S181*+T182*; M317Y+T182*+G183*; M317Y+ N194F+R180*+S181*; M317Y+N194F+R180*+T182*; M317Y+N194F+R180*+G183*; M317Y+N194F+S181*+ T182*; M317Y+N194F+T182*+G183*; M317Y+N194Y+ R180*+S181*; M317Y+N194Y+R180*+T182*; M317Y+ N194Y+R180*+G183*; M317Y+N194Y+S181*+T182*; M317Y+N194Y+T182*+G183*;M317Y+G475K+S243Q+ R180*+S181*; L323H+R180*+S181*; L323H+R180*+ T182*; L323H+R180*+G183*; L323H+S181*+T182*; L323H+T182*+G183*; L323H+N194F+R180*+S181*; L323H+N194F+R180*+T182*; L323H+N194F+R180*+ G183*; L323H+N194F+S181*+T182*; L323H+N194F+ T182*+G183*; L323H+N194Y+R180*+S181*; L323H+ N194Y+R180*+T182*; L323H+N194Y+R180*+G183*; L323H+N194Y+S181*+T182*; L323H+N194Y+T182*+ G183*; L323H+G475K+S243Q+R180*+S181*; K375Q+ R180*+S181*; K375Q+R180*+T182*; K375Q+R180*+ G183*; K375Q+S181*+T182*; K375Q+T182*+G183*; K375Q+N194F+R180*+S181*; K375Q+N194F+R180*+ T182*; K375Q+N194F+R180*+G183*; K375Q+N194F+ S181*+T182*; K375Q+N194F+T182*+G183*; K375Q+ N194Y+R180*+S181*; K375Q+N194Y+R180*+T182*; K375Q+N194Y+R180*+G183*; K375Q+N194Y+S181*+ T182*; K375Q+N194Y+T182*+G183*; K375Q+G475K+ S243Q+R180*+S181*; I390E+R180*+S181*; I390E+ R180*+T182*; I390E+R180*+G183*; I390E+S181*+ T182*; I390E+T182*+G183*; I390E+N194F+R180*+ S181*; I390E+N194F+R180*+T182*; I390E+N194F+ R180*+G183*; I390E+N194F+S181*+T182*; I390E+ N194F+T182*+G183*; I390E+N194Y+R180*+S181*; I390E+N194Y+R180*+T182*; I390E+N194Y+R180*+ G183*; I390E+N194Y+S181*+T182*; I390E+N194Y+ T182*+G183*; I390E+G475K+S243Q+R180*+S181*; I390D+R180*+S181*; I390D+R180*+T182*; I390D+ R180*+G183*; I390D+S181*+T182*; I390D+T182*+ G183*; I390D+N194F+R180*+S181*; I390D+N194F+ R180*+T182*; I390D+N194F+R180*+G183*; I390D+ N194F+S181*+T182*; I390D+N194F+T182*+G183*; I390D+N194Y+R180*+S181*; I390D+N194Y+R180*+ T182*; I390D+N194Y+R180*+G183*; I390D+N194Y+ S181*+T182*; I390D+N194Y+T182*+G183*; I390D+ G475K+S243Q+R180*+S181*; I390Q+R180*+S181*; I390Q+R180*+T182*; I390Q+R180*+G183*; I390Q+ S181*+T182*; I390Q+T182*+G183*; I390Q+N194F+ R180*+S181*; I390Q+N194F+R180*+T182*; I390Q+ N194F+R180*+G183*; I390Q+N194F+S181*+T182*; I390Q+N194F+T182*+G183*; I390Q+N194Y+R180*+ S181*; I390Q+N194Y+R180*+T182*; I390Q+N194Y+ R180*+G183*; I390Q+N194Y+S181*+T182*; I390Q+ N194Y+T182*+G183*; I390Q+G475K+S243Q+R180*+ S181*; I390N+R180*+S181*; I390N+R180*+T182*; I390N+R180*+G183*; I390N+S181*+T182*; I390N+ T182*+G183*; I390N+N194F+R180*+S181*; I390N+ N194F+R180*+T182*; I390N+N194F+R180*+G183*; I390N+N194F+S181*+T182*; I390N+N194F+T182*+ G183*; I390N+N194Y+R180*+S181*; I390N+N194Y+ R180*+T182*; I390N+N194Y+R180*+G183*; I390N+ N194Y+S181*+T182*; I390N+N194Y+T182*+G183*; I390N+G475K+S243Q+R180*+S181*; I404F+R180*+ S181*; I404F+R180*+T182*; I404F+R180*+G183*; I404F+S181*+T182*; I404F+T182*+G183*; I404F+ N194F+R180*+S181*; I404F+N194F+R180*+T182*; I404F+N194F+R180*+G183*; I404F+N194F+S181*+ T182*; I404F+N194F+T182*+G183*; I404F+N194Y+ R180*+S181*; I404F+N194Y+R180*+T182*; I404F+ N194Y+R180*+G183*; I404F+N194Y+S181*+T182*; I404F+N194Y+T182*+G183*; I404F+G475K+S243Q+ R180*+S181*; I404L+R180*+S181*; I404L+R180*+ T182*; I404L+R180*+G183*; I404L+S181*+T182*; I404L+T182*+G183*; I404L+N194F+R180*+S181*; I404L+N194F+R180*+T182*; I404L+N194F+R180*+ G183*; I404L+N194F+S181*+T182*; I404L+N194F+ T182*+G183*; I404L+N194Y+R180*+S181*; I404L+ N194Y+R180*+T182*; I404L+N194Y+R180*+G183*; I404L+N194Y+S181*+T182*; I404L+N194Y+T182*+ G183*; I404L+G475K+S243Q+R180*+S181*; I404Y+ R180*+S181*; I404Y+R180*+T182*; I404Y+R180*+ G183*; I404Y+S181*+T182*; I404Y+T182*+G183*; I404Y+N194F+R180*+S181*; I404Y+N194F+R180*+ T182*; I404Y+N194F+R180*+G183*; I404Y+N194F+ S181*+T182*; I404Y+N194F+T182*+G183*; I404Y+ N194Y+R180*+S181*; I404Y+N194Y+R180*+T182*; I404Y+N194Y+R180*+G183*; I404Y+N194Y+S181*+ T182*; I404Y+N194Y+T182*+G183*; I404Y+G475K+ S243Q+R180*+S181*; Q407H+R180*+S181*; Q407H+ R180*+T182*; Q407H+R180*+G183*; Q407H+S181*+ T182*; Q407H+T182*+G183*; Q407H+N194F+R180*+ S181*; Q407H+N194F+R180*+T182*; Q407H+N194F+ R180*+G183*; Q407H+N194F+S181*+T182*; Q407H+ N194F+T182*+G183*; Q407H+N194Y+R180*+S181*; Q407H+N194Y+R180*+T182*; Q407H+N194Y+R180*+ G183*; Q407H+N194Y+S181*+T182*; Q407H+N194Y+ T182*+G183*; Q407H+G475K+S243Q+R180*+S181*; N194F+L205Y+R180*+S181*; N194F+L205Y+R180*+ T182*; N194F+L205Y+R180*+G183*; N194F+L205Y+ S181*+T182*; N194F+L205Y+T182*+G183*; N194F+ L205Y+G475K+S243Q+R180*+S181*; N194F+L205F+ R180*+S181*; N194F+L205F+R180*+T182*; N194F+ L205F+R180*+G183*; N194F+L205F+S181*+T182*;

N194F+L205F+T182*+G183*; N194F+L205F+G475K+ S243Q+R180*+S181*; N194Y+L205Y+R180*+S181*; N194Y+L205Y+R180*+T182*; N194Y+L205Y+R180*+ G183*; N194Y+L205Y+S181*+T182*; N194Y+L205Y+ T182*+G183*; N194Y+L205Y+G475K+S243Q+R180*+ S181*; N194Y+L205F+R180*+S181*; N194Y+L205F+ R180*+T182*; N194Y+L205F+R180*+G183*; N194Y+ L205F+S181*+T182*; N194Y+L205F+T182*+G183*; N194Y+L205F+G475K+S243Q+R180*+S181*; R309Q+ N174NQ+R180*+S181*; R309Q+N174NQ+R180*+ T182*; R309Q+N174NQ+R180*+G183*; R309Q+ N174NQ+S181*+T182*; R309Q+N174NQ+T182*+ G183*; R309Q+N174NQ+N194F+R180*+S181*; R309Q+ N174NQ+N194F+R180*+T182*; R309Q+N174NQ+ N194F+R180*+G183*; R309Q+N174NQ+N194F+S181*+ T182*; R309Q+N174NQ+N194F+T182*+G183*; R309Q+ N174NQ+N194Y+R180*+S181*; R309Q+N174NQ+ N194Y+R180*+T182*; R309Q+N174NQ+N194Y+ R180*+G183*; R309Q+N174NQ+N194Y+S181*+T182*; R309Q+N174NQ+N194Y+T182*+G183*; R309Q+ N174NQ+G475K+S243Q+R180*+S181*; Y48W+ N174NQ+R180*+S181*; Y48W+N174NQ+R180*+T182*; Y48W+N174NQ+R180*+G183*; Y48W+N174NQ+ S181*+T182*; Y48W+N174NQ+T182*+G183*; Y48W+ N174NQ+N194F+R180*+S181*; Y48W+N174NQ+ N194F+R180*+T182*; Y48W+N174NQ+N194F+R180*+ G183*; Y48W+N174NQ+N194F+S181*+T182*; Y48W+ N174NQ+N194F+T182*+G183*; Y48W+N174NQ+ N194Y+R180*+S181*; Y48W+N174NQ+N194Y+R180*+ T182*; Y48W+N174NQ+N194Y+R180*+G183*; Y48W+ N174NQ+N194Y+S181*+T182*; Y48W+N174NQ+ N194Y+T182*+G183*; Y48W+N174NQ+G475K+ S243Q+R180*+S181*; V212N+N174NN+R180*+S181*; V212N+N174NN+R180*+T182*; V212N+N174NN+ R180*+G183*; V212N+N174NN+S181*+T182*; V212N+ N174NN+T182*+G183*; V212N+N174NN+N194F+ R180*+S181*; V212N+N174NN+N194F+R180*+T182*; V212N+N174NN+N194F+R180*+G183*; V212N+ N174NN+N194F+S181*+T182*; V212N+N174NN+ N194F+T182*+G183*; V212N+N174NN+N194Y+ R180*+S181*; V212N+N174NN+N194Y+R180*+T182*; V212N+N174NN+N194Y+R180*+G183*; V212N+ N174NN+N194Y+S181*+T182*; V212N+N174NN+ N194Y+T182*+G183*; V212N+N174NN+G475K+ S243Q+R180*+S181*; V212N+V213Q+R180*+S181*; V212N+V213Q+R180*+T182*; V212N+V213Q+R180*+ G183*; V212N+V213Q+S181*+T182*; V212N+V213Q+ T182*+G183*; V212N+V213Q+N194F+R180*+S181*; V212N+V213Q+N194F+R180*+T182*; V212N+V213Q+ N194F+R180*+G183*; V212N+V213Q+N194F+S181*+ T182*; V212N+V213Q+N194F+T182*+G183*; V212N+ V213Q+N194Y+R180*+S181*; V212N+V213Q+N194Y+ R180*+T182*; V212N+V213Q+N194Y+R180*+G183*; V212N+V213Q+N194Y+S181*+T182*; V212N+V213Q+ N194Y+T182*+G183*; V212N+V213Q+G475K+S243Q+ R180*+S181*; V212P+N174NQ+R180*+S181*; V212P+ N174NQ+R180*+T182*; V212P+N174NQ+R180*+ G183*; V212P+N174NQ+S181*+T182*; V212P+ N174NQ+T182*+G183*; V212P+N174NQ+N194F+ R180*+S181*; V212P+N174NQ+N194F+R180*+T182*; V212P+N174NQ+N194F+R180*+G183*; V212P+ N174NQ+N194F+S181*+T182*; V212P+N174NQ+ N194F+T182*+G183*; V212P+N174NQ+N194Y+R180*+ S181*; V212P+N174NQ+N194Y+R180*+T182*; V212P+ N174NQ+N194Y+R180*+G183*; V212P+N174NQ+ N194Y+S181*+T182*; V212P+N174NQ+N194Y+T182*+ G183*; V212P+N174NQ+G475K+S243Q+R180*+S181*; D16Y+K375Q+R180*+S181*; D16Y+K375Q+R180*+ T182*; D16Y+K375Q+R180*+G183*; D16Y+K375Q+ S181*+T182*; D16Y+K375Q+T182*+G183*; D16Y+ K375Q+N194F+R180*+S181*; D16Y+K375Q+N194F+ R180*+T182*; D16Y+K375Q+N194F+R180*+G183*; D16Y+K375Q+N194F+S181*+T182*; D16Y+K375Q+ N194F+T182*+G183*; D16Y+K375Q+N194Y+R180*+ S181*; D16Y+K375Q+N194Y+R180*+T182*; D16Y+ K375Q+N194Y+R180*+G183*; D16Y+K375Q+N194Y+ S181*+T182*; D16Y+K375Q+N194Y+T182*+G183*; D16Y+K375Q+G475K+S243Q+R180*+S181*; N19D+ Q53R+R180*+S181*; N19D+Q53R+R180*+T182*; N19D+Q53R+R180*+G183*; N19D+Q53R+S181*+ T182*; N19D+Q53R+T182*+G183*; N19D+Q53R+ N194F+R180*+S181*; N19D+Q53R+N194F+R180*+ T182*; N19D+Q53R+N194F+R180*+G183*; N19D+ Q53R+N194F+S181*+T182*; N19D+Q53R+N194F+ T182*+G183*; N19D+Q53R+N194Y+R180*+S181*; N19D+Q53R+N194Y+R180*+T182*; N19D+Q53R+ N194Y+R180*+G183*; N19D+Q53R+N194Y+S181*+ T182*; N19D+Q53R+N194Y+T182*+G183*; N19D+ Q53R+G475K+S243Q+R180*+S181*; Y48W+V60A+ R180*+S181*; Y48W+V60A+R180*+T182*; Y48W+ V60A+R180*+G183*; Y48W+V60A+S181*+T182*; Y48W+V60A+T182*+G183*; Y48W+V60A+N194F+ R180*+S181*; Y48W+V60A+N194F+R180*+T182*; Y48W+V60A+N194F+R180*+G183*; Y48W+V60A+ N194F+S181*+T182*; Y48W+V60A+N194F+T182*+ G183*; Y48W+V60A+N194Y+R180*+S181*; Y48W+ V60A+N194Y+R180*+T182*; Y48W+V60A+N194Y+ R180*+G183*; Y48W+V60A+N194Y+S181*+T182*; Y48W+V60A+N194Y+T182*+G183*; Y48W+V60A+ G475K+S243Q+R180*+S181*; Y48W+F105M+R180*+ S181*; Y48W+F105M+R180*+T182*; Y48W+F105M+ R180*+G183*; Y48W+F105M+S181*+T182*; Y48W+ F105M+T182*+G183*; Y48W+F105M+N194F+R180*+ S181*; Y48W+F105M+N194F+R180*+T182*; Y48W+ F105M+N194F+R180*+G183*; Y48W+F105M+N194F+ S181*+T182*; Y48W+F105M+N194F+T182*+G183*; Y48W+F105M+N194Y+R180*+S181*; Y48W+F105M+ N194Y+R180*+T182*; Y48W+F105M+N194Y+R180*+ G183*; Y48W+F105M+N194Y+S181*+T182*; Y48W+ F105M+N194Y+T182*+G183*; Y48W+F105M+G475K+ S243Q+R180*+S181*; Y48W+L205Y+R180*+S181*; Y48W+L205Y+R180*+T182*; Y48W+L205Y+R180*+ G183*; Y48W+L205Y+S181*+T182*; Y48W+L205Y+ T182*+G183*; Y48W+L205Y+N194F+R180*+S181*; Y48W+L205Y+N194F+R180*+T182*; Y48W+L205Y+ N194F+R180*+G183*; Y48W+L205Y+N194F+S181*+ T182*; Y48W+L205Y+N194F+T182*+G183*; Y48W+ L205Y+N194Y+R180*+S181*; Y48W+L205Y+N194Y+ R180*+T182*; Y48W+L205Y+N194Y+R180*+G183*; Y48W+L205Y+N194Y+S181*+T182*; Y48W+L205Y+ N194Y+T182*+G183*; Y48W+L205Y+G475K+S243Q+ R180*+S181*; V60A+L205Y+R180*+S181*; V60A+ L205Y+R180*+T182*; V60A+L205Y+R180*+G183*; V60A+L205Y+S181*+T182*; V60A+L205Y+T182*+ G183*; V60A+L205Y+N194F+R180*+S181*; V60A+ L205Y+N194F+R180*+T182*; V60A+L205Y+N194F+ R180*+G183*; V60A+L205Y+N194F+S181*+T182*; V60A+L205Y+N194F+T182*+G183*; V60A+L205Y+ N194Y+R180*+S181*; V60A+L205Y+N194Y+R180*+ T182*; V60A+L205Y+N194Y+R180*+G183*; V60A+ L205Y+N194Y+S181*+T182*; V60A+L205Y+N194Y+ T182*+G183*; V60A+L205Y+G475K+S243Q+R180*+ S181*; Y48W+V60A+F105M+R180*+S181*; Y48W+ V60A+F105M+R180*+T182*; Y48W+V60A+F105M+

R180*+G183*; Y48W+V60A+F105M+S181*+T182*; Y48W+V60A+F105M+T182*+G183*; Y48W+V60A+F105M+N194F+R180*+S181*; Y48W+V60A+F105M+N194F+R180*+T182*; Y48W+V60A+F105M+N194F+R180*+G183*; Y48W+V60A+F105M+N194F+S181*+T182*; Y48W+V60A+F105M+N194F+T182*+G183*; Y48W+V60A+F105M+N194Y+R180*+S181*; Y48W+V60A+F105M+N194Y+R180*+T182*; Y48W+V60A+F105M+N194Y+R180*+G183*; Y48W+V60A+F105M+N194Y+S181*+T182*; Y48W+V60A+F105M+N194Y+T182*+G183*; Y48W+V60A+F105M+G475K+S243Q+R180*+S181*; Y48W+V60A+L205F+R180*+S181*; Y48W+V60A+L205F+R180*+T182*; Y48W+V60A+L205F+R180*+G183*; Y48W+V60A+L205F+S181*+T182*; Y48W+V60A+L205F+T182*+G183*; Y48W+V60A+L205F+N194F+R180*+S181*; Y48W+V60A+L205F+N194F+R180*+T182*; Y48W+V60A+L205F+N194F+R180*+G183*; Y48W+V60A+L205F+N194F+S181*+T182*; Y48W+V60A+L205F+N194F+T182*+G183*; Y48W+V60A+L205F+N194Y+R180*+S181*; Y48W+V60A+L205F+N194Y+R180*+T182*; Y48W+V60A+L205F+N194Y+R180*+G183*; Y48W+V60A+L205F+N194Y+S181*+T182*; Y48W+V60A+L205F+N194Y+T182*+G183*; Y48W+V60A+L205F+G475K+S243Q+R180*+S181*; V60A+F105M+L205F+R180*+S181*; V60A+F105M+L205F+R180*+T182*; V60A+F105M+L205F+R180*+G183*; V60A+F105M+L205F+S181*+T182*; V60A+F105M+L205F+T182*+G183*; V60A+F105M+L205F+N194F+R180*+S181*; V60A+F105M+L205F+N194F+R180*+T182*; V60A+F105M+L205F+N194F+R180*+G183*; V60A+F105M+L205F+N194F+S181*+T182*; V60A+F105M+L205F+N194F+T182*+G183*; V60A+F105M+L205F+N194Y+R180*+S181*; V60A+F105M+L205F+N194Y+R180*+T182*; V60A+F105M+L205F+N194Y+R180*+G183*; V60A+F105M+L205F+N194Y+S181*+T182*; V60A+F105M+L205F+N194Y+T182*+G183*; V60A+F105M+L205F+G475K+S243Q+R180*+S181*; Y48W+V60A+F105M+L205F+R180*+S181*; Y48W+V60A+F105M+L205F+R180*+T182*; Y48W+V60A+F105M+L205F+R180*+G183*; Y48W+V60A+F105M+L205F+S181*+T182*; Y48W+V60A+F105M+L205F+T182*+G183*; Y48W+V60A+F105M+L205F+N194F+R180*+S181*; Y48W+V60A+F105M+L205F+N194F+R180*+T182*; Y48W+V60A+F105M+L205F+N194F+R180*+G183*; Y48W+V60A+F105M+L205F+N194F+S181*+T182*; Y48W+V60A+F105M+L205F+N194F+T182*+G183*; Y48W+V60A+F105M+L205F+N194Y+R180*+S181*; Y48W+V60A+F105M+L205F+N194Y+R180*+T182*; Y48W+V60A+F105M+L205F+N194Y+R180*+G183*; Y48W+V60A+F105M+L205F+N194Y+S181*+T182*; Y48W+V60A+F105M+L205F+N194Y+T182*+G183*; Y48W+V60A+F105M+L205F+G475K+S243Q+R180*+S181*; Y48W+V60A+L205Y+R180*+S181*; Y48W+V60A+L205Y+R180*+T182*; Y48W+V60A+L205Y+R180*+G183*; Y48W+V60A+L205Y+S181*+T182*; Y48W+V60A+L205Y+T182*+G183*; Y48W+V60A+L205Y+N194F+R180*+S181*; Y48W+V60A+L205Y+N194F+R180*+T182*; Y48W+V60A+L205Y+N194F+R180*+G183*; Y48W+V60A+L205Y+N194F+S181*+T182*; Y48W+V60A+L205Y+N194F+T182*+G183*; Y48W+V60A+L205Y+N194Y+R180*+S181*; Y48W+V60A+L205Y+N194Y+R180*+T182*; Y48W+V60A+L205Y+N194Y+R180*+G183*; Y48W+V60A+L205Y+N194Y+S181*+T182*; Y48W+V60A+L205Y+N194Y+T182*+G183*; Y48W+V60A+L205Y+G475K+S243Q+R180*+S181*; V60A+F105M+L205Y+R180*+S181*; V60A+F105M+L205Y+R180*+T182*; V60A+F105M+L205Y+R180*+G183*; V60A+F105M+L205Y+S181*+T182*; V60A+F105M+L205Y+T182*+G183*; V60A+F105M+L205Y+N194F+R180*+S181*; V60A+F105M+L205Y+N194F+R180*+T182*; V60A+F105M+L205Y+N194F+R180*+G183*; V60A+F105M+L205Y+N194F+S181*+T182*; V60A+F105M+L205Y+N194F+T182*+G183*; V60A+F105M+L205Y+N194Y+R180*+S181*; V60A+F105M+L205Y+N194Y+R180*+T182*; V60A+F105M+L205Y+N194Y+R180*+G183*; V60A+F105M+L205Y+N194Y+S181*+T182*; V60A+F105M+L205Y+N194Y+T182*+G183*; V60A+F105M+L205Y+G475K+S243Q+R180*+S181*; Y48W+V60A+F105M+L205Y+R180*+S181*; Y48W+V60A+F105M+L205Y+R180*+T182*; Y48W+V60A+F105M+L205Y+R180*+G183*; Y48W+V60A+F105M+L205Y+S181*+T182*; Y48W+V60A+F105M+L205Y+T182*+G183*; Y48W+V60A+F105M+L205Y+N194F+R180*+S181*; Y48W+V60A+F105M+L205Y+N194F+R180*+T182*; Y48W+V60A+F105M+L205Y+N194F+R180*+G183*; Y48W+V60A+F105M+L205Y+N194F+S181*+T182*; Y48W+V60A+F105M+L205Y+N194F+T182*+G183*; Y48W+V60A+F105M+L205Y+N194Y+R180*+S181*; Y48W+V60A+F105M+L205Y+N194Y+R180*+T182*; Y48W+V60A+F105M+L205Y+N194Y+R180*+G183*; Y48W+V60A+F105M+L205Y+N194Y+S181*+T182*; Y48W+V60A+F105M+L205Y+N194Y+T182*+G183*; Y48W+V60A+F105M+L205Y+G475K+S243Q+R180*+S181*; P124D+S125P+R180*+S181*; P124D+S125P+R180*+T182*; P124D+S125P+R180*+G183*; P124D+S125P+S181*+T182*; P124D+S125P+T182*+G183*; P124D+S125P+N194F+R180*+S181*; P124D+S125P+N194F+R180*+T182*; P124D+S125P+N194F+R180*+G183*; P124D+S125P+N194F+S181*+T182*; P124D+S125P+N194F+T182*+G183*; P124D+S125P+N194Y+R180*+S181*; P124D+S125P+N194Y+R180*+T182*; P124D+S125P+N194Y+R180*+G183*; P124D+S125P+N194Y+S181*+T182*; P124D+S125P+N194Y+T182*+G183*; P124D+S125P+G475K+S243Q+R180*+S181*; P124D+S125N+R180*+S181*; P124D+S125N+R180*+T182*; P124D+S125N+R180*+G183*; P124D+S125N+S181*+T182*; P124D+S125N+T182*+G183*; P124D+S125N+N194F+R180*+S181*; P124D+S125N+N194F+R180*+T182*; P124D+S125N+N194F+R180*+G183*; P124D+S125N+N194F+S181*+T182*; P124D+S125N+N194F+T182*+G183*; P124D+S125N+N194Y+R180*+S181*; P124D+S125N+N194Y+R180*+T182*; P124D+S125N+N194Y+R180*+G183*; P124D+S125N+N194Y+S181*+T182*; P124D+S125N+N194Y+T182*+G183*; P124D+S125N+G475K+S243Q+R180*+S181*; S125N+N174NN+R180*+S181*; S125N+N174NN+R180*+T182*; S125N+N174NN+R180*+G183*; S125N+N174NN+S181*+T182*; S125N+N174NN+T182*+G183*; S125N+N174NN+N194F+R180*+S181*; S125N+N174NN+N194F+R180*+T182*; S125N+N174NN+N194F+R180*+G183*; S125N+N174NN+N194F+S181*+T182*; S125N+N174NN+N194F+T182*+G183*; S125N+N174NN+N194Y+R180*+S181*; S125N+N174NN+N194Y+R180*+T182*; S125N+N174NN+N194Y+R180*+G183*; S125N+N174NN+N194Y+S181*+T182*; S125N+N174NN+N194Y+T182*+G183*; S125N+N174NN+G475K+S243Q+R180*+S181*; K172Q+N174NQ+R180*+S181*; K172Q+N174NQ+R180*+T182*; K172Q+N174NQ+R180*+G183*; K172Q+N174NQ+S181*+T182*; K172Q+N174NQ+T182*+G183*; K172Q+N174NQ+N194F+R180*+S181*; K172Q+N174NQ+N194F+R180*+T182*; K172Q+N174NQ+N194F+R180*+G183*; K172Q+N174NQ+N194F+S181*+

T182*; K172Q+N174NQ+N194F+T182*+G183*; K172Q+ N174NQ+N194Y+R180*+S181*; K172Q+N174NQ+ N194Y+R180*+T182*; K172Q+N174NQ+N194Y+ R180*+G183*; K172Q+N174NQ+N194Y+S181*+T182*; K172Q+N174NQ+N194Y+T182*+G183*; K172Q+ N174NQ+G475K+S243Q+R180*+S181*; K172Q+L173F+ R180*+S181*; K172Q+L173F+R180*+T182*; K172Q+ L173F+R180*+G183*; K172Q+L173F+S181*+T182*; K172Q+L173F+T182*+G183*; K172Q+L173F+N194F+ R180*+S181*; K172Q+L173F+N194F+R180*+T182*; K172Q+L173F+N194F+R180*+G183*; K172Q+L173F+ N194F+S181*+T182*; K172Q+L173F+N194F+T182*+ G183*; K172Q+L173F+N194Y+R180*+S181*; K172Q+ L173F+N194Y+R180*+T182*; K172Q+L173F+N194Y+ R180*+G183*; K172Q+L173F+N194Y+S181*+T182*; K172Q+L173F+N194Y+T182*+G183*; K172Q+L173F+ G475K+S243Q+R180*+S181*; K172Q+L173F+N174NQ+ R180*+S181*; K172Q+L173F+N174NQ+R180*+T182*; K172Q+L173F+N174NQ+R180*+G183*; K172Q+ L173F+N174NQ+S181*+T182*; K172Q+L173F+ N174NQ+T182*+G183*; K172Q+L173F+N174NQ+ N194F+R180*+S181*; K172Q+L173F+N174NQ+N194F+ R180*+T182*; K172Q+L173F+N174NQ+N194F+R180*+ G183*; K172Q+L173F+N174NQ+N194F+S181*+T182*; K172Q+L173F+N174NQ+N194F+T182*+G183*; K172Q+L173F+N174NQ+N194Y+R180*+S181*; K172Q+L173F+N174NQ+N194Y+R180*+T182*; K172Q+L173F+N174NQ+N194Y+R180*+G183*; K172Q+L173F+N174NQ+N194Y+S181*+T182*; K172Q+L173F+N174NQ+N194Y+T182*+G183*; K172Q+L173F+N174NQ+G475K+S243Q+R180*+S181*; Y242F+F266Y+R180*+S181*; Y242F+F266Y+R180*+ T182*; Y242F+F266Y+R180*+G183*; Y242F+F266Y+ S181*+T182*; Y242F+F266Y+T182*+G183*; Y242F+ F266Y+N194F+R180*+S181*; Y242F+F266Y+N194F+ R180*+T182*; Y242F+F266Y+N194F+R180*+G183*; Y242F+F266Y+N194F+S181*+T182*; Y242F+F266Y+ N194F+T182*+G183*; Y242F+F266Y+N194Y+R180*+ S181*; Y242F+F266Y+N194Y+R180*+T182*; Y242F+ F266Y+N194Y+R180*+G183*; Y242F+F266Y+N194Y+ S181*+T182*; Y242F+F266Y+N194Y+T182*+G183*; Y242F+F266Y+G475K+S243Q+R180*+S181*; Y269N+ N294Y+R180*+S181*; Y269N+N294Y+R180*+T182*; Y269N+N294Y+R180*+G183*; Y269N+N294Y+S181*+ T182*; Y269N+N294Y+T182*+G183*; Y269N+N294Y+ N194F+R180*+S181*; Y269N+N294Y+N194F+R180*+ T182*; Y269N+N294Y+N194F+R180*+G183*; Y269N+ N294Y+N194F+S181*+T182*; Y269N+N294Y+N194F+ T182*+G183*; Y269N+N294Y+N194Y+R180*+S181*; Y269N+N294Y+N194Y+R180*+T182*; Y269N+N294Y+ N194Y+R180*+G183*; Y269N+N294Y+N194Y+S181*+ T182*; Y269N+N294Y+N194Y+T182*+G183*; Y269N+ N294Y+G475K+S243Q+R180*+S181*; G283S+L323H+ R180*+S181*; G283S+L323H+R180*+T182*; G283S+ L323H+R180*+G183*; G283S+L323H+S181*+T182*; G283S+L323H+T182*+G183*; G283S+L323H+N194F+ R180*+S181*; G283S+L323H+N194F+R180*+T182*; G283S+L323H+N194F+R180*+G183*; G283S+L323H+ N194F+S181*+T182*; G283S+L323H+N194F+T182*+ G183*; G283S+L323H+N194Y+R180*+S181*; G283S+ L323H+N194Y+R180*+T182*; G283S+L323H+N194Y+ R180*+G183*; G283S+L323H+N194Y+S181*+T182*; G283S+L323H+N194Y+T182*+G183*; G283S+L323H+ G475K+S243Q+R180*+S181*, wherein the variant has at least 80% and less than 100% sequence identity to the alpha-amylase of SEQ ID NO: 2.

In one embodiment, the variant has at least 80% sequence identity to the amino acid sequence of SEQ ID NO: 1.

In another embodiment, the variant has at least 85% sequence identity to the amino acid sequence of SEQ ID NO: 1.

In another embodiment, the variant has at least 90% sequence identity to the amino acid sequence of SEQ ID NO: 1.

In another embodiment, the variant has at least 91% sequence identity to the amino acid sequence of SEQ ID NO: 1.

In another embodiment, the variant has at least 92% sequence identity to the amino acid sequence of SEQ ID NO: 1.

In another embodiment, the variant has at least 93% sequence identity to the amino acid sequence of SEQ ID NO: 1.

In another embodiment, the variant has at least 94% sequence identity to the amino acid sequence of SEQ ID NO: 1.

In another embodiment, the variant has at least 95% sequence identity to the amino acid sequence of SEQ ID NO: 1.

In another embodiment, the variant has at least 96% sequence identity to the amino acid sequence of SEQ ID NO: 1.

In another embodiment, the variant has at least 97% sequence identity to the amino acid sequence of SEQ ID NO: 1.

In another embodiment, the variant has at least 98% sequence identity to the amino acid sequence of SEQ ID NO: 1.

In another embodiment, the variant has at least 99% sequence identity to the amino acid sequence of SEQ ID NO: 1.

In one embodiment, the variant has at least 80% sequence identity to the amino acid sequence of SEQ ID NO: 2.

In another embodiment, the variant has at least 85% sequence identity to the amino acid sequence of SEQ ID NO: 2.

In another embodiment, the variant has at least 90% sequence identity to the amino acid sequence of SEQ ID NO: 2.

In another embodiment, the variant has at least 91% sequence identity to the amino acid sequence of SEQ ID NO: 2.

In another embodiment, the variant has at least 92% sequence identity to the amino acid sequence of SEQ ID NO: 2.

In another embodiment, the variant has at least 93% sequence identity to the amino acid sequence of SEQ ID NO: 2.

In another embodiment, the variant has at least 94% sequence identity to the amino acid sequence of SEQ ID NO: 2.

In another embodiment, the variant has at least 95% sequence identity to the amino acid sequence of SEQ ID NO: 2.

In another embodiment, the variant has at least 96% sequence identity to the amino acid sequence of SEQ ID NO: 2.

In another embodiment, the variant has at least 97% sequence identity to the amino acid sequence of SEQ ID NO: 2.

In another embodiment, the variant has at least 98% sequence identity to the amino acid sequence of SEQ ID NO: 2.

In another embodiment, the variant has at least 99% sequence identity to the amino acid sequence of SEQ ID NO: 2.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, improve wash performance and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

In an embodiment, the variant has improved catalytic efficiency compared to the alpha-amylase of SEQ ID NO: 1 or 2.

In an embodiment, the variant has improved catalytic rate compared to the alpha-amylase of SEQ ID NO: 1 or 2.

In an embodiment, the variant has improved chemical stability compared to the alpha-amylase of SEQ ID NO: 1 or 2.

In an embodiment, the variant has improved oxidation stability compared to the alpha-amylase of SEQ ID NO: 1 or 2.

In an embodiment, the variant has improved detergent stability compared to the alpha-amylase of SEQ ID NO: 1 or 2.

In an embodiment, the variant has improved pH activity compared to the alpha-amylase of SEQ ID NO: 1 or 2.

In an embodiment, the variant has improved pH stability compared to the alpha-amylase of SEQ ID NO: 1 or 2.

In an embodiment, the variant has improved specific activity compared to the alpha-amylase of SEQ ID NO: 1 or 2.

In an embodiment, the variant has improved stability under storage conditions compared to the alpha-amylase of SEQ ID NO: 1 or 2.

In an embodiment, the variant has decreased substrate binding compared to the alpha-amylase of SEQ ID NO: 1 or 2.

In an embodiment, the variant has improved substrate specificity compared to the alpha-amylase of SEQ ID NO: 1 or 2.

In an embodiment, the variant has improved substrate stability compared to the alpha-amylase of SEQ ID NO: 1 or 2.

In an embodiment, the variant has improved surface properties compared to the alpha-amylase of SEQ ID NO: 1 or 2.

In an embodiment, the variant has improved thermal activity compared to the alpha-amylase of SEQ ID NO: 1 or 2.

In an embodiment, the variant has improved thermostability compared to the alpha-amylase of SEQ ID NO: 1 or 2.

In another embodiment the variant has improved wash performance, in particular improved wash performance at low temperature compared to the alpha-amylase of SEQ ID NO: 1 or 2.

Parent Alpha-Amylases

The parent alpha-amylase may be (a) a polypeptide having at least 80% sequence identity to the mature polypeptide of SEQ ID NO: 1; (b) a fragment of the mature polypeptide of SEQ ID NO: 1, which has alpha-amylase activity or (c) a polypeptide having immunological cross reactivity with an antibody raised against the mature polypeptide of SEQ ID NO: 1.

In another aspect, the parent alpha-amylase may be (a) a polypeptide having at least 80% sequence identity to the mature polypeptide of SEQ ID NO: 2; (b) a fragment of the mature polypeptide of SEQ ID NO: 2, which has alpha-amylase activity or (c) a polypeptide having immunological cross reactivity with an antibody raised against the mature polypeptide of SEQ ID NO: 2.

In an aspect, the parent has a sequence identity to the mature polypeptide of SEQ ID NO: 1 of at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by no more than 10 amino acids, e.g., 1, 2, 3, 4, 5, 6, 7, 8, or 9, from the mature polypeptide of SEQ ID NO: 1.

In an aspect, the parent has a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by no more than 10 amino acids, e.g., 1, 2, 3, 4, 5, 6, 7, 8, or 9, from the mature polypeptide of SEQ ID NO: 2.

In an aspect, the parent has a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by no more than 10 amino acids, e.g., 1, 2, 3, 4, 5, 6, 7, 8, or 9, from the mature polypeptide of SEQ ID NO: 3. In an aspect, the parent has a sequence identity to the mature polypeptide of SEQ ID NO: 4 of at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by no more than 10 amino acids, e.g., 1, 2, 3, 4, 5, 6, 7, 8, or 9, from the mature polypeptide of SEQ ID NO: 4 In an aspect, the parent has a sequence identity to the mature polypeptide of SEQ ID NO: 5 of at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by no more than 10 amino acids, e.g., 1, 2, 3, 4, 5, 6, 7, 8, or 9, from the mature polypeptide of SEQ ID NO: 5. In an aspect, the parent has a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by no more than 10 amino acids, e.g., 1, 2, 3, 4, 5, 6, 7, 8, or 9, from the mature polypeptide of SEQ ID NO: 6. In an aspect, the parent has a sequence identity to the mature polypeptide of SEQ ID NO: 7 of at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by no more than 10 amino acids, e.g., 1, 2, 3, 4, 5, 6, 7, 8, or 9, from the mature polypeptide of SEQ ID NO: 7. In an aspect, the parent has a sequence identity to the mature polypeptide of SEQ ID NO: 8 of at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by no more than 10 amino acids, e.g., 1, 2, 3, 4, 5, 6, 7, 8, or 9, from the mature polypeptide of SEQ ID NO:8.

In another aspect, the parent comprises or consists of the amino acid sequence of SEQ ID NO: 1. In another aspect, the parent comprises or consists of the amino acid sequence of SEQ ID NO: 2. In another aspect, the parent comprises or consists of the amino acid sequence of SEQ ID NO: 3. In another aspect, the parent comprises or consists of the amino acid sequence of SEQ ID NO: 4. In another aspect, the parent comprises or consists of the amino acid sequence of SEQ ID NO: 5. In another aspect, the parent comprises or consists of the amino acid sequence of SEQ ID NO: 6. In another aspect, the parent comprises or consists of the amino acid sequence of SEQ ID NO: 7. In another aspect, the parent comprises or consists of the amino acid sequence of SEQ ID NO: 8.

In yet another embodiment, the parent is an allelic variant of the mature polypeptide of SEQ ID NO: 1 or 2.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial alpha-amylase. For example, the parent may be a Gram-positive bacterial polypeptide such as a *Bacillus* alpha-amylase.

In one aspect, the parent is a *Bacillus* sp. TS-23 alpha-amylase e.g., the alpha-amylase of SEQ ID NO: 1 or 2.

The alpha-amylases of SEQ ID NOs 1 and 2 as well as the variants hereof may be artificially manufactured by methods known in the art.

Preparation of Variants

The present invention also relates to methods for obtaining a variant having alpha-amylase activity, comprising introducing into a parent alpha-amylase having at least 80% sequence identity to SEQ ID NO: 1 or 2 a) a deletion at two or more positions corresponding to positions R180, S181, T182 and G183 of the mature polypeptide of SEQ ID NO: 1 or 2 and b) an alteration at one or more positions corresponding to positions Y48, E169, S170, R171, K172, L173, N174, L205, R309, M317, I390, D16, N19, Q53, V60, F105, F116, P124, S125, N128, T131, G133, K178, A185, E189, N194, A203, M208, H209, E211, V212, V213, K241, Y242, F245, F266, Y269, K280, G283, M285, N294, L323, K375, I404 and Q407 of the mature polypeptide of SEQ ID NO: 1 or 2, wherein each alteration is independently a substitution or an insertion, wherein the variant has at least 80%, such as at least 90%, but less than 100% sequence identity with the mature polypeptide of SEQ ID NO: 1 or 2, wherein the variant has alpha-amylase activity; and recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-alpha-amylase gene (amyQ), *Bacillus licheniformis* alpha-alpha-amylase gene (amyL), *Bacillus licheniformis* penicillinase gene (penP), *Bacillus stearothermophilus* maltogenic alpha-amylase gene (amyM), *Bacillus subtilis* levansucrase gene (sacB), *Bacillus subtilis* xylA and xylB genes, *Bacillus thuringiensis* ctyIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-alpha-amylase, *Aspergillus niger* acid stable alpha-alpha-amylase, *Aspergillus niger* or *Aspergillus awamori* glucoalpha-amylase (glaA), *Aspergillus oryzae* TAKA alpha-amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-alpha-amylase gene in which the untranslated leader has been replaced by an untranslated leader from an *Aspergillus* triose phosphate isomerase gene; non-limiting examples include modified promoters from an *Aspergillus niger* neutral alpha-alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP),

*Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoalpha-amylase, *Aspergillus niger* alpha-glucosidase, *Aspergillus oryzae* TAKA alpha-amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA alpha-amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoalpha-amylase, *Aspergillus niger* alpha-glucosidase, *Aspergillus oryzae* TAKA alpha-amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic alpha-amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral alpha-amylase, *Aspergillus niger* glucoalpha-amylase, *Aspergillus oryzae* TAKA alpha-amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoalpha-amylase promoter, *Aspergillus oryzae* TAKA alpha-alpha-amylase promoter, and *Aspergillus oryzae* glucoalpha-amylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The alpha-amylase variants of the present invention may be expressed as described in WO2010/115021.

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell, including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No. 9*, 1980).

The yeast host cell may be a *Candida*, *Hansenula*, *Kluyveromyces*, *Pichia*, *Saccharomyces*, *Schizosaccharomyces*, or *Yarrowia* cell such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonaturn*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenaturn*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*,

*Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

The host cell may be a plant cell comprising a polynucleotide of the present invention so as to express and produce the variant in recoverable quantities. Such transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn). Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell. The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The present invention also relates to compositions comprising a variant of the present invention. Preferably, the compositions are enriched in such a variant. The term "enriched" means that the alpha-amylase activity of the composition has been increased, e.g., with an enrichment factor of 1.1.

The composition may comprise a variant as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger*, or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulaturn, Fusarium roseum, Fusarium sambucinum, Fusarium sarcochroum, Fusarium sulphureum, Fusarium toruloseum, Fusarium trichothecioides*, or *Fusarium venenatum; Humicola*, e.g., *Humicola insolens* or *Humicola lanuginosa*; or *Trichoderma*, e.g., *Trichoderma harzianum, Trichoderma koningii, Trichoderma longibrachiatum, Trichoderma reesei*, or *Trichoderma viride*.

The compositions may be prepared in accordance with methods known in the art and may be in the form of a liquid or a dry composition. For instance, the composition may be in the form of a granulate or a microgranulate. The variant may be stabilized in accordance with methods known in the art.

Detergent Compositions

In one embodiment, the invention is directed to detergent compositions comprising an alpha-amylase variant of the present invention in combination with one or more additional cleaning composition components.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Enzyme of the Present Invention

In one embodiment of the present invention, the a polypeptide of the present invention may be added to a detergent composition in an amount corresponding to 0.001-100 mg of protein, such as 0.01-100 mg of protein, preferably 0.01-50 mg of protein, more preferably 0.01-25 mg of protein, even more preferably 0.05-10 mg of protein, most preferably 0.05-5 mg of protein, and even most preferably 0.05-1 mg of protein per liter of wash liquor.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO92/19709 and WO92/19708.

A polypeptide of the present invention may also be incorporated in the detergent formulations disclosed in WO97/07202, which is hereby incorporated by reference.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 0% to about 40% by weight of a cationic surfactant. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 0% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxy ethyl)amine oxide, fatty acid alkanolamides and ethoxylated fatty acid alkanolamides, and combinations thereof.

When included therein the detergent will usually contain from about 0% to about 40% by weight of a zwitterionic surfactant. Non-limiting examples of zwitterionic surfactants include betaine, alkyldimethylbetaine, sulfobetaine, and combinations thereof.

The detergent composition may comprise one or more isoprenoid-based surfactants, such as the ones described in international patent applications WO2013043857 (A1), WO2013043855 (A2), WO2013043852 (A2), WO2013043805 (A1) or WO2013043803 (A2).

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), *Current Opinion in Colloid & Interface Science* 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 10% to about 40% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2"-nitrilotriethanol), and carboxymethyl inulin (CMI), and combinations thereof.

The detergent composition may also contain 0-50% by weight, such as about 10% to about 40%, of a detergent co-builder, or a mixture thereof. The detergent composition may include include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N, N-diacetic acid (α-ALDA), serine-N, N-diacetic acid (SEDA), isoserine-N, N-diacetic acid (ISDA), phenylalanine-N, N-diacetic acid (PHDA), anthranilic acid-N, N-diacetic acid (ANDA), sulfanilic acid-N, N-diacetic acid (SLDA), taurine-N, N-diacetic acid (TUDA) and sulfomethyl-N, N-diacetic acid (SMDA), N-(2-hydroxyethyl)-ethylidenediamine-N, N, N'-triacetate (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

Bleaching Systems

The detergent may contain 0-20% by weight, such as about 0% to about 10%, of a bleaching system. Any bleaching system known in the art for use in laundry+dish wash+I&I detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetylethylene diamine (TAED), sodium 4-[(3,5,5-trimethylhexanoyl)oxy]benzene sulfonate (ISONOBS), diperoxy dodecanoic acid, 4-(dodecanoyloxy)benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like triacetin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

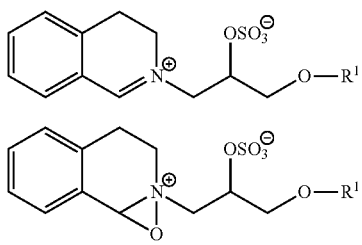

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g. in WO2007/087258, WO2007/087244, WO2007/087259 and WO2007/087242. Suitable photobleaches may for example be sulfonated zinc phthalocyanine.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Additional Enzymes

The detergent additive as well as the detergent composition may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Cellulase

Suitable cellulases include complete cellulases or mono-component endoglucanases of bacterial or fungal origin. Chemically or genetically modified mutants are included. The cellulase may for example be a mono-component or a mixture of mono-component endo-1,4-beta-glucanase often just termed endoglucanases. Suitable cellulases include a fungal cellulase from *Humicola insolens* (U.S. Pat. No. 4,435,307) or from *Trichoderma*, e.g. *T. reesei* or *T. viride*. Examples of cellulases are described in EP 0 495 257. Other suitable cellulases are from *Thielavia* e.g. *Thielavia terrestris* as described in WO 96/29397 or *Fusarium oxysporum* as described in WO 91/17244 or from *Bacillus* as described in, WO 02/099091 and JP 2000210081. Other examples are cellulase variants such as those described in WO 94/07998, EP 0 531 315, U.S. Pat. Nos. 5,457,046, 5,686,593, 5,763,254, WO 95/24471, WO 98/12307 Commercially available cellulases include Carezyme®, Celluzyme®, Celluclean®, Celluclast® and Endolase®; Renozyme®; Whitezyme® (Novozymes A/S) Puradax®, Puradax HA, and Puradax EG (available from Genencor).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin lentus, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellumonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V41, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase® Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases:

Suitable amylases which can be used together with the enzymes of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K
E187P+I203Y+R458N+T459S+D460T+G476K
wherein the variants optionally further comprises a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128 K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I wherein the variants optionally further comprises a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are polyethyleneglycol (PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants—

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent—

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3] triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers—

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents—

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other Suitable Adjunct Materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

Definition/Characteristics of the Forms:

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may also be non-aqueous.

Laundry Soap Bars

The alpha-amylases of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, an alpha-amylase, optionally one or more additional enzymes, a protease inhibitor, and a salt of a monovalent cation and an organic anion may be prepared and and the mixture is then plodded. The alpha-amylase and optional additional enzymes may be added at the same time as the protease inhibitor for example in liquid form. Besides the mixing step and the plodding step, the process may further comprise the steps of milling, extruding, cutting, stamping, cooling and/or wrapping.

Granular Detergent Formulations

A granular detergent may be formulated as described in WO09/092699, EP1705241, EP1382668, WO07/001262, U.S. Pat. No. 6,472,364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, and WO09/015951.

WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905,

WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792,

WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, WO2010000636.

Uses

The present invention is also directed to methods for using the alpha-amylase variants.

The alpha-amylase variants of the invention are useful in detergent compositions, laundry washing, dishwashing and/or cleaning processes at low temperature as well as hard surface cleaning (ADW, car wash, Industrial surface).

Use in Detergents.

The polypeptides of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

The detergent composition may further be formulated in unit dosage form or in form a soap bar or a laundry bar, In a specific aspect, the present invention provides a detergent additive comprising a polypeptide of the present invention as described herein. In another aspect, the present invention provides a detergent suited to cleaning at temperatures at or below 35° C.

Methods

Amylase expression: the alpha-amylase variants of the present invention may be expressed as disclosed in WO2010115021

Strain: eg. *B.subtilis, B.licheniformis*, carring the amylase in an expression cassette either on a plasmid or integrated on the *bacillus* chromosome, eg. in the Pel or Amy locus.

Media: eg, LB, TY, Media-16

Media 16
  Glycerol—5% w/y
  Tryptone—0.5% w/v
  Beef Extract—0.5% w/v
  Sodium Nitrate—1% w/y
  $Na_2HPO_4$—1.7% w/y
  $KH_2PO_4$—0.4% w/y
  $NH_4Cl$—0.1% w/y
  NaCl—0.05% w/v
  Adjust to pH 7 and autoclave.
Autoclaved Separately and Added Just Before Inoculation
  1.47% $CaCl_2$—0.4 ml for 100 ml media
  2.465% $MgSO_4.7H_2O$—0.4 ml for 100 ml media
  1.39% $FeSO_4$—0.04 ml for 100 ml media
  0.2% $Na_2MoO_4.2H_2O$—0.04 ml for 100 ml media
  Vitamin Mix (containing 0.25% Thiamine and 0.25% Ascorbic Acid)—0.4 ml of Vitamin Mix for 100 ml media
  Trace Elements (containing 0.5% $MnCl_2.4H_2O$, 0.2% $ZnCl_2$ and 0.1% $CuSO_4.5H_2O$)—0.04 ml of Trace sol for 100 ml media
Construction of TS23 Variants Synthetic DNA coding for the mature but CBM truncated amylase was purchased from external vendor (Geneart, Germany) and by amplifying the amylase gene by N and C terminal primers (CA509: GCCTCATTCTGCAGCCGCG-GCAGCTAATACTGCACCTATTAACG and CA508: GAGCGGATTGAACATGCGACTATTTAGCCAC-CCAAATCGAAACGGAGCC) and a pair of mutagenesis primers (CA512: CCGTTTTCTGTATCGACTTCCCA- GTCCCATGC and CA511: GCATGGGACTGGGAAGTC-GATACAGAAAACGG) introducing the double deletion R180*+S181*, a variant gene (SEQ. ID NO: 9) was generated. These two fragments were assembled with an upstream fragment including the upper Pel locus and a downstream fragment including the lower Pel logi, so that the amylase upon transformation in *B.subtilis* will integrate in the Pel locus by double cross-over replacement.

The upper fragment further contains a triple promoter system (as described in WO 99/43835) consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence controlling the amylase expression, and the signal sequence of the *B.licheniformis* amylase signal to direct export out of the cells. The downstream fragment further contains the cat gene for selection on Chloramphenicol containing media.

Mutations were introduced by megaprimer mutagenesis method using a mutagenesis oligo coding for the desired amino acid change, and cloning into the expression cassette as for the reference amylase described above. The sequence was confirmed by DNA sequencing of the amylase gen.

Production and Purification of Amylases

The amylase expressing clones were fermented in media-16 at 37° C. with 180 rpm for 72 hours and the broths were centrifuged at 13131 g for 25 minutes to remove the cell mass, and then filtered using a 0.7 micro meter Glass filter GF-F, Whatman using tarsons filtration assembly. Reference and variant amylases were purified from the supernatant by 24 well plate protein purification method: 3 ml of a 50% slurry of butyl toyopearl resin in milli Q water were added into each well of 24 well filter plate and the plate subjected to vacuum to pack the column plate. The resin is equilibrated by adding 8 mL of equilibration buffer (50 mM HEPES, pH 8.0+1 M ammonium sulphate+1 mM CaCl2) and 8 ml of the amylase samples are the added into the wells of filter plate and incubate on plate mixer at 350 rpm for 8 min. The unbound fraction is removed by vacuum and the resin washed by 4 cycles of adding 8 mL of equilibration buffer (50 mM HEPES, pH 8.0+1 M ammonium sulphate+1 mM CaCl2) followed by mixing and incubation and finally removing the wash buffers by vacuum.

The amylase is eluted by adding elution buffer (50 mM HEPES, pH 8.0+1 mM CaCl2), mixed and incubated prior to collecting the amylase solution in a collection tray by vacuum.

Assays for Measurement of Amylolytic Activity (Alpha-Amylase Activity)

EnzChek Assay

The amylase activity or residual amylase activity can be determined by the following EnzCheck assay. The substrate is a corn starch derivative, DQTM starch (corn starch BODIPY FL conjugate), which is corn starch labeled with BODIPY® FL (4,4-difluoro-5,7-dimethyl-4-bora-3a,4a-diaza-s-indacene-3-propionic acid) dye to such a degree that the fluorescence is quenched. One vial containing approx. 1 mg lyophilized substrate is dissolved in 100 µL 50 mM sodium acetate pH 4.0. The vial is vortexed for 20 seconds and left at room temperature, in the dark, with occasional mixing until dissolved. Then 950 µL 10 mM sodium acetate, 0.01% (w/V) Triton X100 ((polyethylene glycol p-(1,1,3,3-tetramethylbutyl)-phenyl ether ($C_{14}H_{22}O(C_2H_4O)_n$ (n=9-10)), pH 5.0 is added, vortexed thoroughly and stored at room temperature, in the dark until ready to use. From 1 mL of this solution, the substrate working solution was prepared by mixing with 5 mL 50 mM HEPES, 0.01% (w/V) Triton X100, 1 mM CaCl2, pH 7.0.

The enzyme containing detergent is diluted to a concentration of 15 ng enzyme protein/ml (6826.7 times dilution) in 50 mM HEPES, 0.01% Triton X100, 1 mM CaCl2, pH 7.0.

For the assay, 25 µL of the substrate working solution is mixed for 10 second with 25 µL of the diluted enzyme in a black 384 well microtiter plate. The fluorescence intensity is measured (ex-citation: 485 nm, emission: 555 nm) once every second minute for 30 minutes in each well at 25° C. and the Vmax is calculated as the slope of the plot of fluorescence intensity against time. The plot should be linear and the residual activity assay has to been adjusted so that the diluted reference enzyme solution is within the linear range of the activity assay.

In a few instances there is a significant interference from the detergent without amylase on the assay. In such cases alternative amylase assays can be used. Interference from a detergent on an amylase assay can be tested by adding a known amount of amylase to the detergent at two levels and then measure the activity of the two samples. If the difference in the measured activities corresponds to the differences in the levels between the added amylases, the assay can be used to determine the residual activity of the amylase after storage.

PNP-G7 Assay

The alpha-amylase activity may be determined by a method employing the PNP-G7 substrate. PNP-G7 which is an abbreviation for 4,6-ethylidene(G7)-p-nitrophenyl(G1)-α, D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at 2=405 nm (400-420 nm.). Kits containing PNP-G7 substrate and alpha-Glucosidase are manufactured by Roche/Hitachi (cat. No. 11876473).

Reagents:

The G7-PNP substrate from this kit contains 22 mM 4,6-ethylidene-G7-PNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM MgCl2, 0.075 mM CaCl2, >4 kU/L alpha-glucosidase).

The substrate working solution is made by mixing 1 mL of the alpha-Glucosidase reagent with 0.2 mL of the G7-PNP substrate. This substrate working solution is made immediately before use.

Dilution buffer: 50 mM EPPS, 0.01% (w/v) Triton X100 (polyethylene glycol p-(1,1,3,3-tetramethylbutyl)-phenyl ether ($C_{14}H_{22}O(C_2H_4O)_n$ (n=9-10))), 1 mM CaCl2, pH7.0.

Procedure:

The amylase sample to be analysed was diluted in dilution buffer to ensure the pH in the diluted sample is 7. The assay was performed by transferring 20 µl diluted enzyme samples to 96 well microtiter plate and adding 80 µl substrate working solution. The solution was mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Determination of Percentage Point (pp)

The percentage point (pp) improvement in residual activity (stability) of the variant relative to the parent is calculated as the difference between the residual activity of the variant and the residual activity of the parent, i.e. the residual activity of the variant minus the residual activity of the parent.

Amylazyme Activity Assay:

The alpha-amylase activity can also be determined by a method using the Amylazyme substrate (from Megazyme, Ireland). An Amylazyme tablet includes interlinked amylose polymers that are in the form of globular microspheres that are insoluble in water. A blue dye is covalently bound to these microspheres. The interlinked amylose polymers in the microsphere are degraded at a speed that is proportional to the alpha-amylase activity. When the alpha-amylase degrades the amylose polymers, the released blue dye is water soluble and concentration of dye can be determined by measuring absorbance at 650 nm. The concentration of blue is proportional to the alpha-amylase activity in the sample.

The amylase sample to be analysed is diluted in activity buffer with the desired pH. One substrate tablet is suspended in 5 mL activity buffer and mixed on magnetic stirrer. During mixing of substrate transfer 150 µl to microtiter plate (MTP). Add 30 µl diluted amylase sample to 150 µl substrate and mix. Incubate for 15 minutes at 37° C. The reaction is stopped by adding 30 µl 1M NaOH and mix. Centrifuge MTP for 5 minutes at 4000×g. Transfer 100 µl to new MTP and measure absorbance at 620 nm.

The amylase sample should be diluted so that the absorbance at 650 nm is between 0 and 2.2, and is within the linear range of the activity assay.

Phadebas Activity Assay:

The alpha-amylase activity can also be determined by a method using the Phadebas substrate (from for example Magle Life Sciences, Lund, Sweden). A Phadebas tablet includes interlinked starch polymers that are in the form of globular microspheres that are insoluble in water. A blue dye is covalently bound to these microspheres. The interlinked starch polymers in the microsphere are degraded at a speed that is proportional to the alpha-amylase activity. When the alpha-amylase degrades the starch polymers, the released blue dye is water soluble and concentration of dye can be determined by measuring absorbance at 650 nm. The concentration of blue is proportional to the alpha-amylase activity in the sample.

The amylase sample to be analysed is diluted in activity buffer with the desired pH. One substrate tablet is suspended in 5 mL activity buffer and mixed on magnetic stirrer. During mixing of substrate transfer 150 µl to microtiter plate (MTP). Add 30 µl diluted amylase sample to 150 µl substrate and mix. Incubate for 15 minutes at 37° C. The reaction is stopped by adding 30 µl 1M NaOH and mix. Centrifuge MTP for 5 minutes at 4000×g. Transfer 100 µl to new MTP and measure absorbance at 620 nm.

The amylase sample should be diluted so that the absorbance at 650 nm is between 0 and 2.2, and is within the linear range of the activity assay.

Reducing Sugar Activity Assay

The alpha-amylase activity can also be determined by reducing sugar assay with for example corn starch substrate. The number of reducing ends formed by the alpha-amylase hydrolysing the alpha-1,4-glycosidic linkages in starch is determined by reaction with p-Hydroxybenzoic acid hydrazide (PHBAH). After reaction with PHBAH the number of reducing ends can be measured by absorbance at 405 nm and the concentration of reducing ends is proportional to the alpha-amylase activity in the sample.

The corns starch substrate (3 mg/ml) is solubilised by cooking for 5 minutes in milliQ water and cooled down before assay. For the stop solution prepare a Ka-Na-tartrate/NaOH solution (K—Na-tartrate (Merck 8087) 50 g/l, NaOH 20 g/l) and prepare freshly the stop solution by adding p-Hydroxybenzoic acid hydrazide (PHBAH, Sigma H9882) to Ka-Na-tartrate/NaOH solution to 15 mg/ml.

In PCR-MTP 50 µl activity buffer is mixed with 50 µl substrate. Add 50 µl diluted enzyme and mix. Incubate at the desired temperature in PCR machine for 5 minutes. Reaction is stopped by adding 75 µl stop solution (Ka-Na-tartrate/NaOH/PHBAH). Incubate in PCR machine for 10 minutes at 95° C. Transfer 150 µl to new MTP and measure absorbance at 405 nm.

The amylase sample should be diluted so that the absorbance at 405 nm is between 0 and 2.2, and is within the linear range of the activity assay.

Wash Performance of Alpha-Amylases Using Automatic Mechanical Stress Assay

In order to assess the wash performance of the alpha-amylases in a detergent base composition, washing experiments may be performed using Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress in a regular, periodic oscillating manner. For further description see WO 02/42740, especially the paragraph "Special method embodiments" at page 23-24.

General Wash Performance Description

A test solution comprising water (6° dH), 0.79 g/L detergent, e.g. model detergent J as described below, and the enzyme of the invention at concentration of 0 or 0.2 mg enzyme protein/L, is prepared. Fabrics stained with starch (CS-28 from Center For Test materials BV, P.O. Box 120, 3133 KT, Vlaardingen, The Netherlands) is added and washed for 20 minutes at 15° C. and 30° C., or alternatively 20 minutes at 15° C. and 40° C. as specified in the examples. After thorough rinse under running tap water and drying in the dark, the light intensity values of the stained fabrics are subsequently measured as a measure for wash performance. The test with 0 mg enzyme protein/L is used as a blank and corresponds to the contribution from the detergent. Preferably mechanical action is applied during the wash step, e.g. in the form of shaking, rotating or stirring the wash solution with the fabrics. The AMSA wash performance experiments were conducted under the experimental conditions specified below:

TABLE A

| Experimental condition | |
|---|---|
| Detergent | Liquid Model detergent J (see Table B) |
| Detergent dosage | 0.79 g/L |
| Test solution volume | 160 micro L |
| pH | As is |
| Wash time | 20 minutes |

TABLE A-continued

Experimental condition

| | |
|---|---|
| Temperature | 15° C. or 30° C. |
| Water hardness | 6° dH |
| Enzyme concentration in test | 0.2 mg enzyme protein/L |
| Test material | CS-28 (Rice starch cotton) |

TABLE B

Model detergent J

| Compound | Content of compound (% w/w) | % active component (% w/w) |
|---|---|---|
| LAS | 5.15 | 5.00 |
| AS | 5.00 | 4.50 |
| AEOS | 14.18 | 10.00 |
| Coco fatty acid | 1.00 | 1.00 |
| AEO | 5.00 | 5.00 |
| MEA | 0.30 | 0.30 |
| MPG | 3.00 | 3.00 |
| Ethanol | 1.50 | 1.35 |
| DTPA (as Na5 salt) | 0.25 | 0.10 |
| Sodium citrate | 4.00 | 4.00 |
| Sodium formate | 1.00 | 1.00 |
| Sodium hydroxide | 0.66 | 0.66 |
| H$_2$O, ion exchanged | 58.95 | 58.95 |

Water hardness was adjusted to 6° dH by addition of CaCl$_2$, MgCl$_2$, and NaHCO$_3$ (Ca$^{2+}$:Mg$^{2+}$:HCO$_3^-$ = 2:1:4.5) to the test system. After washing the textiles were flushed in tap water and dried.

TABLE C

Experimental condition

| | |
|---|---|
| Detergent | Liquid Model detergent A (see Table D) |
| Detergent dosage | 3.33 g/L |
| Test solution volume | 160 micro L |
| pH | As is |
| Wash time | 20 minutes |
| Temperature | 15° C. or 40° C. |
| Water hardness | 15° dH |
| Enzyme concentration in test | 0.2 mg enzyme protein/L |
| Test material | CS-28 (Rice starch cotton) |

TABLE D

Model detergent A

| Compound | Content of compound (% w/w) | % active component (% w/w) |
|---|---|---|
| LAS | 12.00 | 11.60 |
| AEOS, SLES | 17.63 | 4.90 |
| Soy fatty acid | 2.75 | 2.48 |
| Coco fatty acid | 2.75 | 2.80 |
| AEO | 11.00 | 11.00 |
| Sodium hydroxide | 1.75 | 1.80 |
| Ethanol/Propan-2-ol | 3.00 | 2.70/0.30 |
| MPG | 6.00 | 6.00 |
| Glycerol | 1.71 | 1.70 |
| TEA | 3.33 | 3.30 |
| Sodium formate | 1.00 | 1.00 |
| Sodium citrate | 2.00 | 2.00 |
| DTMPA | 0.48 | 0.20 |
| PCA | 0.46 | 0.18 |
| Phenoxy ethanol | 0.50 | 0.50 |
| H$_2$O, ion exchanged | 33.64 | 33.64 |

Water hardness was adjusted to 15° dH by addition of CaCl$_2$, MgCl$_2$, and NaHCO$_3$ (Ca$^{2+}$:Mg$^{2+}$:HCO$_3^-$ = 4:1:7.5) to the test system. After washing the textiles were flushed in tap water and dried.

TABLE E

Experimental condition

| | |
|---|---|
| Detergent | Powder Model detergent X (see Table F) |
| Detergent dosage | 1.75 g/L |
| Test solution volume | 160 micro L |
| pH | As is |
| Wash time | 20 minutes |
| Temperature | 15° C. or 30° C. |
| Water hardness | 12° dH |
| Enzyme concentration in test | 0.2 mg enzyme protein/L |
| Test material | CS-28 (Rice starch cotton) |

TABLE F

Model detergent X

| Compound | Content of compound (% w/w) | % active component (% w/w) |
|---|---|---|
| LAS | 16.50 | 15.00 |
| AEO* | 2.00 | 2.00 |
| Sodium carbonate | 20.00 | 20.00 |
| Sodium (di)silicate | 12.00 | 9.90 |
| Zeolite A | 15.00 | 12.00 |
| Sodium sulfate | 33.50 | 33.50 |
| PCA | 1.00 | 1.00 |

*Model detergent X is mixed without AEO. AEO is added separately before wash. Water hardness was adjusted to 12° dH by addition of CaCl$_2$, MgCl$_2$, and NaHCO$_3$ (Ca$^{2+}$:Mg$^{2+}$:HCO$_3^-$ = 2:1:4.5) to the test system. After washing the textiles were flushed in tap water and dried.

Model Detergents 1 and 2

| Component | Model 1 % w/w | Model 2 % w/w |
|---|---|---|
| LAS | 12 | 12 |
| AEOS | 4.9 | 4.9 |
| Soap (cocoa) | 2.75 | 2.75 |
| Soap (soya) | 2.75 | 2.75 |
| AEO N25-7 | 11 | 11 |
| NaOH | 1.75 | 1.75 |
| Ethanol | 3 | 3 |
| MPG | 6 | 6 |
| Glycerol | 1.7 | 1.7 |
| TEA | 3.3 | 3.3 |
| Sodium formate | 1 | 1 |
| Sodium citrate | 2 | 2 |
| HEDP | 0 | 0.5 |
| PCA (Sokalan CP-5) | 0.18 | 0.18 |
| Ion exchanged water | 34.2 | 34.2 |
| DTMPA | 0.2 | 0 |

The wash performance is measured as the brightness expressed as the intensity of the light reflected from the sample when illuminated with white light. When the sample is stained the intensity of the reflected light is lower, than that of a clean sample. Therefore the intensity of the reflected light can be used to measure wash performance. Color measurements are made with a professional flatbed scanner (Kodak iQsmart, Kodak) used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int = \sqrt{r^2 + g^2 + b^2}$$

Textile:

Textile sample CS-28 (rice starch on cotton) is obtained from Center For Testmaterials BV, P.O. Box 120, 3133 KT Vlaardingen, the Netherlands.

Automatic Mechanical Stress Assay (AMSA) for Automatic Dish Wash

Washing experiments are performed in order to assess the wash performance of selected alpha-amylase variants in dishwash detergent compositions. The alpha-amylase variants of the present application may be tested using the Automatic Mechanical Stress Assay (AMSA). With the AMSA, the wash performance of many small volume enzyme-detergent solutions can be examined. The AMSA plate has a number of slots for test solutions and a lid that firmly squeezes the melamine tile to be washed against the slot openings. During the wash, the plate, test solutions, melamine tile and lid are vigorously shaken to bring the test solution in contact with the soiled melamine tile and apply mechanical stress in a regular, periodic oscillating manner. For further description see WO 02/42740 especially the paragraph "Special method embodiments" at page 23-24. The experiment may be conducted under the experimental conditions as specified in the table(s) below:

| ADW model detergent with MGDA | MGDA (40%) 30% |
| --- | --- |
| | Sodium carbonate 20% |
| | Sodium percarbonate 10% |
| | Sodium disilicate 5% |
| | TAED 5% |
| | Sokalan CP5 (39.5%) 10% |
| | Surfac 23-6.5 (100%) 5% |
| | Sodium Sulfate 15% |
| Detergent dosage | 3.33 g/L |
| Test solution volume | 160 micro L |
| pH | As is |
| Wash time | 20 minutes |
| Temperature | 50° C. |
| Water hardness | 17° dH |
| Enzyme concentration in test solution | 0.925, 1.85, 5.55, 11 mg enzyme protein/liter |
| Test material | melamine tiles with starch such as DM-77 and DM-78 |

| ADW model detergent with STPP | STPP 50% |
| --- | --- |
| | Sodium carbonate 20% |
| | Sodium percarbonate 10% |
| | Sodium disilicate 5% |
| | TAED 2% |
| | Sokalan CP5 (39.5%) 5% |
| | Surfac 23-6.5 (100%) 2% |
| | Phosphonate 6% |
| Detergent dosage | 3.33 g/L |
| Test solution volume | 160 micro L |
| pH | As is |
| Wash time | 20 minutes |
| Temperature | 50° C. |
| Water hardness | 17° dH |
| Enzyme concentration in test solution | 0.925, 1.85, 5.55, 11 mg enzyme protein/liter |
| Test material | melamine tiles with starch such as DM-77 and DM-78 |

Water hardness is adjusted to 17° dH by addition of $CaCl_2$, $MgCl_2$, and $NaHCO_3$ ($Ca^{2+}:Mg^{2+}=4:1:10$) to the test system. After washing the melamine tiles were flushed in tap water and dried.

The performance of the enzyme variant is measured as the brightness of the colour of the melamine tile washed with that specific alpha-amylase. Brightness can also be expressed as the intensity of the light reflected from the sample when illuminated with white light. When the sample is stained the intensity of the reflected light is lower, than that of a clean sample. Therefore the intensity of the reflected light can be used to measure wash performance of a protease.

Colour measurements are made with a professional flat-bed scanner (Kodak iQsmart, Kodak, Midtager 29, DK-2605 Brondby, Denmark), which is used to capture an image of the washed melamine tiles.

To extract a value for the light intensity from the scanned images, a special designed software application is used (Novozymes Colour Vector Analyzer). The program retrieves the 24 bit pixel values from the image and converts them into values for red, green and blue (RGB). The intensity value (Int) is calculated by adding the RGB values together as vectors and then taking the length of the resulting vector:

$$Int=\sqrt{r^2+g^2+b^2}$$

Textiles:

Standard melamine tiles with starch such as DM-77 and DM-78 may be obtained from Center For Testmaterials BV, P.O. Box 120, 3133 KT Vlaardingen, the Netherlands.

AMSA Wash Performance

The wash performance of the variants and corresponding parent alpha-amylases is tested by the AMSA-test method as described in the Methods section. The results are given as (performance of variant minus performance of blank) divided by (performance of parent minus performance of blank) multiplied by 100, where the blank is the performance obtained by washing at the same conditions, but in the absence of alpha-amylase.

Terg-O-Tometer (TOM) Wash Assay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines.

Equipment:

The water bath with 12 steel beakers and 1 rotating arm per beaker with capacity of 500 or 1200 mL of detergent solution. Temperature ranges from 5 to 80° C. The water bath has to be filled up with deionised water. Rotational speed can be set up to 70 to 120 rpm/min.

TOM Wash Performance

Water hardness is adjusted to the strength described below by addition of $CaCl_2$, $MgCl_2$ and $NAHCO_3$. Wash solutions are prepared with desired amount of detergent, temperature and water hardness in a bucket as described below. Detergent is dissolved during magnet stirring for 10 min.

Temperature and rotation (rpm) in the water bath in the Terg-O-Tometer is set according to the settings below. When temperature is adjusted according to settings (tolerance is +/−0.5° C.) wash solution is added to TOM beaker according to the amount described below.

Agitation in the beaker is at 120 rpm. 2 rice starch swatches (CS-28) and soil ballast are added to each of the beakers and wash carried out according to time stated below. Swatches are rinsed in cold tap water for 5 min. The swatches are left to dry in the dark overnight.

Textile:

Textile sample CS-28 (rice starch on cotton) is obtained from Center for Test materials BV, P.O. Box 120, 3133 KT Vlaardingen, the Netherlands.

Soil Ballast:

Soil ballast Rice starch on cotton/polyester (EMPA 162) is obtained from Center for Test materials BV, P.O. Box 120, 3133 KT Vlaardingen, the Netherlands. Bistro gravy (063KC), Frij Chocolate milkshake, Heinz spaghetti (113KC), Herseys double chocolate is obtained from Warwick Equest Ltd, Unit 55, Consett Business Park, Consett, County Durham, DH8 6BN UK Experimental Conditions TOM

|  | European (EU) conditions | Northern America (US) conditions |
|---|---|---|
| Detergent dosage | 5.77 g/L (liquid detergent) | 0.78 g/L (liquid detergent) |
| Water hardness | 15° dH ($Ca^{2+}:Mg^{2+}:HCO_3^-$ = 4:1:7.5) | 6° dH ($Ca^{2+}:Mg^{2+}:HCO_3^-$ = 2:1:4.5) |
| Enzyme concentration in wash solution | 0.25 mg enzyme protein/L | 0.08 mg enzyme protein/L |
| Test solution volume | 500 ml | 800 ml |
| Wash time | 30 minutes | 18 minutes |
| Rotation | 120 rpm | |
| pH | as is | |
| Temperature | 15° C. | |

Detergents and test materials may be as follows:

| Laundry liquid detergent | May be as described below |
|---|---|
| Test material | CS-28 (Rice starch on cotton) |
| Soil ballast | Rice starch on polyester/cotton (EMPA 162), Bistro gravy (063KC), Frij Chocolate milkshake, Heinz spaghetti (113KC), Herseys double chocolate (2 swatches of each) |

The wash performance is measured as the brightness of the color of the textile washed, expressed in remission values. Remission measurements are made using a Macbeth 7000 Color Eye spectrophotometer. Each of the dry swatches is to be measured. As there is a risk of interference from the back-ground, the swatches are placed on top of 4 layers of fabric during the measurement of the remission. The remission is measured at 460 nm. The UV filter is not included. An average result for remission for the swatches is calculated.

EXAMPLES

Example 1 Residual Activity after Incubation with Model Detergent J at 40° C.

The (residual) amylase activity of the variants of the present invention was determined by the Amylazyme assay as described under Methods.

The stability test was carried out by mixing 50 ul amylase sample with 450 ul model J, and aliquot this mixture into two tubes that are incubated in 40° C. incubator for 90 minutes or incubated in refrigerator at 4° C. for 90 minutes, respectively.

The incubated samples are diluted 10× in assay buffer (100 mM B&R buffer pH 7.3 with 0.12 mM CaCl2 and 0.01% brij) prior to measuring the activity using the Amylazyme assay.

The stability index is calculated relative to the residual activity of the reference amylase subjected to the same test. The reference alpha-amylase is the amylase of SEQ ID NO: 2 having a deletion of the amino acids R180+S181 which alpha-amylase is disclosed herein as SEQ ID NO: 10. In other words, in the below table, the parent for the variants is the alpha-amylase having the amino acid sequence of SEQ ID NO: 10. Thus, in the below table "L205F" means an alpha-amylase variant having the sequence of SEQ ID NO: 2 but having a deletion of (R180+S181) and further having a substitution of L205F.

| Amylase variaint (reference + mutation) | Stability index |
|---|---|
| Reference (SEQ ID NO: 10) | 100 |
| L205F | 260 |
| Reference | 100 |
| Y48W + L205Y | 177 |
| N174NQ | 334 |
| Y48W + V60A | 134 |
| Y48W + F105M | 146 |
| V60A + L205Y | 313 |
| Reference (SEQ ID NO: 10) | 100 |
| R309Q | 198 |
| M317L | 243 |
| Y48W | 197 |
| I390E | 187 |
| Y48W + V60A + F105M | 184 |
| Y48W + V60A + L205Y | 229 |
| V60A + F105M + L205Y | 219 |
| Reference (SEQ ID NO: 10) | 100 |
| Y48W + V60A + L205F | 186 |
| V60A + F105M + L205F | 189 |
| Reference (SEQ ID NO: 10) | 100 |
| L205Y | 129 |
| L173LR | 103 |
| L173LL | 118 |
| N174NF | 140 |
| N174NL | 181 |
| N174NA | 161 |
| E169EQ | 159 |
| S170SL | 101 |
| R171RR | 124 |
| R171RQ | 118 |
| R171RL | 116 |
| Reference (SEQ ID NO: 10) | 100 |
| K172KF | 137 |
| K172KL | 127 |
| K172KN | 125 |
| K172KR | 108 |
| K172KA | 116 |
| L173LA | 146 |
| R171RN | 109 |
| R171RF | 130 |
| K172KN | 120 |
| N174NN | 207 |
| N174NS | 157 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An alpha-amylase variant comprising
   a) a deletion at two or more positions corresponding to positions R180, S181, T182 and G183 of the mature polypeptide of SEQ ID NO: 1 or 2, and
   b) an alteration at two or more positions corresponding to positions Y48, E169, S170, R171, K172, N174, M317, I390, of the mature polypeptide of SEQ ID NO: 1 or 2, wherein each alteration is independently a substitution or an insertion,
   wherein the variant has at least 80%, but less than 100%, sequence identity, with the mature polypeptide of SEQ ID NO: 1 or 2, wherein the variant has alpha-amylase activity.

2. The variant of claim 1, wherein the deletion a) is selected from the list consisting of R180*+S181*, R180*+T182*, R180*+G183*, S181*+T182*, S181*+G183*, and T182*+G183*, preferably R180*+S181*.

3. The variant of claim 1 further comprising a substitution at one or both positions corresponding to positions G475 and S243 of the mature polypeptide of SEQ ID NO: 1 or 2, preferably G475K and/or S243Q.

4. The variant of claim 1, wherein the alteration b) is at three or more of said positions, four or more of said positions, five or more of said positions, six or more of said positions, seven or more of said positions, eight or more of said positions, or nine or more of said positions.

5. The variant of claim 1, wherein the number of alterations is 2-20.

6. The variant of claim 1, which has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, but less than 100%, sequence identity to the amino acid sequence of SEQ ID NO: 1.

7. The variant of claim 1, which has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99%, but less than 100%, sequence identity, to the amino acid sequence of SEQ ID NO: 2.

8. The variant of claim 1, which is a variant of a parent alpha-amylase selected from the group consisting of:
   a. a polypeptide having at least 80% sequence identity to the mature polypeptide of SEQ ID NO: 1;
   b. a polypeptide having at least 80% sequence identity to the mature polypeptide of SEQ ID NO: 2;
   c. a fragment of the mature polypeptide of SEQ ID NO: 1, which has alpha-amylase activity;
   d. a fragment of the mature polypeptide of SEQ ID NO: 2, which has alpha-amylase activity;
   e. a polypeptide having immunological cross reactivity with an antibody raised against the mature polypeptide of SEQ ID NO: 1;
   f. a polypeptide having immunological cross reactivity with an antibody raised against the mature polypeptide of SEQ ID NO: 2;
   g. a polypeptide encoded by a polynucleotide that hybridizes under medium-high stringency conditions with (i) the mature polypeptide coding sequence of SEQ ID NO: 11, or (ii) the full-length complement thereof;

h. a polypeptide encoded by a polynucleotide having at least 80% sequence identity to the mature polypeptide coding sequence of SEQ ID NO: 11.

9. The variant of claim 8, wherein the parent alpha-amylase has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99% sequence identity to SEQ ID NO: 1.

10. The variant of claim 8, wherein the parent alpha-amylase has at least 85%, at least 86%, at least 87%, at least 88%, at least 89%, at least 90%, at least 91%, at least 92%, at least 93%, at least 94%, at least 95% identity, at least 96%, at least 97%, at least 98%, or at least 99% sequence identity to SEQ ID NO: 2.

11. The variant of claim 1, wherein the parent alpha-amylase comprises or consists of the mature polypeptide of SEQ ID NO: 1.

12. The variant of claim 1, wherein the parent alpha-amylase comprises or consists of the mature polypeptide of SEQ ID NO: 2.

13. The variant of claim 1, which has an improved property relative to the parent, wherein the improved property is selected from the group consisting of catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity, thermo stability, and preferably improved washing performance at low temperature.

14. The variant of claim 1, wherein the variant has improved detergent stability compared to the alpha-amylase of SEQ ID NO: 1 or 2.

15. The variant of claim 1, wherein the variant has improved detergent stability compared to the alpha-amylase of SEQ ID NO: 2 having a deletion of amino acids R180 and S181 wherein the stability is tested in model detergent J at 40° C. for 90 minutes.

16. A detergent composition comprising a variant alpha-amylase of claim 1.

17. An isolated polynucleotide encoding the variant of claim 1.

18. A nucleic acid construct comprising the polynucleotide of claim 17.

19. An expression vector comprising the polynucleotide of claim 17.

20. A host cell comprising the polynucleotide of claim 17.

21. A method of producing an alpha-amylase variant, comprising:
   a) cultivating the host cell of claim 20 under conditions suitable for expression of the variant; and
   b) recovering the variant.

22. A method for obtaining an alpha-amylase variant, comprising introducing into a parent alpha-amylase having at least 80% sequence identity to SEQ ID NO: 1 or 2
   a) a deletion at two or more positions corresponding to positions R180, S181, T182 and G183 of the mature polypeptide of SEQ ID NO: 1 or 2 and
   b) an alteration at two or more positions corresponding to positions Y48, E169, S170, R171, K172, L173, N174, L205, R309, M317, I390 of the mature polypeptide of SEQ ID NO: 1 or 2, wherein each alteration is independently a substitution or insertion,
wherein the variant has at least 80%, but less than 100%, sequence identity with the mature polypeptide of SEQ ID NO: 1 or 2, wherein the variant has alpha-amylase activity; and recovering the variant.

23. A method of improving the detergent stability of an alpha-amylase by introducing into a parent alpha-amylase
   a) a deletion at two or more positions corresponding to positions R180, S181, T182 and G183 of the mature polypeptide of SEQ ID NO: 1 or 2 and
   b) an alteration at two or more positions corresponding to positions Y48, E169, S170, R171, K172, N174, M317, I390 of the mature polypeptide of SEQ ID NO: 1 or 2, wherein each alteration is independently a substitution or insertion,
wherein the resulting variant has at least 80%, but less than 100%, sequence identity with the mature polypeptide of SEQ ID NO: 1 or 2, wherein the resulting variant has alpha-amylase activity and an improved detergent stability compared to the parent alpha-amylase.

* * * * *

SEQUENCE LISTING

<160> NUMBER OF SEQ ID NOS: 15

<210> SEQ ID NO 1
<211> LENGTH: 583
<212> TYPE: PRT
<213> ORGANISM: Bacillus sp. TS-23

<400> SEQUENCE: 1

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

-continued

```
Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
                420                 425                 430

Pro Gly Gly Ser Lys Trp Met Tyr Val Gly Lys Lys His Ala Gly Lys
                435                 440                 445

Val Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
                485                 490                 495

Thr Thr Ser Gly Gln Asn Val Tyr Val Val Ala Asn Ile Pro Glu Leu
                500                 505                 510

Gly Asn Trp Asn Thr Ala Asn Ala Ile Lys Met Asn Pro Ser Ser Tyr
                515                 520                 525

Pro Thr Trp Lys Ala Thr Ile Ala Leu Pro Gln Gly Lys Ala Ile Glu
                530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
                565                 570                 575

Thr Ala Ser Trp Asn Val Pro
                580

<210> SEQ ID NO 2
<211> LENGTH: 484
<212> TYPE: PRT
<213> ORGANISM: Bacillus sp. TS-23

<400> SEQUENCE: 2

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
                35                  40                  45

Lys Gly Thr Ser Gln Ser Asp Val Gly Tyr Gly Val Tyr Asp Leu Tyr
50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gly Thr Glu Phe Val Asp Ala Val Glu Val Asp Pro Ser Asn Arg Asn
                115                 120                 125

Gln Glu Thr Ser Gly Thr Tyr Gln Ile Gln Ala Trp Thr Lys Phe Asp
                130                 135                 140

Phe Pro Gly Arg Gly Asn Thr Tyr Ser Ser Phe Lys Trp Arg Trp Tyr
145                 150                 155                 160
```

His Phe Asp Gly Thr Asp Trp Asp Glu Ser Arg Lys Leu Asn Arg Ile
            165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
            195                 200                 205

His Pro Glu Val Val Thr Glu Leu Lys Asn Trp Gly Thr Trp Tyr Val
210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
            245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
            275                 280                 285

Asp Ala Pro Leu His Asn Asn Phe Tyr Thr Ala Ser Lys Ser Ser Gly
            290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
            325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Gly Leu Lys Ser Lys
370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
            405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
            435                 440                 445

Val Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Ala Lys

<210> SEQ ID NO 3
<211> LENGTH: 583
<212> TYPE: PRT
<213> ORGANISM: Bacillus sp.

<400> SEQUENCE: 3

Asn Thr Ala Pro Val Asn Gly Thr Met Met Gln Tyr Phe Glu Trp Asp
1               5                   10                  15

Leu Pro Asn Asp Gly Thr Leu Trp Thr Lys Val Lys Asn Glu Ala Ser
            20                  25                  30

Ser Leu Ser Ala Leu Gly Ile Thr Ala Leu Trp Leu Pro Pro Ala Tyr
        35                  40                  45

```
Lys Gly Thr Ser Gln Ala Asp Val Gly Tyr Gly Val Tyr Asp Leu Tyr
     50                  55                  60

Asp Leu Gly Glu Phe Asn Gln Lys Gly Thr Ile Arg Thr Lys Tyr Gly
 65                  70                  75                  80

Thr Lys Thr Gln Tyr Leu Gln Ala Ile Gln Ala Lys Ser Ala Gly
                     85                  90                  95

Met Gln Val Tyr Ala Asp Val Val Phe Asn His Lys Ala Gly Ala Asp
                100                 105                 110

Ser Thr Glu Trp Val Asp Ala Val Glu Val Asn Pro Ser Asn Arg Asn
                115                 120                 125

Gln Glu Thr Ser Gly Thr Tyr Gln Ile Gln Ala Trp Thr Lys Phe Asp
                130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                    165                 170                 175

Tyr Lys Phe Arg Gly Thr Gly Lys Ala Trp Asp Trp Glu Val Asp Thr
                180                 185                 190

Glu Asn Gly Asn Tyr Asp Tyr Leu Met Phe Ala Asp Leu Asp Met Asp
                195                 200                 205

His Pro Glu Val Val Ala Glu Leu Lys Asn Trp Gly Lys Trp Tyr Val
210                 215                 220

Asn Thr Thr Asn Val Asp Gly Phe Arg Leu Asp Ala Val Lys His Ile
225                 230                 235                 240

Lys Tyr Ser Phe Phe Pro Asp Trp Leu Ser Tyr Val Arg Asn Gln Thr
                245                 250                 255

Gly Lys Asn Leu Phe Ala Val Gly Glu Phe Trp Gly Tyr Asp Val Asn
                260                 265                 270

Lys Leu His Asn Tyr Ile Thr Lys Thr Asn Gly Ala Met Ser Leu Phe
                275                 280                 285

Asp Ala Pro Leu His Asn Asn Phe Tyr Ile Ala Ser Lys Ser Ser Gly
                290                 295                 300

Tyr Phe Asp Met Arg Tyr Leu Leu Asn Asn Thr Leu Met Lys Asp Gln
305                 310                 315                 320

Pro Ala Leu Ala Val Thr Leu Val Asp Asn His Asp Thr Gln Pro Gly
                    325                 330                 335

Gln Ser Leu Gln Ser Trp Val Glu Pro Trp Phe Lys Pro Leu Ala Tyr
                340                 345                 350

Ala Phe Ile Leu Thr Arg Gln Glu Gly Tyr Pro Cys Val Phe Tyr Gly
                355                 360                 365

Asp Tyr Tyr Gly Ile Pro Lys Tyr Asn Ile Pro Gly Leu Lys Ser Lys
370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                    405                 410                 415

Ile Asp Ala Lys Pro Asn Ser Gly Leu Ala Ala Leu Ile Thr Asp Gly
                420                 425                 430

Pro Gly Gly Ser Lys Trp Met Tyr Val Gly Lys Arg His Ala Gly Lys
                435                 440                 445

Val Phe Tyr Asp Leu Thr Gly Asn Arg Ser Asp Thr Val Thr Ile Asn
450                 455                 460
```

```
Ala Asp Gly Trp Gly Glu Phe Lys Val Asn Gly Ser Val Ser Ile
465                 470                 475                 480

Trp Val Ala Lys Thr Ser Asn Val Thr Phe Thr Val Asn Asn Ala Thr
                485                 490                 495

Thr Val Tyr Gly Gln Asn Val Tyr Val Gly Asn Ile Pro Glu Leu
            500                 505                 510

Gly Asn Trp Asn Ile Ala Asn Ala Ile Gln Met Thr Pro Ser Ser Tyr
            515                 520                 525

Pro Thr Trp Lys Thr Thr Val Ser Leu Pro Gln Gly Lys Ala Ile Glu
            530                 535                 540

Phe Lys Phe Ile Lys Lys Asp Ser Ala Gly Asn Val Ile Trp Glu Asn
545                 550                 555                 560

Ile Ala Asn Arg Thr Tyr Thr Val Pro Phe Ser Ser Thr Gly Ser Tyr
                565                 570                 575

Thr Ala Asn Trp Asn Val Pro
            580

<210> SEQ ID NO 4
<211> LENGTH: 484
<212> TYPE: PRT
<213> ORGANISM: bacillus sp.

<400> SEQUENCE: 4

Asn Thr Ala Pro Val Asn Gly Thr Met Met Gln Tyr Phe Glu Trp Asp
1               5                   10                  15

Leu Pro Asn Asp Gly Thr Leu Trp Thr Lys Val Lys Asn Glu Ala Ser
                20                  25                  30

Ser Leu Ser Ala Leu Gly Ile Thr Ala Leu Trp Leu Pro Pro Ala Tyr
            35                  40                  45

Lys Gly Thr Ser Gln Ala Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Tyr Leu Gln Ala Ile Gln Ala Ala Lys Ser Ala Gly
                85                  90                  95

Met Gln Val Tyr Ala Asp Val Val Phe Asn His Lys Ala Gly Ala Asp
            100                 105                 110

Ser Thr Glu Trp Val Asp Ala Val Glu Val Asn Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Ala Glu Leu Lys Asn Trp Gly Lys Trp Tyr Val
    210                 215                 220

Asn Thr Thr Asn Val Asp Gly Phe Arg Leu Asp Ala Val Lys His Ile
225                 230                 235                 240

Lys Tyr Ser Phe Phe Pro Asp Trp Leu Ser Tyr Val Arg Asn Gln Thr
                245                 250                 255
```

-continued

```
Gly Lys Asn Leu Phe Ala Val Gly Glu Phe Trp Gly Tyr Asp Val Asn
            260                 265                 270

Lys Leu His Asn Tyr Ile Thr Lys Thr Asn Gly Ala Met Ser Leu Phe
            275                 280                 285

Asp Ala Pro Leu His Asn Asn Phe Tyr Ile Ala Ser Lys Ser Ser Gly
            290                 295                 300

Tyr Phe Asp Met Arg Tyr Leu Leu Asn Asn Thr Leu Met Lys Asp Gln
305                 310                 315                 320

Pro Ala Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Gly Leu Lys Ser Lys
            370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Ala Lys Pro Asn Ser Gly Leu Ala Ala Leu Ile Thr Asp Gly
            420                 425                 430

Pro Gly Gly Ser Lys Trp Met Tyr Val Gly Lys Arg His Ala Gly Lys
            435                 440                 445

Val Phe Tyr Asp Leu Thr Gly Asn Arg Ser Asp Thr Val Thr Ile Asn
            450                 455                 460

Ala Asp Gly Trp Gly Glu Phe Lys Val Asn Gly Gly Ser Val Ser Ile
465                 470                 475                 480

Trp Val Ala Lys
```

<210> SEQ ID NO 5
<211> LENGTH: 586
<212> TYPE: PRT
<213> ORGANISM: bacillus sp.

<400> SEQUENCE: 5

```
Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
            20                  25                  30

Ser Leu Ala Asn Leu Gly Ile Thr Ala Leu Trp Leu Pro Pro Ala Tyr
            35                  40                  45

Lys Gly Thr Ser Ser Asp Val Gly Tyr Gly Val Tyr Asp Leu Tyr
            50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
            85                  90                  95

Met Gln Val Tyr Ala Asp Val Val Phe Asn His Lys Ala Gly Ala Asp
            100                 105                 110

Gly Thr Glu Leu Val Asp Ala Val Glu Val Asn Pro Ser Asp Arg Asn
            115                 120                 125

Gln Glu Ile Ser Gly Thr Tyr Gln Ile Gln Ala Trp Thr Lys Phe Asp
            130                 135                 140
```

```
Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
    210                 215                 220

Thr Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Val Arg Thr Gln Thr
                245                 250                 255

Gln Lys Pro Leu Phe Ala Val Gly Glu Phe Trp Ser Tyr Asp Ile Ser
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Ile Ala Ser Lys Ser Gly Gly
290                 295                 300

Tyr Phe Asp Met Arg Thr Leu Leu Asn Asn Thr Leu Met Lys Asp Gln
305                 310                 315                 320

Pro Thr Leu Ala Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Ala Leu Lys Ser Lys
    370                 375                 380

Leu Asp Pro Leu Leu Ile Ala Arg Arg Asp Tyr Ala Tyr Gly Thr Gln
385                 390                 395                 400

His Asp Tyr Ile Asp Ser Ala Asp Ile Ile Gly Trp Thr Arg Glu Gly
                405                 410                 415

Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
        435                 440                 445

Thr Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Pro Lys Ile Ser Thr Thr Ser Gln Ile Thr Phe Thr Val Asn
                485                 490                 495

Asn Ala Thr Thr Val Trp Gly Gln Asn Val Tyr Val Val Gly Asn Ile
            500                 505                 510

Ser Gln Leu Gly Asn Trp Asp Pro Val His Ala Val Gln Met Thr Pro
        515                 520                 525

Ser Ser Tyr Pro Thr Trp Thr Val Thr Ile Pro Leu Leu Gln Gly Gln
    530                 535                 540

Asn Ile Gln Phe Lys Phe Ile Lys Lys Asp Ser Ala Gly Asn Val Ile
545                 550                 555                 560
```

```
Trp Glu Asp Ile Ser Asn Arg Thr Tyr Thr Val Pro Thr Ala Ala Ser
                565                 570                 575

Gly Ala Tyr Thr Ala Ser Trp Asn Val Pro
            580                 585

<210> SEQ ID NO 6
<211> LENGTH: 484
<212> TYPE: PRT
<213> ORGANISM: bacillus sp.

<400> SEQUENCE: 6

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
            20                  25                  30

Ser Leu Ala Asn Leu Gly Ile Thr Ala Leu Trp Leu Pro Pro Ala Tyr
        35                  40                  45

Lys Gly Thr Ser Ser Ser Asp Val Gly Tyr Gly Val Tyr Asp Leu Tyr
50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
                85                  90                  95

Met Gln Val Tyr Ala Asp Val Val Phe Asn His Lys Ala Gly Ala Asp
            100                 105                 110

Gly Thr Glu Leu Val Asp Ala Val Glu Val Asn Pro Ser Asp Arg Asn
        115                 120                 125

Gln Glu Ile Ser Gly Thr Tyr Gln Ile Gln Ala Trp Thr Lys Phe Asp
130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
210                 215                 220

Thr Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Val Arg Thr Gln Thr
                245                 250                 255

Gln Lys Pro Leu Phe Ala Val Gly Glu Phe Trp Ser Tyr Asp Ile Ser
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Ile Ala Ser Lys Ser Gly Gly
290                 295                 300

Tyr Phe Asp Met Arg Thr Leu Leu Asn Asn Thr Leu Met Lys Asp Gln
305                 310                 315                 320

Pro Thr Leu Ala Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
            340                 345                 350
```

```
Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Ala Leu Lys Ser Lys
    370                 375                 380

Leu Asp Pro Leu Leu Ile Ala Arg Arg Asp Tyr Ala Tyr Gly Thr Gln
385                 390                 395                 400

His Asp Tyr Ile Asp Ser Ala Asp Ile Ile Gly Trp Thr Arg Glu Gly
                405                 410                 415

Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
        435                 440                 445

Thr Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Pro Lys

<210> SEQ ID NO 7
<211> LENGTH: 586
<212> TYPE: PRT
<213> ORGANISM: bacillus sp.

<400> SEQUENCE: 7

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
            20                  25                  30

Ser Leu Ala Asn Leu Gly Ile Thr Ala Leu Trp Leu Pro Pro Ala Tyr
        35                  40                  45

Lys Gly Thr Ser Ser Ser Asp Val Gly Tyr Gly Val Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
                85                  90                  95

Met Gln Val Tyr Ala Asp Val Val Phe Asn His Lys Ala Gly Ala Asp
            100                 105                 110

Gly Thr Glu Leu Val Asp Ala Val Glu Val Asn Pro Ser Asp Arg Asn
        115                 120                 125

Gln Glu Ile Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
    210                 215                 220

Ile Thr Thr Asn Ile Asp Gly Phe Arg Leu Asp Ala Val Lys His Ile
225                 230                 235                 240
```

Lys Tyr Ser Phe Phe Pro Asp Trp Leu Ser Tyr Leu Arg Thr Gln Thr
            245                 250                 255

Gln Lys Pro Leu Phe Ala Val Gly Glu Phe Trp Ser Tyr Asp Ile Asn
            260                 265                 270

Lys Leu His Asn Tyr Ile Thr Lys Thr Asn Gly Ser Met Ser Leu Phe
            275                 280                 285

Asp Ala Pro Leu His Asn Asn Phe Tyr Ile Ala Ser Lys Ser Gly Gly
290                 295                 300

Tyr Phe Asp Met Arg Thr Leu Leu Asn Asn Thr Leu Met Lys Glu Gln
305                 310                 315                 320

Pro Thr Leu Ser Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
                340                 345                 350

Ala Phe Ile Leu Thr Arg Gln Glu Gly Tyr Pro Cys Val Phe Tyr Gly
                355                 360                 365

Asp Tyr Tyr Gly Ile Pro Lys Tyr Asn Ile Pro Ala Leu Lys Ser Lys
            370                 375                 380

Leu Asp Pro Leu Leu Ile Ala Arg Arg Asp Tyr Ala Tyr Gly Thr Gln
385                 390                 395                 400

His Asp Tyr Ile Asp Asn Ala Asp Ile Ile Gly Trp Thr Arg Glu Gly
                405                 410                 415

Val Ala Glu Lys Ala Asn Ser Gly Leu Ala Ala Leu Ile Thr Asp Gly
                420                 425                 430

Pro Gly Gly Ser Lys Trp Met Tyr Val Gly Lys Gln His Ala Gly Lys
                435                 440                 445

Thr Phe Tyr Asp Leu Thr Gly Asn Arg Ser Asp Thr Val Thr Ile Asn
            450                 455                 460

Ala Asp Gly Trp Gly Glu Phe Lys Val Asn Gly Gly Ser Val Ser Ile
465                 470                 475                 480

Trp Val Pro Lys Thr Ser Thr Ser Gln Ile Thr Phe Thr Val Asn
                485                 490                 495

Asn Ala Thr Thr Val Trp Gly Gln Asn Val Tyr Val Val Gly Asn Ile
                500                 505                 510

Ser Gln Leu Gly Asn Trp Asp Pro Val Asn Ala Val Gln Met Thr Pro
            515                 520                 525

Ser Ser Tyr Pro Thr Trp Val Val Thr Val Pro Leu Pro Gln Ser Gln
            530                 535                 540

Asn Ile Gln Phe Lys Phe Ile Lys Lys Asp Gly Ser Gly Asn Val Ile
545                 550                 555                 560

Trp Glu Asn Ile Ser Asn Arg Thr Tyr Thr Val Pro Thr Ala Ala Ser
                565                 570                 575

Gly Ala Tyr Thr Ala Asn Trp Asn Val Pro
                580                 585

<210> SEQ ID NO 8
<211> LENGTH: 484
<212> TYPE: PRT
<213> ORGANISM: bacillus sp.

<400> SEQUENCE: 8

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln

-continued

```
             20                  25                  30
Ser Leu Ala Asn Leu Gly Ile Thr Ala Leu Trp Leu Pro Ala Tyr
             35                  40                  45
Lys Gly Thr Ser Ser Asp Val Gly Tyr Gly Val Tyr Asp Leu Tyr
             50                  55                  60
Asp Leu Gly Glu Phe Asn Gln Lys Gly Thr Val Arg Thr Lys Tyr Gly
 65                  70                  75                  80
Thr Lys Thr Gln Tyr Ile Gln Ala Ile Gln Ala His Thr Ala Gly
                     85                  90                  95
Met Gln Val Tyr Ala Asp Val Phe Asn His Lys Ala Gly Ala Asp
                    100                 105                 110
Gly Thr Glu Leu Val Asp Ala Val Glu Val Asn Pro Ser Asp Arg Asn
                    115                 120                 125
Gln Glu Ile Ser Gly Thr Tyr Gln Ile Gln Ala Trp Thr Lys Phe Asp
                    130                 135                 140
Phe Pro Gly Arg Gly Asn Thr Tyr Ser Ser Phe Lys Trp Arg Trp Tyr
145                 150                 155                 160
His Phe Asp Gly Thr Asp Trp Asp Glu Ser Arg Lys Leu Asn Arg Ile
                    165                 170                 175
Tyr Lys Phe Arg Gly Thr Gly Lys Ala Trp Asp Trp Glu Val Asp Thr
                    180                 185                 190
Glu Asn Gly Asn Tyr Asp Tyr Leu Met Tyr Ala Asp Leu Asp Met Asp
                    195                 200                 205
His Pro Glu Val Val Ser Glu Leu Lys Asn Trp Gly Lys Trp Tyr Val
                    210                 215                 220
Ile Thr Thr Asn Ile Asp Gly Phe Arg Leu Asp Ala Val Lys His Ile
225                 230                 235                 240
Lys Tyr Ser Phe Phe Pro Asp Trp Leu Ser Tyr Leu Arg Thr Gln Thr
                    245                 250                 255
Gln Lys Pro Leu Phe Ala Val Gly Glu Phe Trp Ser Tyr Asp Ile Asn
                    260                 265                 270
Lys Leu His Asn Tyr Ile Thr Lys Thr Asn Gly Ser Met Ser Leu Phe
                    275                 280                 285
Asp Ala Pro Leu His Asn Asn Phe Tyr Ile Ala Ser Lys Ser Gly Gly
                    290                 295                 300
Tyr Phe Asp Met Arg Thr Leu Leu Asn Asn Thr Leu Met Lys Glu Gln
305                 310                 315                 320
Pro Thr Leu Ser Val Thr Leu Val Asp Asn His Asp Thr Glu Pro Gly
                    325                 330                 335
Gln Ser Leu Gln Ser Trp Val Glu Pro Trp Phe Lys Pro Leu Ala Tyr
                    340                 345                 350
Ala Phe Ile Leu Thr Arg Gln Glu Gly Tyr Pro Cys Val Phe Tyr Gly
                    355                 360                 365
Asp Tyr Tyr Gly Ile Pro Lys Tyr Asn Ile Pro Ala Leu Lys Ser Lys
                    370                 375                 380
Leu Asp Pro Leu Leu Ile Ala Arg Arg Asp Tyr Ala Tyr Gly Thr Gln
385                 390                 395                 400
His Asp Tyr Ile Asp Asn Ala Asp Ile Ile Gly Trp Thr Arg Glu Gly
                    405                 410                 415
Val Ala Glu Lys Ala Asn Ser Gly Leu Ala Ala Leu Ile Thr Asp Gly
                    420                 425                 430
Pro Gly Gly Ser Lys Trp Met Tyr Val Gly Lys Gln His Ala Gly Lys
                    435                 440                 445
```

Thr Phe Tyr Asp Leu Thr Gly Asn Arg Ser Asp Thr Val Thr Ile Asn
        450                 455                 460

Ala Asp Gly Trp Gly Glu Phe Lys Val Asn Gly Ser Val Ser Ile
465                 470                 475                 480

Trp Val Pro Lys

<210> SEQ ID NO 9
<211> LENGTH: 1446
<212> TYPE: DNA
<213> ORGANISM: Artificial Sequence
<220> FEATURE:
<223> OTHER INFORMATION: synthetic construct

<400> SEQUENCE: 9

| | | | |
|---|---|---|---|
| aatactgcac ctattaacga aacaatgatg caatattttg aatgggattt accgaacgat | 60 |
| ggaacccttt ggacaaaggt gaaaaatgaa gccgcaaatc tttcttcgct cggtattaca | 120 |
| gcgttatggc ttcctccagc gtataaagga acaagtcaaa gcgatgtcgg atacggcgtg | 180 |
| tacgatttat atgaccttgg ggaatttaat caaaaggaa cgattcgaac aaaatacgga | 240 |
| acaaaaacac aatatattca agccatccaa gctgccaaag ccgcagggat gcaagtatat | 300 |
| gcagatgttg tctttaatca taaggcggga gctgacggca cagaatttgt cgatgcggtt | 360 |
| gaggtagacc cttctaatcg aaatcaagaa acatctggaa catatcaaat tcaagcatgg | 420 |
| acaaaatttg attttcccgg tcgggggaac acatactcga gttttaaatg gcgttggtat | 480 |
| cattttgacg gtaccgattg ggatgaaagc cgaaaattaa atcggattta caaattcaca | 540 |
| ggaaaagcat gggactggga agtcgataca gaaaacggaa actatgatta tttaatgttc | 600 |
| gctgatttag atatggatca ccctgaggtt gtgacagaat taaaaaactg ggaacgtgg | 660 |
| tacgtcaata ctacaaatat cgatggattc cgcttagatg ccgtaaaaca tattaaatac | 720 |
| agcttttttcc ctgactggct aacatatgta cgtaatcaaa caggaaaaaa tttatttgcc | 780 |
| gttggggaat tttggagcta tgacgtcaat aagctgcata attacattac aaaaacaaat | 840 |
| ggatcgatgt cattatttga tgcacctttg cataacaact tttataccgc ttccaaatcg | 900 |
| agtggatatt ttgacatgcg ttatttattg aataatacat taatgaaaga tcaaccttca | 960 |
| ctcgctgtga cacttgtcga taaccacgac acgcaaccag gcaatctttt acagtcatgg | 1020 |
| gtcgaaccct tggtttaaacc acttgcttac gcctttattt taacgagaca agagggatat | 1080 |
| ccttgcgtat tttacggtga ctattatgga atcccgaaat acaatattcc aggattaaaa | 1140 |
| agcaaaatcg acccgctttt aattgctcgt cgggactatg cctatggaac aaacgtgat | 1200 |
| tacattgacc atcaagacat tattggatgg acacgcgaag gcattgatac aaaaccaaac | 1260 |
| tctggactgg cggctttaat taccgacggc cctggcggaa gcaaatggat gtatgtcggt | 1320 |
| aaaaaacatg ctggaaaagt attttatgat ttaaccggaa accgaagtga cacagtaacg | 1380 |
| attaatgcgg atggttgggg agaatttaaa gtaaacggag gctccgtttc gatttgggtg | 1440 |
| gctaaa | 1446 |

<210> SEQ ID NO 10
<211> LENGTH: 482
<212> TYPE: PRT
<213> ORGANISM: artificial sequence
<220> FEATURE:
<223> OTHER INFORMATION: synthetic construct

<400> SEQUENCE: 10

```
Asn Thr Ala Pro Ile Asn Glu Thr Met Met Gln Tyr Phe Glu Trp Asp
  1               5                  10                  15
Leu Pro Asn Asp Gly Thr Leu Trp Thr Lys Val Lys Asn Glu Ala Ala
                 20                  25                  30
Asn Leu Ser Ser Leu Gly Ile Thr Ala Leu Trp Leu Pro Pro Ala Tyr
             35                  40                  45
Lys Gly Thr Ser Gln Ser Asp Val Gly Tyr Gly Val Tyr Asp Leu Tyr
 50                  55                  60
Asp Leu Gly Glu Phe Asn Gln Lys Gly Thr Ile Arg Thr Lys Tyr Gly
 65                  70                  75                  80
Thr Lys Thr Gln Tyr Ile Gln Ala Ile Gln Ala Ala Lys Ala Ala Gly
                 85                  90                  95
Met Gln Val Tyr Ala Asp Val Val Phe Asn His Lys Ala Gly Ala Asp
                100                 105                 110
Gly Thr Glu Phe Val Asp Ala Val Glu Val Asp Pro Ser Asn Arg Asn
                115                 120                 125
Gln Glu Thr Ser Gly Thr Tyr Gln Ile Gln Ala Trp Thr Lys Phe Asp
                130                 135                 140
Phe Pro Gly Arg Gly Asn Thr Tyr Ser Ser Phe Lys Trp Arg Trp Tyr
145                 150                 155                 160
His Phe Asp Gly Thr Asp Trp Asp Glu Ser Arg Lys Leu Asn Arg Ile
                165                 170                 175
Tyr Lys Phe Thr Gly Lys Ala Trp Asp Trp Glu Val Asp Thr Glu Asn
                180                 185                 190
Gly Asn Tyr Asp Tyr Leu Met Phe Ala Asp Leu Asp Met Asp His Pro
                195                 200                 205
Glu Val Val Thr Glu Leu Lys Asn Trp Gly Thr Trp Tyr Val Asn Thr
                210                 215                 220
Thr Asn Ile Asp Gly Phe Arg Leu Asp Ala Val Lys His Ile Lys Tyr
225                 230                 235                 240
Ser Phe Phe Pro Asp Trp Leu Thr Tyr Val Arg Asn Gln Thr Gly Lys
                245                 250                 255
Asn Leu Phe Ala Val Gly Glu Phe Trp Ser Tyr Asp Val Asn Lys Leu
                260                 265                 270
His Asn Tyr Ile Thr Lys Thr Asn Gly Ser Met Ser Leu Phe Asp Ala
                275                 280                 285
Pro Leu His Asn Asn Phe Tyr Thr Ala Ser Lys Ser Ser Gly Tyr Phe
                290                 295                 300
Asp Met Arg Tyr Leu Leu Asn Asn Thr Leu Met Lys Asp Gln Pro Ser
305                 310                 315                 320
Leu Ala Val Thr Leu Val Asp Asn His Asp Thr Gln Pro Gly Gln Ser
                325                 330                 335
Leu Gln Ser Trp Val Glu Pro Trp Phe Lys Pro Leu Ala Tyr Ala Phe
                340                 345                 350
Ile Leu Thr Arg Gln Glu Gly Tyr Pro Cys Val Phe Tyr Gly Asp Tyr
                355                 360                 365
Tyr Gly Ile Pro Lys Tyr Asn Ile Pro Gly Leu Lys Ser Lys Ile Asp
370                 375                 380
Pro Leu Leu Ile Ala Arg Arg Asp Tyr Ala Tyr Gly Thr Gln Arg Asp
385                 390                 395                 400
Tyr Ile Asp His Gln Asp Ile Ile Gly Trp Thr Arg Glu Gly Ile Asp
                405                 410                 415
Thr Lys Pro Asn Ser Gly Leu Ala Ala Leu Ile Thr Asp Gly Pro Gly
```

```
            420             425             430
Gly Ser Lys Trp Met Tyr Val Gly Lys Lys His Ala Gly Lys Val Phe
        435             440             445

Tyr Asp Leu Thr Gly Asn Arg Ser Asp Thr Val Thr Ile Asn Ala Asp
        450             455             460

Gly Trp Gly Glu Phe Lys Val Asn Gly Gly Ser Val Ser Ile Trp Val
465             470             475             480

Ala Lys

<210> SEQ ID NO 11
<211> LENGTH: 1452
<212> TYPE: DNA
<213> ORGANISM: bacillus sp TS23

<400> SEQUENCE: 11
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taggcggga gctgacggca cagaatttgt cgatgcggtt     360
gaggtagacc cttctaatcg aaatcaagaa acatctggaa catatcaaat tcaagcatgg     420
acaaaatttg attttcccgg tcgggggaac acatactcga gttttaaatg cgttggtat     480 catttttgacg gtaccgattg ggatgaaagc cgaaaattaa atcggattta caaattccgc     540
agtacaggaa aagcatggga ctgggaagtc gatacagaaa acggaaacta tgattattta     600
atgttcgctg atttagatat ggatcaccct gaggttgtga cagaattaaa aaactgggga     660
acgtggtacg tcaatactac aaatatcgat ggattccgct tagatgccgt aaaacatatt     720
aaatacagct ttttccctga ctggctaaca tatgtacgta atcaaacagg aaaaaattta     780
tttgccgttg gggaattttg gagctatgac gtcaataagc tgcataatta cattacaaaa     840
acaaatggat cgatgtcatt atttgatgca cctttgcata caacttttta taccgcttcc     900
aaatcgagtg atattttga catgcgttat ttattgaata atcattaat gaaagatcaa     960 ccttcactcg ctgtgacact tgtcgataac cacgacacgc aaccaggca atctttacag    1020 tcatgggtcg aaccttggtt taaccacttt gcttacgcct ttattttaac gagacaagag    1080
ggatatcctt gcgtatttta cggtgactat tatggaatcc cgaaatacaa tattccagga    1140
ttaaaaagca aaatcgaccc gcttttaatt gctcgtcggg actatgccta tggaacacaa    1200
cgtgattaca ttgaccatca agacattatt ggatggacac gcgaaggcat tgatacaaaa    1260
ccaaactctg gactggcggc tttaattacc gacggccctg gcggaagcaa atggatgtat    1320
gtcggtaaaa aacatgctgg aaaagtattt tatgatttaa ccgaaaaccg aagtgacaca    1380
gtaacgatta tgcggatgg ttggggagaa tttaaagtaa acggaggctc cgtttcgatt    1440
tgggtggcta aa                                                       1452

<210> SEQ ID NO 12
<211> LENGTH: 49
<212> TYPE: DNA
<213> ORGANISM: Artificial sequence
<220> FEATURE:
<223> OTHER INFORMATION: Primer
```

```
<400> SEQUENCE: 12
ggctccgttt cgatttgggt ggctaaatag tcgcatgttc aatccgctc                49

<210> SEQ ID NO 13
<211> LENGTH: 49
<212> TYPE: DNA
<213> ORGANISM: Artificial sequence
<220> FEATURE:
<223> OTHER INFORMATION: Primer

<400> SEQUENCE: 13
gagcggattg aacatgcgac tatttagcca cccaaatcga aacggagcc                49

<210> SEQ ID NO 14
<211> LENGTH: 32
<212> TYPE: DNA
<213> ORGANISM: Artificial sequence
<220> FEATURE:
<223> OTHER INFORMATION: Primer

<400> SEQUENCE: 14
ccgttttctg tatcgacttc ccagtcccat gc                                  32

<210> SEQ ID NO 15
<211> LENGTH: 32
<212> TYPE: DNA
<213> ORGANISM: Artificial sequence
<220> FEATURE:
<223> OTHER INFORMATION: Primer

<400> SEQUENCE: 15
gcatgggact gggaagtcga tacagaaaac gg                                  32
```